United States Patent
Matthews

(10) Patent No.: US 11,226,337 B2
(45) Date of Patent: Jan. 18, 2022

(54) CHEMOPROTEOMIC PROFILING OF PROTEIN ELECTROPHILIC AND OXIDATIVE POST-TRANSLATIONAL MODIFICATIONS

(71) Applicant: Zenagem, LLC, Philadelphia, PA (US)

(72) Inventor: Megan L. Matthews, Philadelphia, PA (US)

(73) Assignee: ZENAGEM, LLC, Philadelphia, PA (US)

(*) Notice: Subject to any disclaimer, the term of this patent is extended or adjusted under 35 U.S.C. 154(b) by 168 days.

(21) Appl. No.: 16/175,388

(22) Filed: Oct. 30, 2018

(65) Prior Publication Data

US 2019/0204336 A1 Jul. 4, 2019

Related U.S. Application Data

(60) Provisional application No. 62/579,497, filed on Oct. 31, 2017.

(51) Int. Cl.
*G01N 33/68* (2006.01)
*C07K 14/00* (2006.01)
*C40B 70/00* (2006.01)

(52) U.S. Cl.
CPC ....... *G01N 33/6833* (2013.01); *C07K 14/001* (2013.01); *G01N 33/6842* (2013.01);
(Continued)

(58) Field of Classification Search
CPC ........... G01N 33/6842; G01N 33/6833; G01N 33/6845; G01N 33/6848; G01N 2440/00;
(Continued)

(56) References Cited

U.S. PATENT DOCUMENTS

| 7,183,118 B2 | 2/2007 | Aebersold et al. |
| 2005/0287594 A1 | 12/2005 | Cravatt et al. |
| 2010/0009380 A1 | 1/2010 | Carroll |

OTHER PUBLICATIONS

Cravatt et al. Activity based protein profiling: form enzymatic chemistry to proteomic chemistry. Annu. Rev. Biochem. 2008. vol. 77, pp. 383-414. (Year: 2008).*

(Continued)

*Primary Examiner* — Shafiqul Haq
(74) *Attorney, Agent, or Firm* — One LLP

(57) ABSTRACT

Chemoproteomic methods for detecting and profiling electrophilic post-translational modifications (PTMs) and oxidative PTMs in proteins are described. The methods including contacting a proteomic mixture with a probe having hydrazine and alkyne moieties or oxyamine and alkyne moieties to form a covalent linkage between the hydrazine or oxyamine moiety of the probe and the electrophilic PTM or oxidative PTM of the protein. The resulting alkyne-derivatized proteins are labelled with an azide modified tag via a click chemistry reaction. The labelled proteins can then be detected or profiled using techniques such as, for example, fluorescence imaging or mass spectrometry. Also described are protein conjugates having a covalent linkage formed by reaction of a hydrazine or oxyamine moiety of a probe with an electrophilic or oxidative PTM of a protein.

13 Claims, 28 Drawing Sheets
(27 of 28 Drawing Sheet(s) Filed in Color)
Specification includes a Sequence Listing.

probe 2 probe 3

(52) U.S. Cl.
CPC ..... *G01N 33/6845* (2013.01); *G01N 33/6848* (2013.01); *C40B 70/00* (2013.01); *G01N 2440/00* (2013.01); *G01N 2458/10* (2013.01)

(58) Field of Classification Search
CPC ... G01N 2458/10; C07K 14/001; C40B 70/00
See application file for complete search history.

(56) References Cited

OTHER PUBLICATIONS

Han et al. Design, synthesis, and application of a hydrazide-functionalized isotope-doded affinity tag for the quantification of oxylipid-protein conjugates. Anal. Chem. 2007, vol. 79, pp. 3342-3354. (Year: 2007).*

Fischer-Durand et al. A new bioorthogonal cross-linker with alkyne and dydrazide end groups for chemoselective ligantion. Application to antibody labelling. Tetrahedron 2012, vol. 68, pp. 9638-9644. (Year: 2012).*

Augusto et al., "N-Phenylprotoporphyrin IX Formation in the Hemoglobin-Phenylhydrazine Reaction," The Journal of Biological Chemistry, vol. 257, No. 11, Issue of Jun. 10, pp. 6231-6241 (1982).

Binda et al., "Structural and Mechanistic Studies of Arylalkylhydrazine Inhibition of Human Monoamine Oxidases A and B," Biochemistry, vol. 47, pp. 5616-5625 (2008).

Chang et al., "Chemoproteomic Profiling of Phosphoaspartate Modifications in Prokaryotes," Angewandte Chem. Int. Ed., vol. 57, pp. 15712-15716 (2018).

Dalle-Donne et al., "Protein carbonylation: 2,4-dinitrophenylhydrazine reacts with both aldehydes/ketones and sulfenic acids," Free Radical Biology & Medicine, vol. 46, pp. 1411-1419 (2009).

Dirksen et al., "Rapid Oxime and Hydrazone Ligations with Aromatic Aldehydes for Biomolecular Labeling," Bioconjugate Chem., vol. 19, pp. 2543-2548 (2008).

Klaene et al., "Detection and Quantitation of Succinimide in Intact Protein via Hydrazine Trapping and Chemical Derivatization," J. Pharm. Sci., vol. 103, No. 10, pp. 3033-3042 (Oct. 2014).

Matthews et al., "Chemoproteomic profiling and discovery of protein electrophiles in human cells," Nature Chemistry, vol. 9, No. 3, pp. 234-243 (2017).

Morgan et al., "A Clickable Aminooxy Probe for Monitoring Cellular ADP-Ribosylation," ACS Chem. Biol., vol. 10, pp. 1778-1784 (2015).

Speers et al., "Profiling Enzyme Activities In Vivo Using Click Chemistry Methods," Chemistry & Biology, vol. 11, pp. 535-546 (Apr. 2004).

Weerapana et al., "Tandem orthogonal proteolysis-activity-based protein profiling (TOP-ABPP)-a general method for mapping sites of probe modification in proteomes," Nature Protocols, vol. 2, No. 6, pp. 1414-1425 (2007).

Alfaro, J. F., et al., "Chemo-Enzymatic Detection of Protein Isoaspartate Using Protein Isoaspartate Methyltransferase and Hydrazine Trapping", Anal. Chem., 2008, vol. 80, No. 10, pp. 3882-3889.

Bollineni, R. C., et al., "Proteome-wide profiling of carbonylated proteins and carbonylation sites in HeLa cells under mild oxidative stress conditions", Free Radical Biology and Medicine, 2014, vol. 68, pp. 186-195.

Fritz, K. S., "An overview of the chemistry and biology of reactive aldehydes", Free Radical Biology and Medicine, 2013, vol. 59, pp. 85-91.

Madian, A. G., et al., "Proteomic Identification of Carbonylated Proteins and Their Oxidation Sites", Journal of Proteome Research, 2010, vol. 9, No. 8, pp. 3766-3780.

Singh, R., et al., "Advanced glycation end-products: a review", Diabetologia, 2001, vol. 44, pp. 129-146.

Spiess, P. C., et al., "Proteomic profiling of acrolein adducts in human lung epithelial cells", Journal of Proteomics, 2011, vol. 74, pp. 2380-2394.

Zhang, H., et al., "Identification and quantification of N-linked glycoproteins using hydrazide chemistry, stable isotope labeling and mass spectrometry", Nature Biotechnology, 2003, vol. 21, No. 6, pp. 660-666.

* cited by examiner

FIG. 1
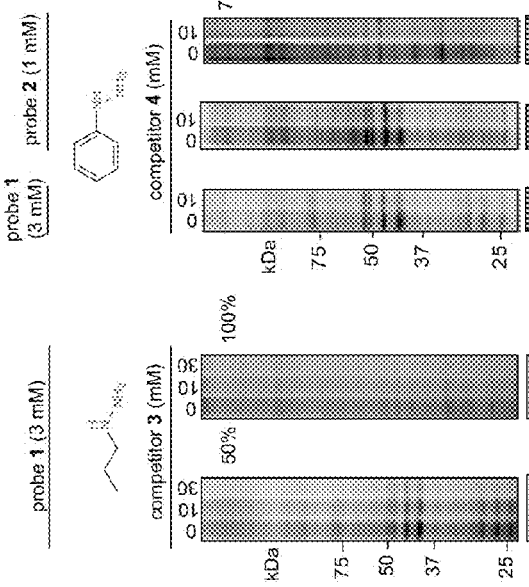
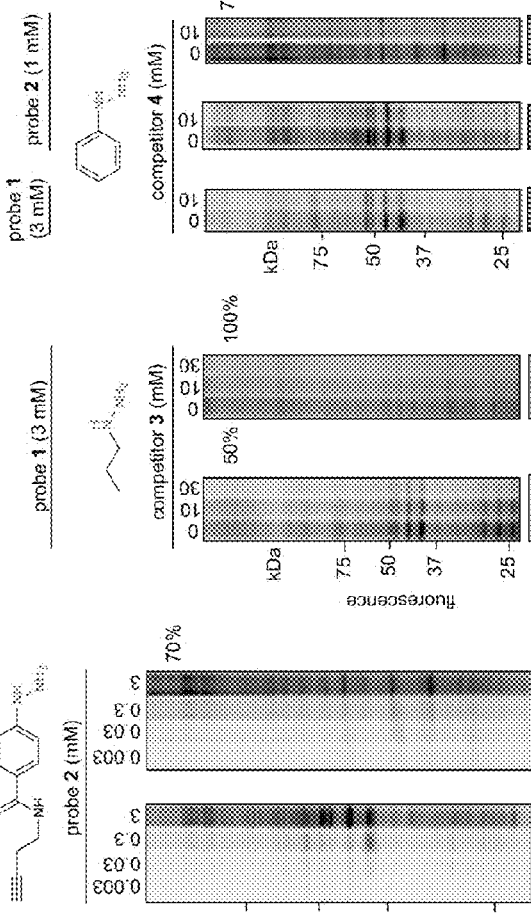
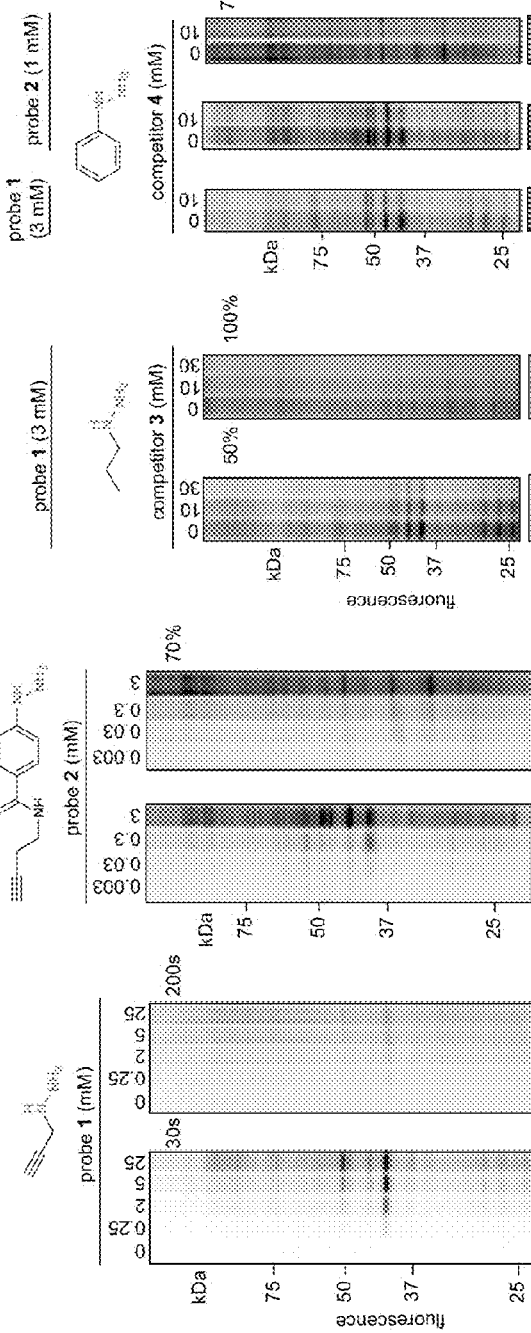
FIG. 2A  FIG. 2B  FIG. 2C  FIG. 2D

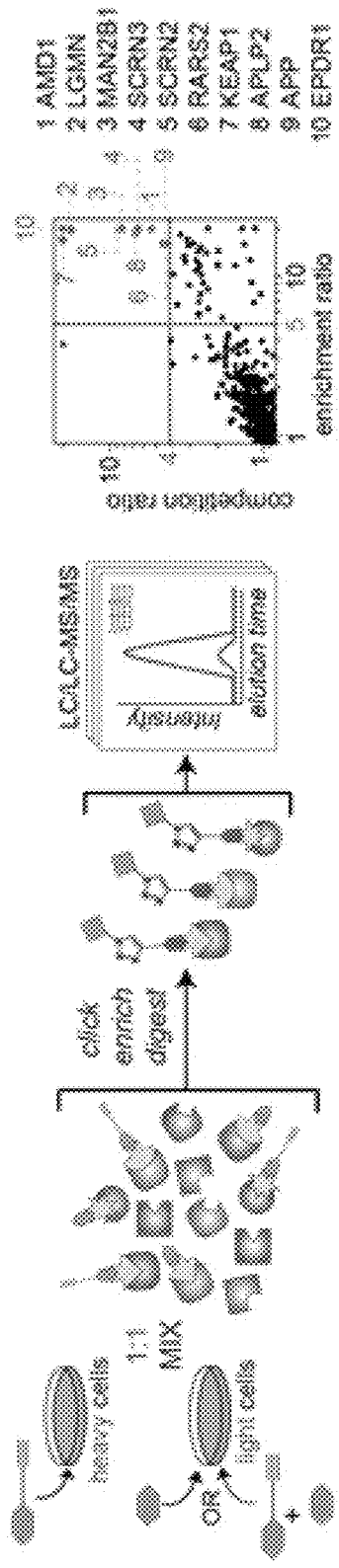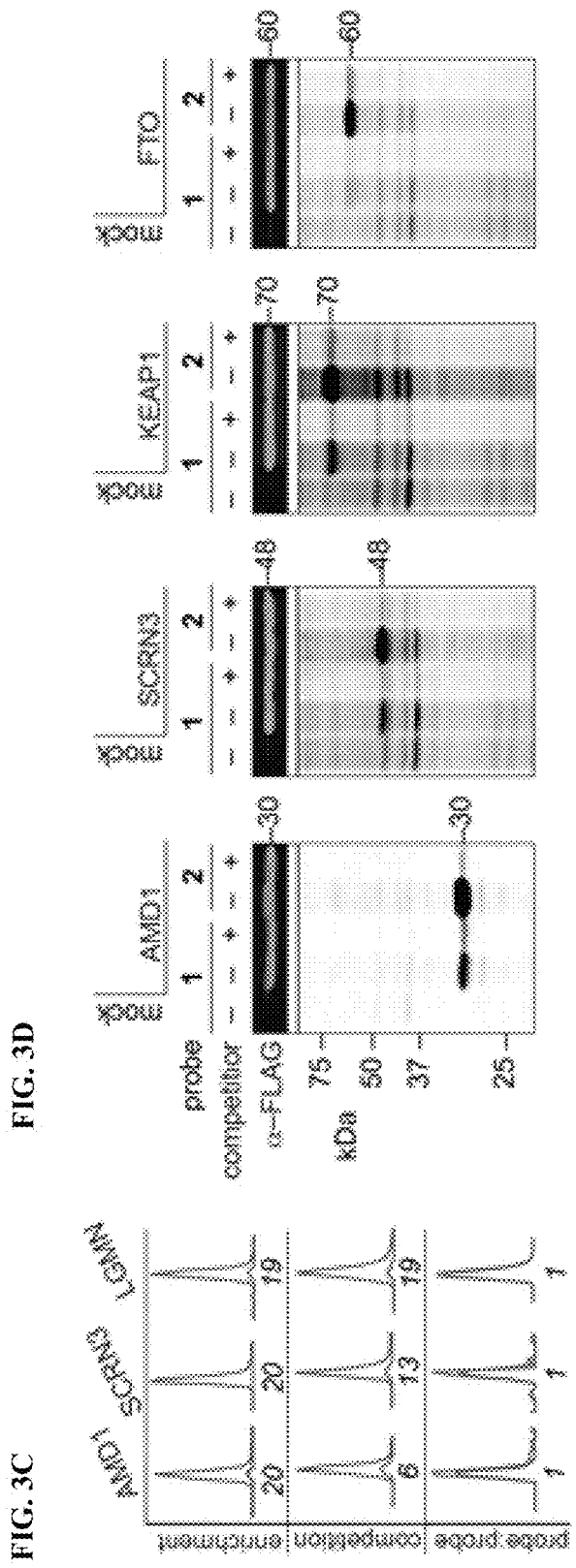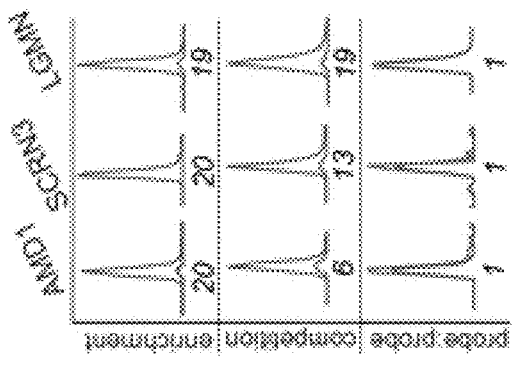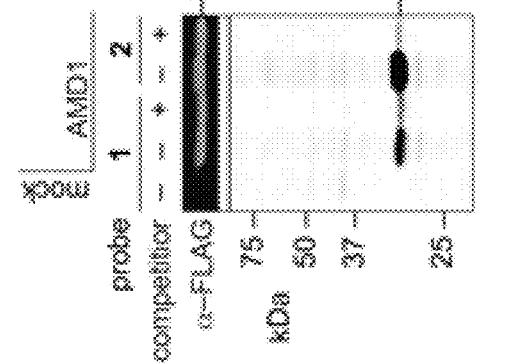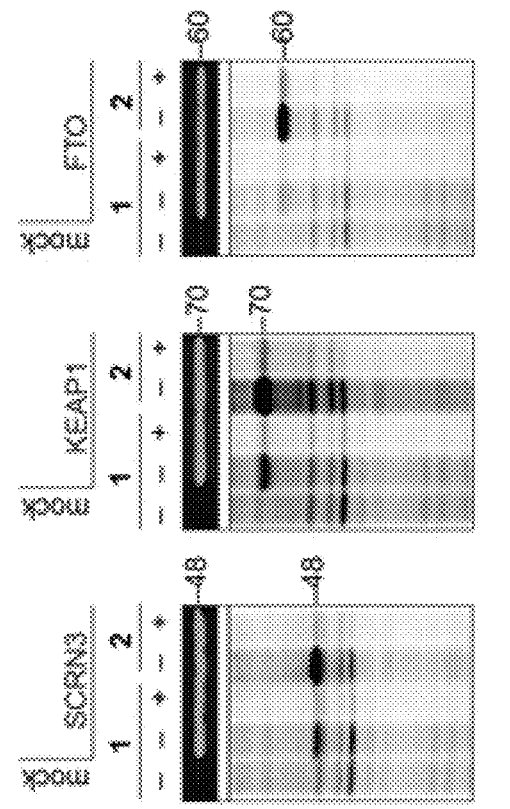
FIG. 3A
FIG. 3B
FIG. 3C
FIG. 3D

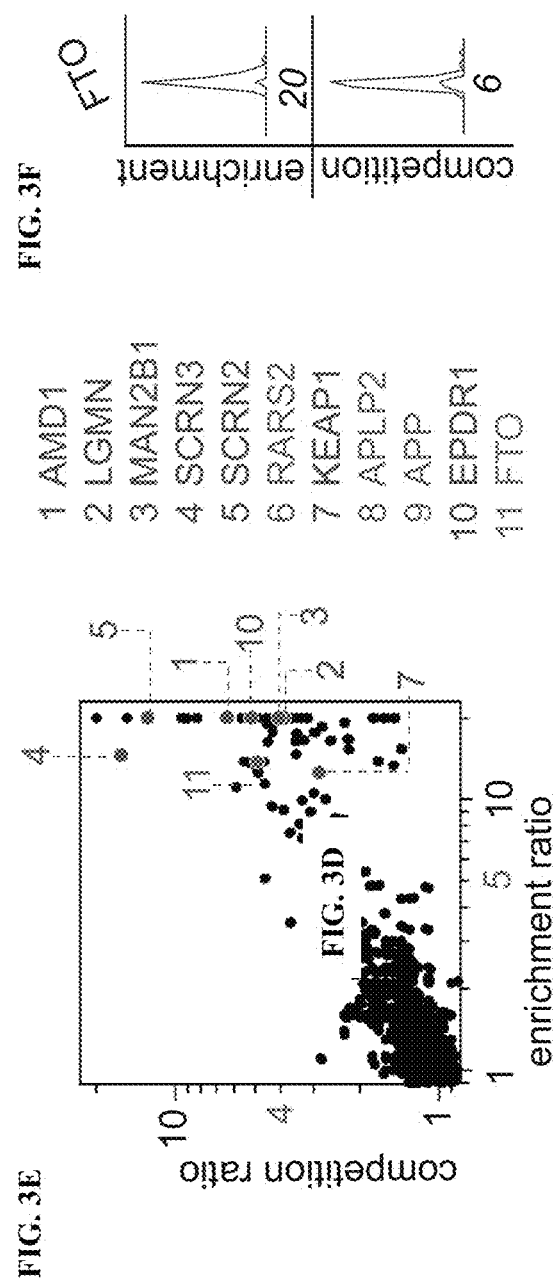

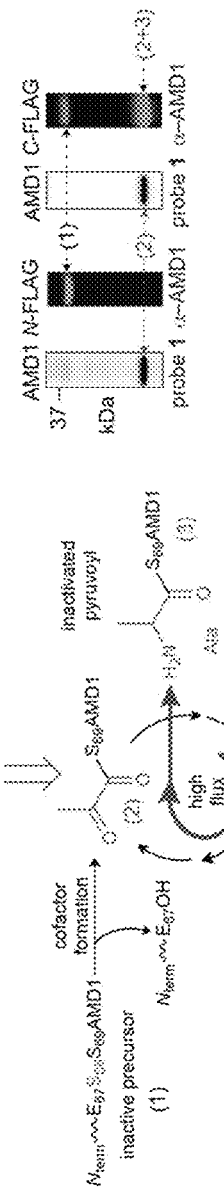
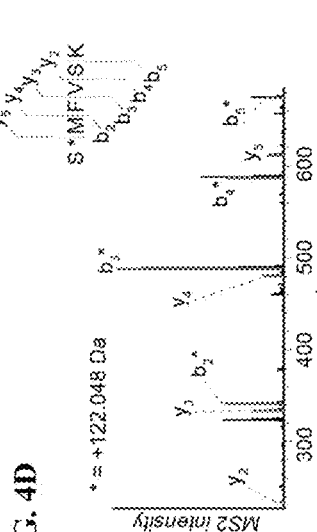
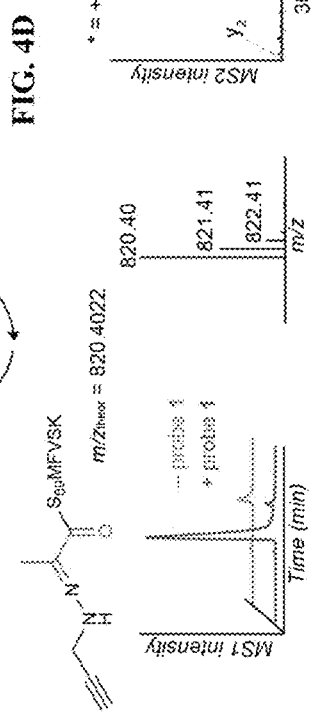
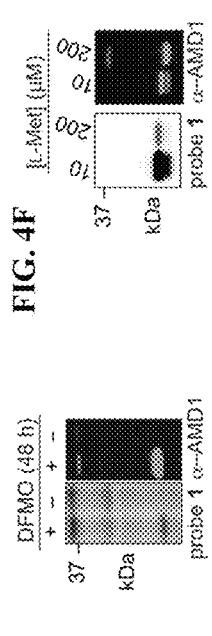
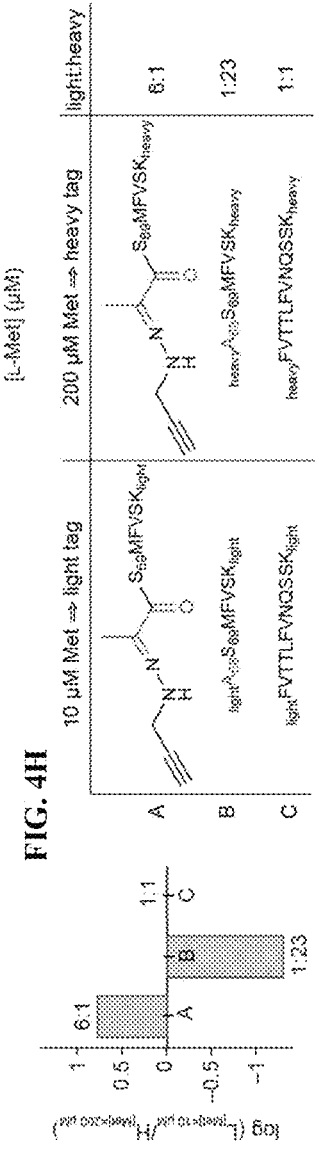
FIG. 4A
FIG. 4B
FIG. 4C
FIG. 4D
FIG. 4E
FIG. 4F
FIG. 4G
FIG. 4H

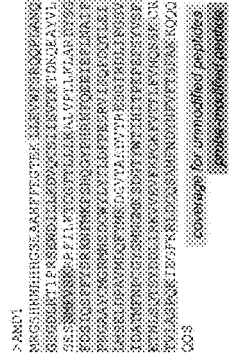
FIG. 5A
FIG. 5B
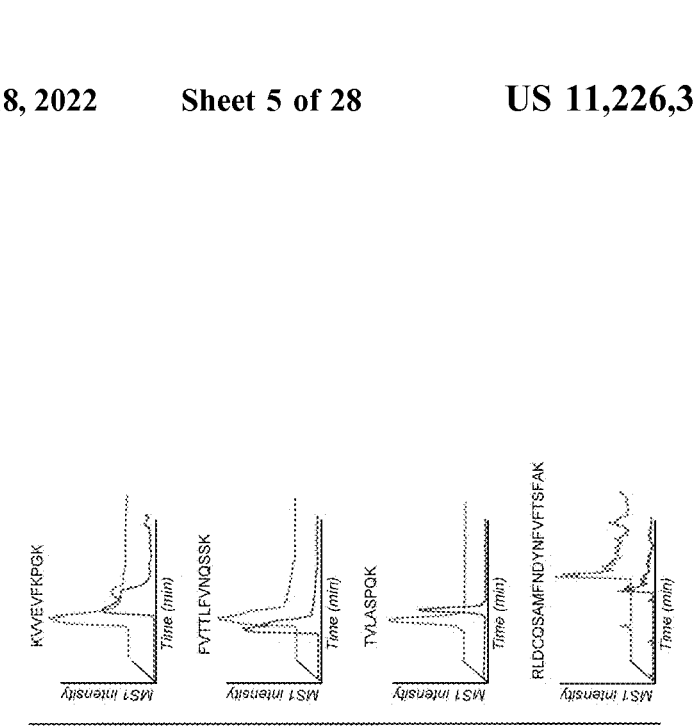
FIG. 5C
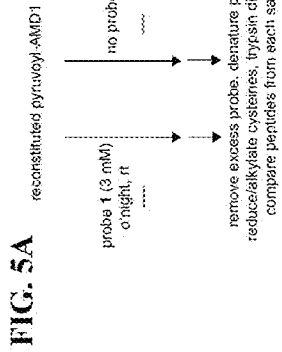
FIG. 5D
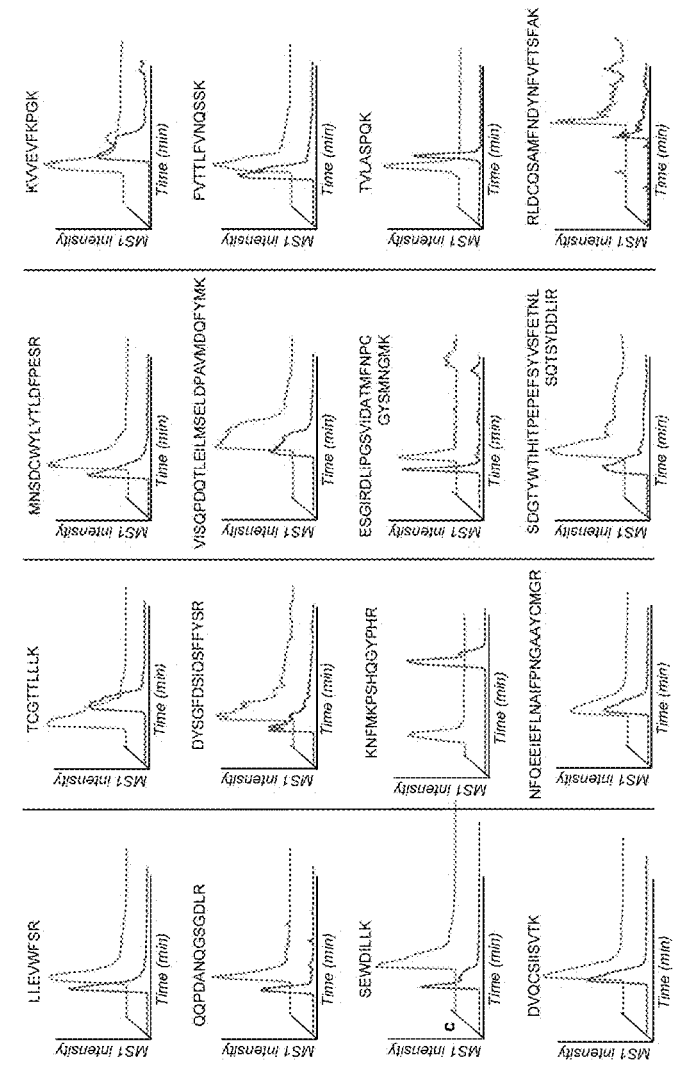

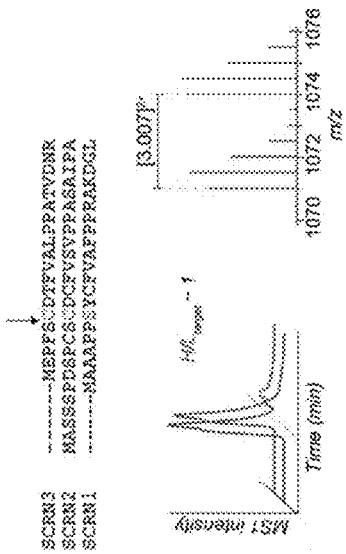
FIG. 6B
FIG. 6C
FIG. 6D
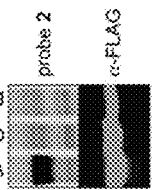
FIG. 6E
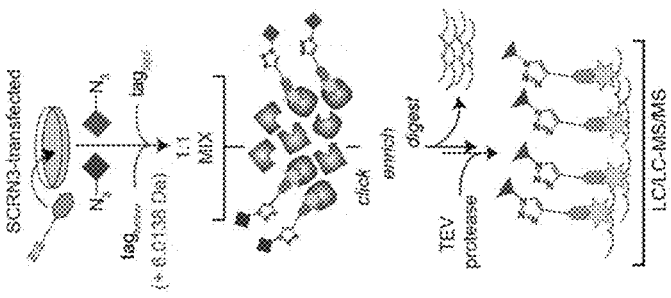
FIG. 6A
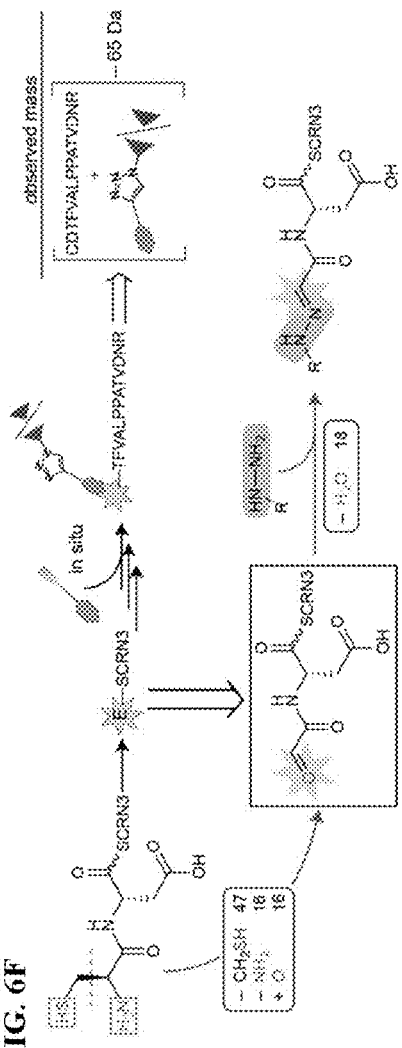
FIG. 6F

FIG. 7F
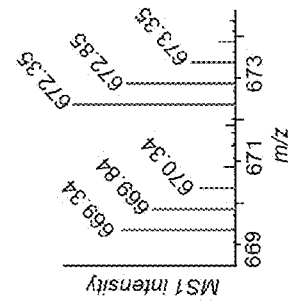
FIG. 7G
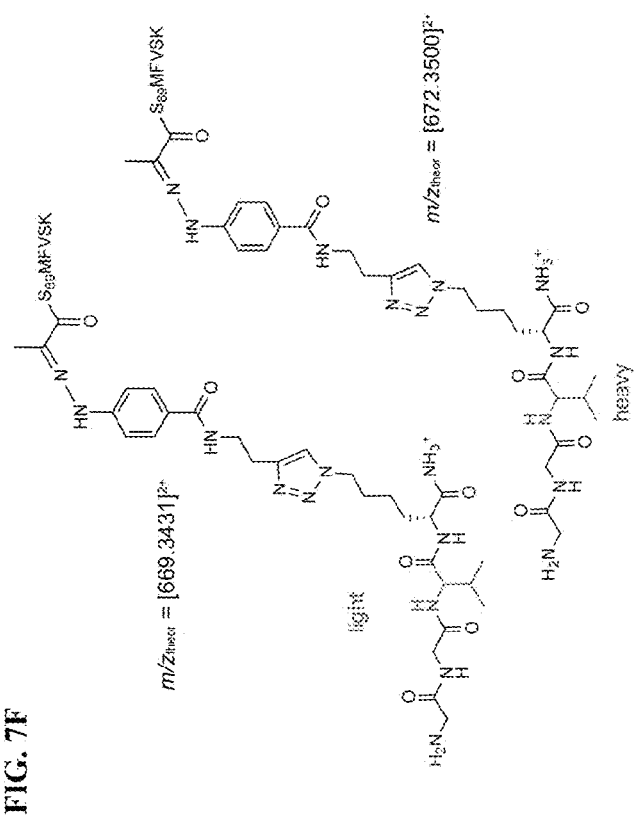
FIG. 7H
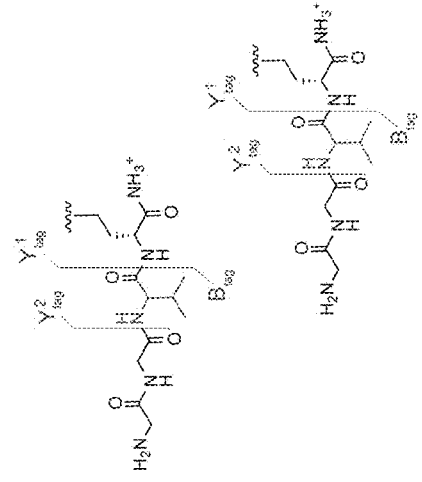
FIG. 7I
| | Theoretical m/z | | Observed m/z (high resolution MS2) | |
|---|---|---|---|---|
| | Heavy | Light | Heavy | Light |
| $[M+2H-NH_3]^{2+}$ | 663.8367 | 660.6290 | 663.8333 | 660.6271 |
| $[M+2H-NH_3CO]^{2+}$ | 649.8392 | 646.8323 | 649.8306 | 646.8225 |
| $[Y^2_{tag}]^{2+}$ | 615.3290 | 612.3216 | 615.3254 | 612.3189 |
| $B_{tag}$ | 220.1324 | 214.1186 | - | 214.4240 |
| $Y^1_{tag}$ | 1,124.5570 | 1,124.5570 | 1,124.5675 | 1,124.5537 |
| $[Y^1_{tag}]^{2+}$ | 562.7874 | 562.7874 | 562.7644 | 562.7644 |
| $Y^1_{tag}-NH_3CO$ | 1,079.5455 | | - | - |
| $[Y^1_{tag}-NH_3CO]^{2+}$ | 540.2767 | 540.2767 | 540.2744 | 540.2744 |
| $y_5$ | 611.3221 | 611.3221 | 611.3195 | 611.2347 |
| $y_4$ | 480.2841 | 480.2841 | 480.2773 | 480.2784 |
| $y_3$ | 333.2132 | 333.2132 | 333.2115 | 333.2104 |
| $y_2$ | 234.1448 | 234.1448 | 234.1434 | 234.1437 |

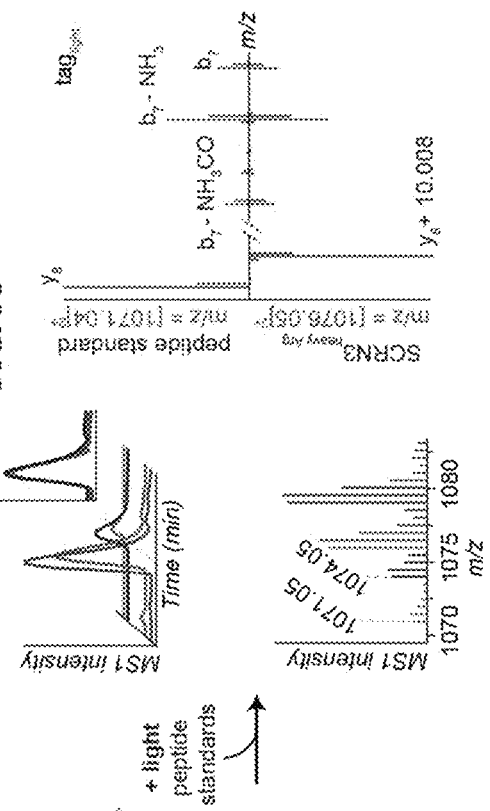
FIG. 8A
FIG. 8B
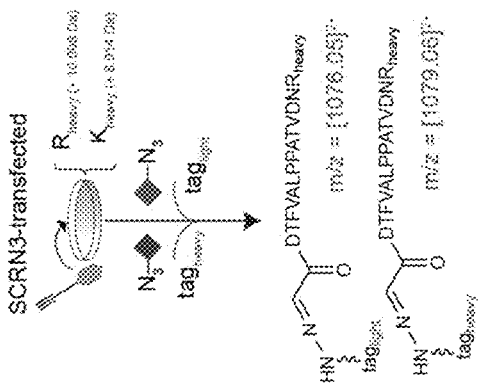
FIG. 8C

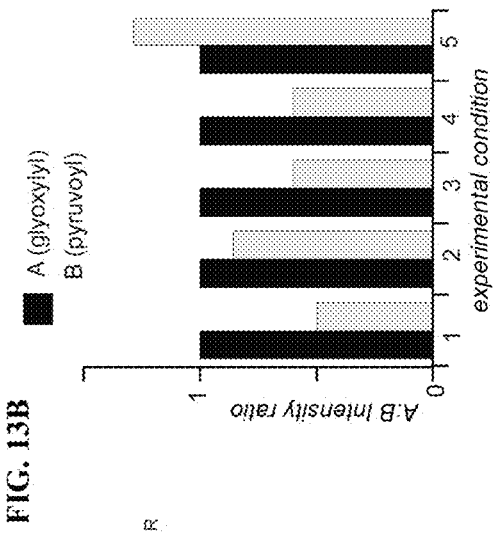
FIG. 13A
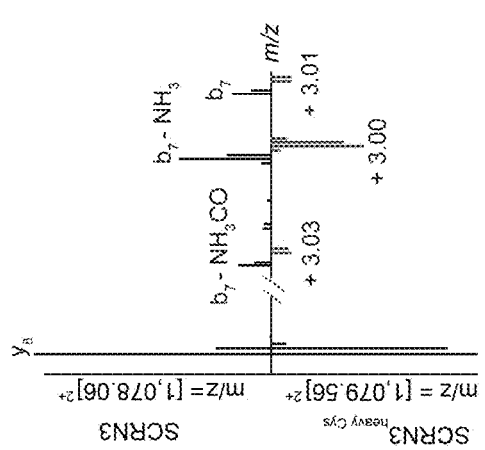
FIG. 13B
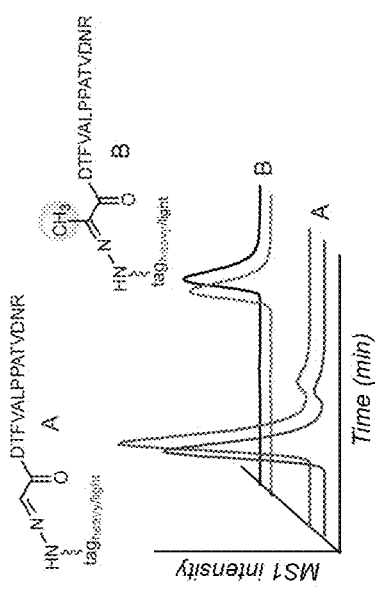
FIG. 13C
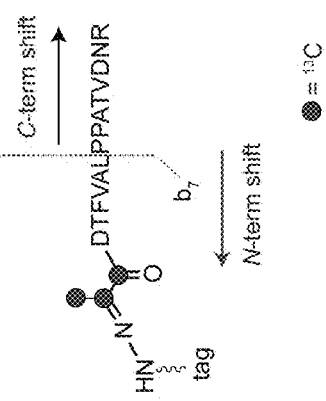

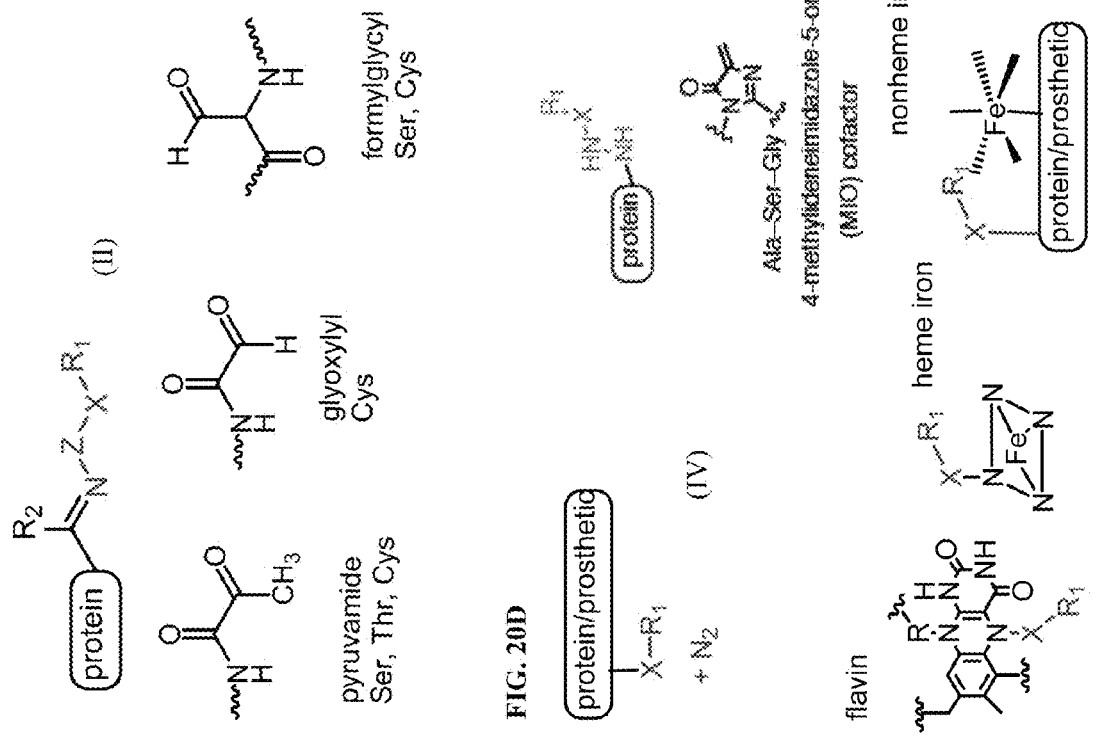
FIG. 20A
FIG. 20B
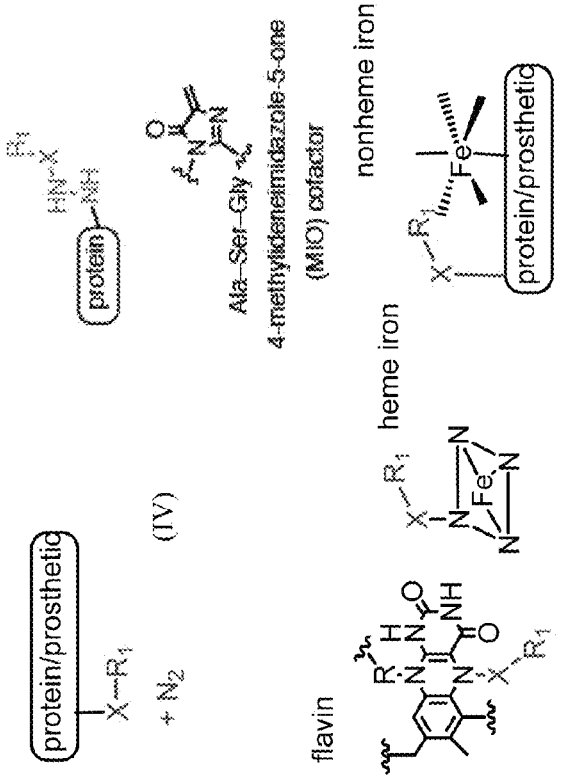
FIG. 20C
FIG. 20D
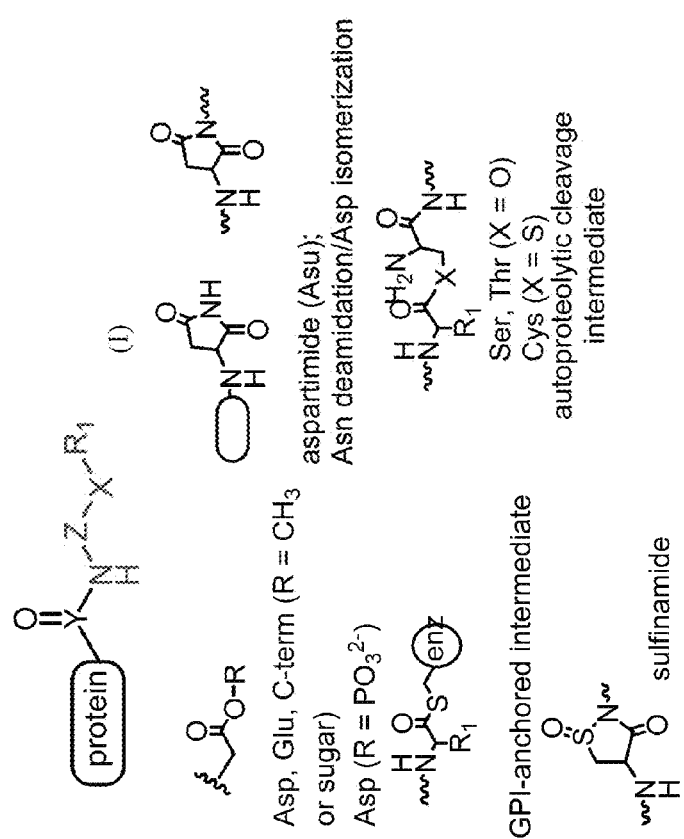

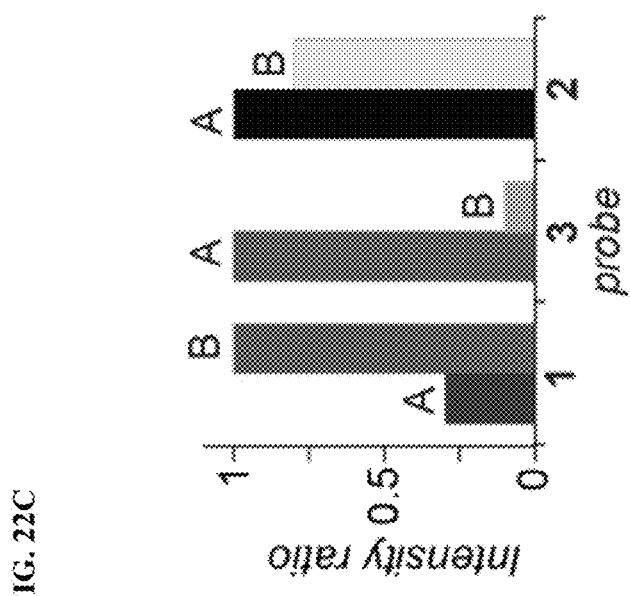
FIG. 22B
FIG. 22C
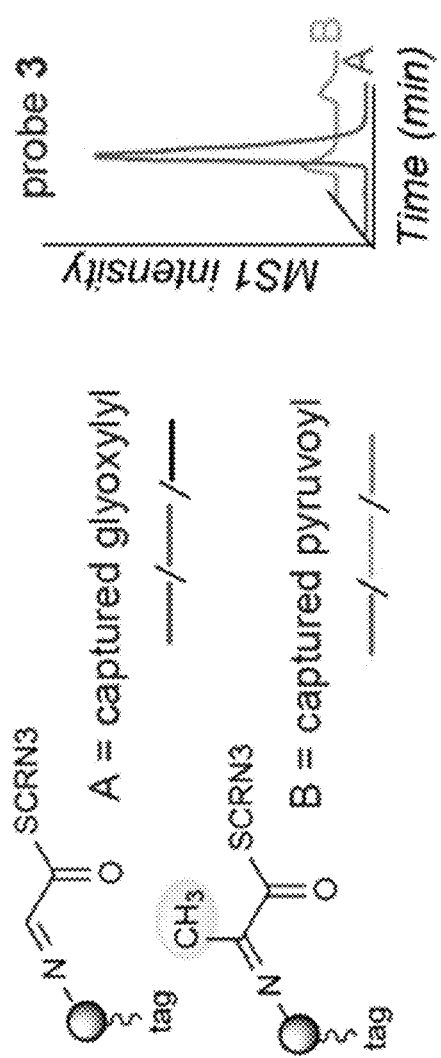
FIG. 22A

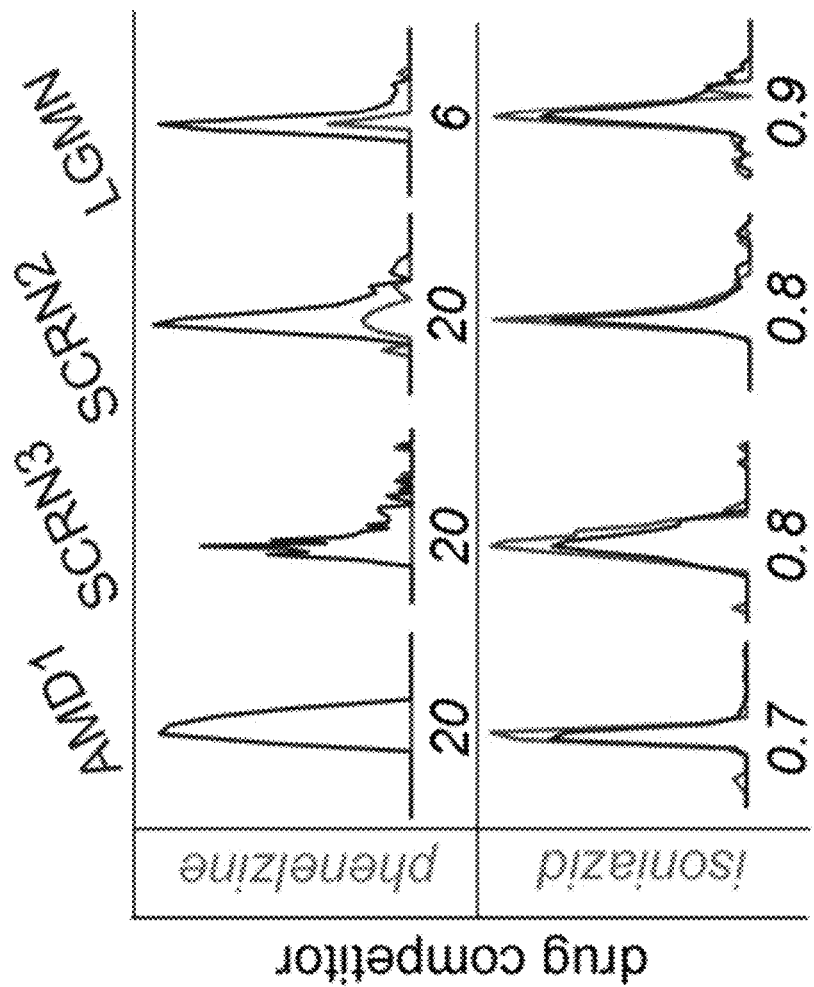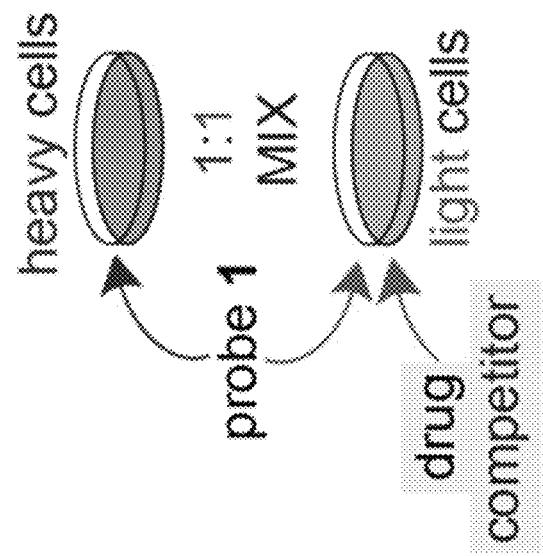
FIG. 25

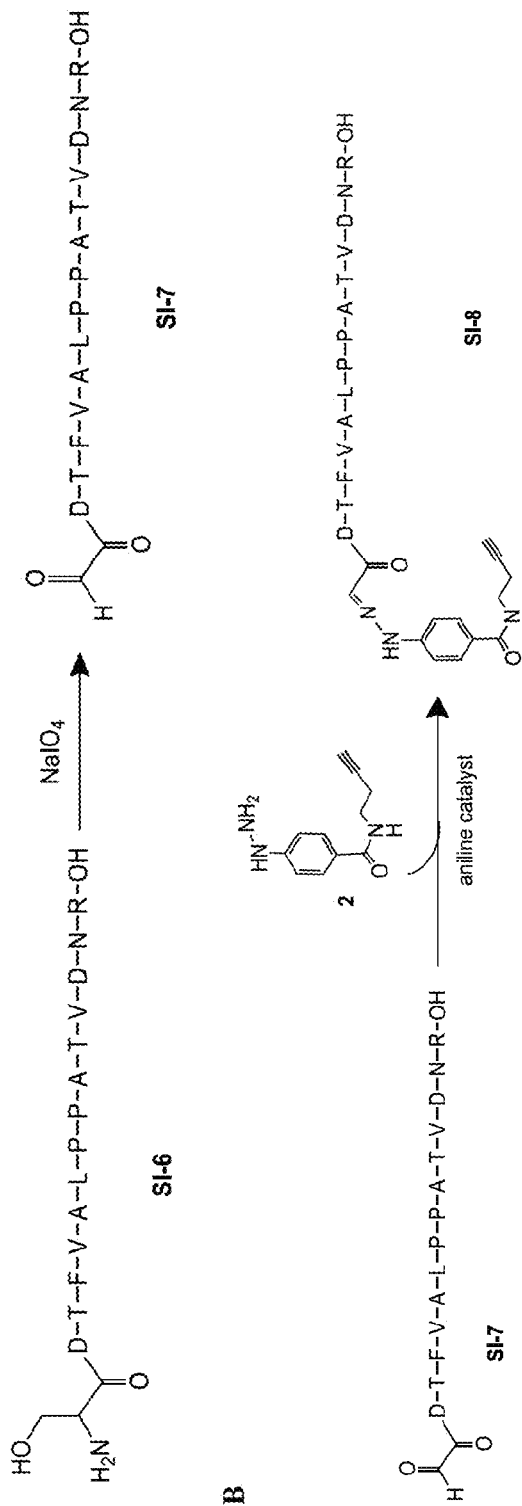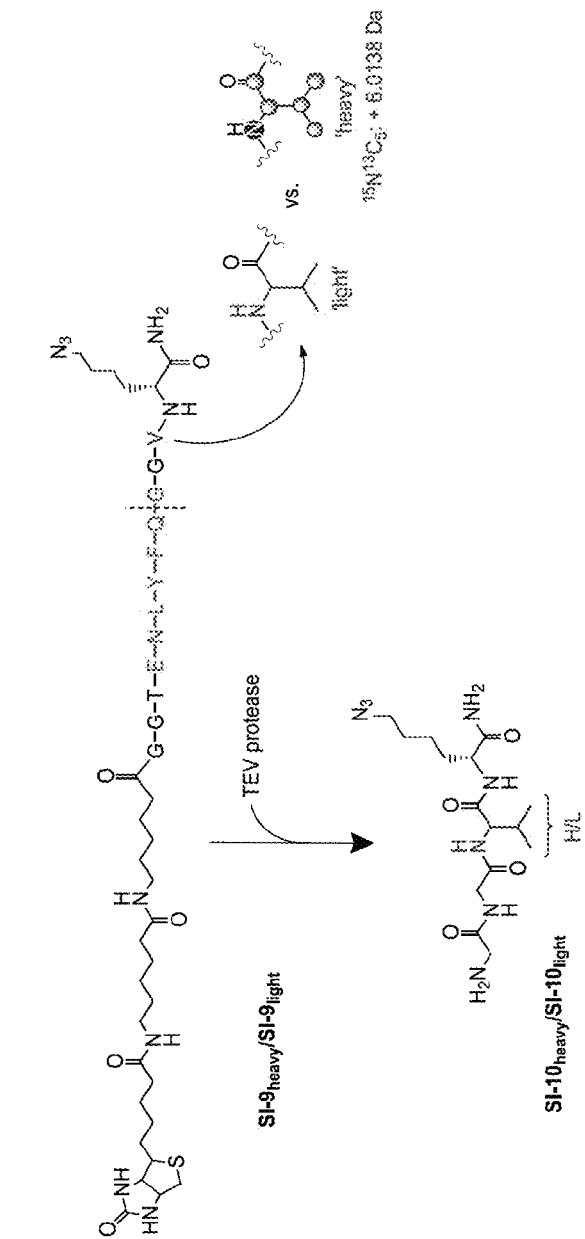
FIG. 26A
FIG. 26B
FIG. 26C

```
                      SEQUENCE LISTING

<160> NUMBER OF SEQ ID NOS: 69

<210> SEQ ID NO 1
<211> LENGTH: 6
<212> TYPE: PRT
<213> ORGANISM: Artificial Sequence
<220> FEATURE:
<223> OTHER INFORMATION: N-terminal pyruvoyl peptide of AMD1 labelled by
      probe 1
<220> FEATURE:
<221> NAME/KEY: MOD_RES
<222> LOCATION: (1)..(1)
<223> OTHER INFORMATION: pyruvoyl modification labeled with probe 1

<400> SEQUENCE: 1

Ser Met Phe Val Ser Lys
1               5

<210> SEQ ID NO 2
<211> LENGTH: 7
<212> TYPE: PRT
```

```
<213> ORGANISM: Artificial Sequence
<220> FEATURE:
<223> OTHER INFORMATION: alanine form of N-terminal AMD1 peptide

<400> SEQUENCE: 2

Ala Ser Met Phe Val Ser Lys
1               5

<210> SEQ ID NO 3
<211> LENGTH: 12
<212> TYPE: PRT
<213> ORGANISM: Artificial Sequence
<220> FEATURE:
<223> OTHER INFORMATION: internal AMD1 peptide

<400> SEQUENCE: 3

Phe Val Thr Thr Leu Phe Val Asn Gln Ser Ser Lys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: unlabelled pyruvoyl-containing tryptic peptide
      from AMD1
<220> FEATURE:
<221> NAME/KEY: MOD_RES
<222> LOCATION: (1)..(1)
<223> OTHER INFORMATION: pyruvoyl modification

<400> SEQUENCE: 4

Ser Met Phe Val Ser Lys
1               5

<210> SEQ ID NO 5
<211> LENGTH: 345
<212> TYPE: PRT
<213> ORGANISM: Artificial Sequence
<220> FEATURE:
<223> OTHER INFORMATION: full length AMD1 with 12 amino acids (MRGSH6GS)
      appended to N-terminal methionine

<400> SEQUENCE: 5

Met Arg Gly Ser His His His His His His Gly Ser Glu Ala Ala His
1               5                   10                  15

Phe Phe Glu Gly Thr Glu Lys Leu Leu Glu Val Trp Phe Ser Arg Gln
                20                  25                  30

Gln Pro Asp Ala Asn Gln Gly Ser Gly Asp Leu Arg Thr Ile Pro Arg
            35                  40                  45

Ser Glu Trp Asp Ile Leu Leu Lys Asp Val Gln Cys Ser Ile Ile Ser
        50                  55                  60

Val Thr Lys Thr Asp Lys Gln Glu Ala Tyr Val Leu Ser Glu Ser Ser
65                  70                  75                  80

Met Phe Val Ser Lys Arg Arg Phe Ile Leu Lys Thr Cys Gly Thr Thr
                85                  90                  95

Leu Leu Leu Lys Ala Leu Val Pro Leu Leu Lys Leu Ala Arg Asp Tyr
                100                 105                 110

Ser Gly Phe Asp Ser Ile Gln Ser Phe Tyr Ser Arg Lys Asn Phe
                115                 120                 125

Met Lys Pro Ser His Gln Gly Tyr Pro His Arg Asn Phe Gln Glu Glu
                130                 135                 140

Ile Glu Phe Leu Asn Ala Ile Phe Pro Asn Gly Ala Ala Tyr Cys Met
```

```
             145                 150                 155                 160
Gly Arg Met Asn Ser Asp Cys Trp Tyr Leu Tyr Thr Leu Asp Phe Pro
                    165                 170                 175
Glu Ser Arg Val Ile Ser Gln Pro Asp Gln Thr Leu Glu Ile Leu Met
                180                 185                 190
Ser Glu Leu Asp Pro Ala Val Met Asp Gln Phe Tyr Met Lys Asp Gly
            195                 200                 205
Val Thr Ala Lys Asp Val Thr Arg Glu Ser Gly Ile Arg Asp Leu Ile
    210                 215                 220
Pro Gly Ser Val Ile Asp Ala Thr Met Phe Asn Pro Cys Gly Tyr Ser
225                 230                 235                 240
Met Asn Gly Met Lys Ser Asp Gly Thr Tyr Trp Thr Ile His Ile Thr
                245                 250                 255
Pro Glu Pro Glu Phe Ser Tyr Val Ser Phe Glu Thr Asn Leu Ser Gln
                260                 265                 270
Thr Ser Tyr Asp Asp Leu Ile Arg Lys Val Val Glu Val Phe Lys Pro
            275                 280                 285
Gly Lys Phe Val Thr Thr Leu Phe Val Asn Gln Ser Ser Lys Cys Arg
    290                 295                 300
Thr Val Leu Ala Ser Pro Gln Lys Ile Glu Gly Phe Lys Arg Leu Asp
305                 310                 315                 320
Cys Gln Ser Ala Met Phe Asn Asp Tyr Asn Phe Val Phe Thr Ser Phe
                325                 330                 335
Ala Lys Lys Gln Gln Gln Gln Ser
                340                 345

<210> SEQ ID NO 6
<211> LENGTH: 8
<212> TYPE: PRT
<213> ORGANISM: Artificial Sequence
<220> FEATURE:
<223> OTHER INFORMATION: tryptic peptide of AMD1

<400> SEQUENCE: 6

Leu Leu Glu Val Trp Phe Ser Arg
1               5

<210> SEQ ID NO 7
<211> LENGTH: 9
<212> TYPE: PRT
<213> ORGANISM: Artificial Sequence
<220> FEATURE:
<223> OTHER INFORMATION: tryptic peptide of AMD1

<400> SEQUENCE: 7

Thr Cys Gly Thr Thr Leu Leu Leu Lys
1               5

<210> SEQ ID NO 8
<211> LENGTH: 17
<212> TYPE: PRT
<213> ORGANISM: Artificial Sequence
<220> FEATURE:
<223> OTHER INFORMATION: tryptic peptide of AMD1

<400> SEQUENCE: 8

Met Asn Ser Asp Cys Trp Tyr Leu Tyr Thr Leu Asp Phe Pro Glu Ser
1               5                   10                  15

Arg
```

```
<210> SEQ ID NO 9
<211> LENGTH: 10
<212> TYPE: PRT
<213> ORGANISM: Artificial Sequence
<220> FEATURE:
<223> OTHER INFORMATION: tryptic peptide of AMD1

<400> SEQUENCE: 9

Lys Val Val Glu Val Phe Lys Pro Gly Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: tryptic peptide of AMD1

<400> SEQUENCE: 10

Gln Gln Pro Asp Ala Asn Gln Gly Ser Gly Asp Leu Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: tryptic peptide of AMD1

<400> SEQUENCE: 11

Asp Tyr Ser Gly Phe Asp Ser Ile Gln Ser Phe Phe Tyr Ser Arg
1               5                   10                  15

<210> SEQ ID NO 12
<211> LENGTH: 27
<212> TYPE: PRT
<213> ORGANISM: Artificial Sequence
<220> FEATURE:
<223> OTHER INFORMATION: tryptic peptide of AMD1

<400> SEQUENCE: 12

Val Ile Ser Gln Pro Asp Gln Thr Leu Glu Ile Leu Met Ser Glu Leu
1               5                   10                  15

Asp Pro Ala Val Met Asp Gln Phe Tyr Met Lys
            20                  25

<210> SEQ ID NO 13
<211> LENGTH: 12
<212> TYPE: PRT
<213> ORGANISM: Artificial Sequence
<220> FEATURE:
<223> OTHER INFORMATION: tryptic peptide of AMD1

<400> SEQUENCE: 13

Phe Val Thr Thr Leu Phe Val Asn Gln Ser Ser Lys
1               5                   10

<210> SEQ ID NO 14
<211> LENGTH: 8
<212> TYPE: PRT
<213> ORGANISM: Artificial Sequence
<220> FEATURE:
<223> OTHER INFORMATION: tryptic peptide of AMD1

<400> SEQUENCE: 14

Ser Glu Trp Asp Ile Leu Leu Lys
```

```
<210> SEQ ID NO 15
<211> LENGTH: 14
<212> TYPE: PRT
<213> ORGANISM: Artificial Sequence
<220> FEATURE:
<223> OTHER INFORMATION: tryptic peptide of AMD1

<400> SEQUENCE: 15

Lys Asn Phe Met Lys Pro Ser His Gln Gly Tyr Pro His Arg
1               5                   10

<210> SEQ ID NO 16
<211> LENGTH: 29
<212> TYPE: PRT
<213> ORGANISM: Artificial Sequence
<220> FEATURE:
<223> OTHER INFORMATION: tryptic peptide of AMD1

<400> SEQUENCE: 16

Glu Ser Gly Ile Arg Asp Leu Ile Pro Gly Ser Val Ile Asp Ala Thr
1               5                   10                  15

Met Phe Asn Pro Cys Gly Tyr Ser Met Asn Gly Met Lys
            20                  25

<210> SEQ ID NO 17
<211> LENGTH: 8
<212> TYPE: PRT
<213> ORGANISM: Artificial Sequence
<220> FEATURE:
<223> OTHER INFORMATION: tryptic peptide of AMD1

<400> SEQUENCE: 17

Thr Val Leu Ala Ser Pro Gln Lys
1               5

<210> SEQ ID NO 18
<211> LENGTH: 11
<212> TYPE: PRT
<213> ORGANISM: Artificial Sequence
<220> FEATURE:
<223> OTHER INFORMATION: tryptic peptide of AMD1

<400> SEQUENCE: 18

Asp Val Gln Cys Ser Ile Ile Ser Val Thr Lys
1               5                   10

<210> SEQ ID NO 19
<211> LENGTH: 23
<212> TYPE: PRT
<213> ORGANISM: Artificial Sequence
<220> FEATURE:
<223> OTHER INFORMATION: tryptic peptide of AMD1

<400> SEQUENCE: 19

Asn Phe Gln Glu Glu Ile Glu Phe Leu Asn Ala Ile Phe Pro Asn Gly
1               5                   10                  15

Ala Ala Tyr Cys Met Gly Arg
            20

<210> SEQ ID NO 20
<211> LENGTH: 35
<212> TYPE: PRT
<213> ORGANISM: Artificial Sequence
<220> FEATURE:
```

```
<223> OTHER INFORMATION: tryptic peptide of AMD1

<400> SEQUENCE: 20

Ser Asp Gly Thr Tyr Trp Thr Ile His Ile Thr Pro Glu Pro Glu Phe
1               5                   10                  15
Ser Tyr Val Ser Phe Glu Thr Asn Leu Ser Gln Thr Ser Tyr Asp Asp
            20                  25                  30
Leu Ile Arg
        35

<210> SEQ ID NO 21
<211> LENGTH: 21
<212> TYPE: PRT
<213> ORGANISM: Artificial Sequence
<220> FEATURE:
<223> OTHER INFORMATION: tryptic peptide of AMD1

<400> SEQUENCE: 21

Arg Leu Asp Cys Gln Ser Ala Met Phe Asn Asp Tyr Asn Phe Val Phe
1               5                   10                  15
Thr Ser Phe Ala Lys
            20

<210> SEQ ID NO 22
<211> LENGTH: 20
<212> TYPE: PRT
<213> ORGANISM: Artificial Sequence
<220> FEATURE:
<223> OTHER INFORMATION: N-terminal sequence of SCRN3

<400> SEQUENCE: 22

Met Glu Pro Phe Ser Cys Asp Thr Phe Val Ala Leu Pro Pro Ala Thr
1               5                   10                  15
Val Asp Asn Arg
            20

<210> SEQ ID NO 23
<211> LENGTH: 26
<212> TYPE: PRT
<213> ORGANISM: Artificial Sequence
<220> FEATURE:
<223> OTHER INFORMATION: N-terminal sequence of SCRN2

<400> SEQUENCE: 23

Met Ala Ser Ser Ser Pro Asp Ser Pro Cys Ser Cys Asp Cys Phe Val
1               5                   10                  15
Ser Val Pro Pro Ala Ser Ala Ile Pro Ala
            20                  25

<210> SEQ ID NO 24
<211> LENGTH: 21
<212> TYPE: PRT
<213> ORGANISM: Artificial Sequence
<220> FEATURE:
<223> OTHER INFORMATION: N-terminal sequence of SCRN1

<400> SEQUENCE: 24

Met Ala Ala Ala Pro Pro Ser Tyr Cys Phe Val Ala Phe Pro Pro Arg
1               5                   10                  15
Ala Lys Asp Gly Leu
            20

<210> SEQ ID NO 25
```

```
<211> LENGTH: 15
<212> TYPE: PRT
<213> ORGANISM: Artificial Sequence
<220> FEATURE:
<223> OTHER INFORMATION: SCRN3 peptide

<400> SEQUENCE: 25

Cys Asp Thr Phe Val Ala Leu Pro Pro Ala Thr Val Asp Asn Arg
1               5                   10                  15

<210> SEQ ID NO 26
<211> LENGTH: 6
<212> TYPE: PRT
<213> ORGANISM: Artificial Sequence
<220> FEATURE:
<223> OTHER INFORMATION: AMD1 pyruvoyl peptide labelled by probe 1 and
      TEV tag
<220> FEATURE:
<221> NAME/KEY: MOD_RES
<222> LOCATION: (1)..(1)
<223> OTHER INFORMATION: pyruvoyl modification labelled by probe 1
      conjugated to heavy/light TEV tag via triazole linker

<400> SEQUENCE: 26

Ser Met Phe Val Ser Lys
1               5

<210> SEQ ID NO 27
<211> LENGTH: 6
<212> TYPE: PRT
<213> ORGANISM: Artificial Sequence
<220> FEATURE:
<223> OTHER INFORMATION: AMD1 pyruvoyl peptide labelled by probe 2 and
      TEV tag
<220> FEATURE:
<221> NAME/KEY: MOD_RES
<222> LOCATION: (1)..(1)
<223> OTHER INFORMATION: pyruvoyl modification labelled by probe 2
      conjugated to heavy/light TEV tag via triazole linker

<400> SEQUENCE: 27

Ser Met Phe Val Ser Lys
1               5

<210> SEQ ID NO 28
<211> LENGTH: 14
<212> TYPE: PRT
<213> ORGANISM: Artificial Sequence
<220> FEATURE:
<223> OTHER INFORMATION: SCRN3 peptide labelled with probe 2 and
      heavy/light tag
<220> FEATURE:
<221> NAME/KEY: MOD_RES
<222> LOCATION: (1)..(1)
<223> OTHER INFORMATION: glyoxyl group labelled with probe 2 linked to
      heavy/light tag

<400> SEQUENCE: 28

Asp Thr Phe Val Ala Leu Pro Pro Ala Thr Val Asp Asn Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: SCRN3 peptide labelled with probe 1 and
      heavy/light tag
<220> FEATURE:
<221> NAME/KEY: MOD_RES
<222> LOCATION: (1)..(1)
```

```
<223> OTHER INFORMATION: glyoxyl group labelled with probe 1 conjugated
      to heavy/light TEV tag via triazole linker

<400> SEQUENCE: 29

Asp Thr Phe Val Ala Leu Pro Pro Ala Thr Val Asp Asn Arg
1               5                   10

<210> SEQ ID NO 30
<211> LENGTH: 15
<212> TYPE: PRT
<213> ORGANISM: Artificial Sequence
<220> FEATURE:
<223> OTHER INFORMATION: SCRN3 peptide with glycine N-terminus produced
      by reductive amination

<400> SEQUENCE: 30

Gly Asp Thr Phe Val Ala Leu Pro Pro Ala Thr Val Asp Asn Arg
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: SCRN3 peptide labelled with probe 2 and
      heavy/light tag
<220> FEATURE:
<221> NAME/KEY: MOD_RES
<222> LOCATION: (1)..(1)
<223> OTHER INFORMATION: pyruvoyl group labelled with probe 2 linked to
      heavy/light tag

<400> SEQUENCE: 31

Asp Thr Phe Val Ala Leu Pro Pro Ala Thr Val Asp Asn Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: probe 2 labelled glyoxyl-modified SCRN3 peptide
<220> FEATURE:
<221> NAME/KEY: MOD_RES
<222> LOCATION: (1)..(1)
<223> OTHER INFORMATION: glyoxyl group labelled with probe 2

<400> SEQUENCE: 32

Asp Thr Phe Val Ala Leu Pro Pro Ala Thr Val Asp Asn Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: arylamine N-terminal SCRN3 peptide
<220> FEATURE:
<221> NAME/KEY: MOD_RES
<222> LOCATION: (1)..(1)
<223> OTHER INFORMATION: arylamine modification

<400> SEQUENCE: 33

Asp Thr Phe Val Ala Leu Pro Pro Ala Thr Val Asp Asn Arg
1               5                   10

<210> SEQ ID NO 34
<211> LENGTH: 11
<212> TYPE: PRT
```

```
<213> ORGANISM: Artificial Sequence
<220> FEATURE:
<223> OTHER INFORMATION: heavy/light SCRN3 internal peptide

<400> SEQUENCE: 34

Ala Leu Asn Val Ile Val Asp Leu Leu Glu Lys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: heavy/light unmodified SCRN3 peptide standard
<220> FEATURE:
<221> NAME/KEY: MOD_RES
<222> LOCATION: (1)..(1)
<223> OTHER INFORMATION: cysteine side chain alkylated with -CH2C(O)NH2

<400> SEQUENCE: 35

Cys Asp Thr Phe Val Ala Leu Pro Pro Ala Thr Val Asp Asn Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: SI-6 peptide

<400> SEQUENCE: 36

Ser Asp Thr Phe Val Ala Leu Pro Pro Ala Thr Val Asp Asn Arg
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: glyoxyl6-Arg20 peptide SI-7
<220> FEATURE:
<221> NAME/KEY: MOD_RES
<222> LOCATION: (1)..(1)
<223> OTHER INFORMATION: glyoxyl modification

<400> SEQUENCE: 37

Asp Thr Phe Val Ala Leu Pro Pro Ala Thr Val Asp Asn Arg
1               5                   10

<210> SEQ ID NO 38
<211> LENGTH: 14
<212> TYPE: PRT
<213> ORGANISM: Artificial Sequence
<220> FEATURE:
<223> OTHER INFORMATION: probe 2-labelled glyoxyl6-Arg20 peptide SI-8
<220> FEATURE:
<221> NAME/KEY: MOD_RES
<222> LOCATION: (1)..(1)
<223> OTHER INFORMATION: glyoxyl modification labelled with probe 2

<400> SEQUENCE: 38

Asp Thr Phe Val Ala Leu Pro Pro Ala Thr Val Asp Asn Arg
1               5                   10

<210> SEQ ID NO 39
<211> LENGTH: 13
<212> TYPE: PRT
<213> ORGANISM: Artificial Sequence
<220> FEATURE:
```

```
<223> OTHER INFORMATION: biotin-azide tags SI-9heavy/SI-9light
<220> FEATURE:
<221> NAME/KEY: MOD_RES
<222> LOCATION: (1)..(1)
<223> OTHER INFORMATION: modified by linker attached to biotin
<220> FEATURE:
<221> NAME/KEY: MOD_RES
<222> LOCATION: (13)..(13)
<223> OTHER INFORMATION: lysine(azide) residue (Lys(N3))
<220> FEATURE:
<221> NAME/KEY: MOD_RES
<222> LOCATION: (13)..(13)
<223> OTHER INFORMATION: AMIDATION

<400> SEQUENCE: 39

Gly Gly Thr Glu Asn Leu Tyr Phe Gln Gly Gly Val Lys
1               5                   10

<210> SEQ ID NO 40
<211> LENGTH: 4
<212> TYPE: PRT
<213> ORGANISM: Artificial Sequence
<220> FEATURE:
<223> OTHER INFORMATION: isotopic protease cleaved azide tag
      SI-10heavy/SI-10light
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: lysine(azide) residue (Lys(N3))

<400> SEQUENCE: 40

Gly Gly Val Lys
1

<210> SEQ ID NO 41
<211> LENGTH: 14
<212> TYPE: PRT
<213> ORGANISM: Artificial Sequence
<220> FEATURE:
<223> OTHER INFORMATION: probe 2-labelled glyoxyl6-Arg20 peptide
      SI-11heavy/SI-11light
<220> FEATURE:
<221> NAME/KEY: MOD_RES
<222> LOCATION: (1)..(1)
<223> OTHER INFORMATION: glyoxyl group labeled with probe 2 conjugated
      to heavy/light TEV tage via triazole linker

<400> SEQUENCE: 41

Asp Thr Phe Val Ala Leu Pro Pro Ala Thr Val Asp Asn Arg
1               5                   10

<210> SEQ ID NO 42
<211> LENGTH: 8
<212> TYPE: PRT
<213> ORGANISM: Artificial Sequence
<220> FEATURE:
<223> OTHER INFORMATION: FLAG tag

<400> SEQUENCE: 42

Asp Tyr Lys Asp Asp Asp Asp Lys
1               5

<210> SEQ ID NO 43
<211> LENGTH: 15
<212> TYPE: PRT
<213> ORGANISM: Artificial Sequence
<220> FEATURE:
```

<223> OTHER INFORMATION: additional N-terminal amino acid sequence

<400> SEQUENCE: 43

Met Asp Tyr Lys Asp Asp Asp Lys Leu Lys Ala Cys Gly Arg
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: additional C-terminal amino acid sequence

<400> SEQUENCE: 44

Ala Ala Ala Gly Gly Gly Gly Asp Tyr Lys Asp Asp Asp Lys
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: N-terminal residues Met1 to Cys6 of SCRN3

<400> SEQUENCE: 45

Met Glu Pro Phe Ser Cys
1               5

<210> SEQ ID NO 46
<211> LENGTH: 12
<212> TYPE: PRT
<213> ORGANISM: Artificial Sequence
<220> FEATURE:
<223> OTHER INFORMATION: additional amino acids appended to N-terminal
      Met of AMD1

<400> SEQUENCE: 46

Met Arg Gly Ser His His His His His His Gly Ser
1               5                   10

<210> SEQ ID NO 47
<211> LENGTH: 22
<212> TYPE: PRT
<213> ORGANISM: Artificial Sequence
<220> FEATURE:
<223> OTHER INFORMATION: (FLAG)3 peptide

<400> SEQUENCE: 47

Asp Tyr Lys Asp His Asp Gly Asp Tyr Lys His Asp Ile Asp Tyr
1               5                   10                  15

Lys Asp Asp Asp Asp Lys
            20

<210> SEQ ID NO 48
<211> LENGTH: 11
<212> TYPE: PRT
<213> ORGANISM: Artificial Sequence
<220> FEATURE:
<223> OTHER INFORMATION: additional sequence added to C-terminus of
      SCRN3

<400> SEQUENCE: 48

Ala Ala Ala Leu Glu His His His His His His
1               5                   10

<210> SEQ ID NO 49

```
<211> LENGTH: 20
<212> TYPE: PRT
<213> ORGANISM: Artificial Sequence
<220> FEATURE:
<223> OTHER INFORMATION: SCRN3 peptide

<400> SEQUENCE: 49

Met Glu Pro Phe Ser Cys Asp Thr Phe Val Ala Leu Pro Pro Ala Thr
1               5                   10                  15

Val Asp Asn Arg
            20

<210> SEQ ID NO 50
<211> LENGTH: 16
<212> TYPE: PRT
<213> ORGANISM: Artificial Sequence
<220> FEATURE:
<223> OTHER INFORMATION: SCRN3 peptide

<400> SEQUENCE: 50

Ser Cys Asp Thr Phe Val Ala Leu Pro Pro Ala Thr Val Asp Asn Arg
1               5                   10                  15

<210> SEQ ID NO 51
<211> LENGTH: 14
<212> TYPE: PRT
<213> ORGANISM: Artificial Sequence
<220> FEATURE:
<223> OTHER INFORMATION: SCRN3 peptide

<400> SEQUENCE: 51

Asp Thr Phe Val Ala Leu Pro Pro Ala Thr Val Asp Asn Arg
1               5                   10

<210> SEQ ID NO 52
<211> LENGTH: 21
<212> TYPE: PRT
<213> ORGANISM: Artificial Sequence
<220> FEATURE:
<223> OTHER INFORMATION: SCRN3 peptide

<400> SEQUENCE: 52

Lys Cys Thr Tyr Ile Glu Ile Asp Gln Val Pro Glu Thr Tyr Ala Val
1               5                   10                  15

Val Leu Ser Arg Pro
            20

<210> SEQ ID NO 53
<211> LENGTH: 18
<212> TYPE: PRT
<213> ORGANISM: Artificial Sequence
<220> FEATURE:
<223> OTHER INFORMATION: SCRN3 peptide

<400> SEQUENCE: 53

Arg Glu Glu Val Cys Asp Glu Glu Ala Leu Leu Gly Met Asp Leu Val
1               5                   10                  15

Arg Leu

<210> SEQ ID NO 54
<211> LENGTH: 12
<212> TYPE: PRT
<213> ORGANISM: Artificial Sequence
<220> FEATURE:
<223> OTHER INFORMATION: SCRN3 peptide
```

```
<400> SEQUENCE: 54

Lys Ile Val Asn Leu Phe Pro Gln Cys Thr Lys Asp
1               5                   10

<210> SEQ ID NO 55
<211> LENGTH: 13
<212> TYPE: PRT
<213> ORGANISM: Artificial Sequence
<220> FEATURE:
<223> OTHER INFORMATION: SCRN3 peptide

<400> SEQUENCE: 55

Lys Tyr Gly Gln Gly Gly Asn Cys Thr Glu Gly Arg Met
1               5                   10

<210> SEQ ID NO 56
<211> LENGTH: 13
<212> TYPE: PRT
<213> ORGANISM: Artificial Sequence
<220> FEATURE:
<223> OTHER INFORMATION: SCRN3 peptide

<400> SEQUENCE: 56

Lys Ala Leu Asn Val Ile Val Asp Leu Leu Glu Lys Tyr
1               5                   10

<210> SEQ ID NO 57
<211> LENGTH: 17
<212> TYPE: PRT
<213> ORGANISM: Artificial Sequence
<220> FEATURE:
<223> OTHER INFORMATION: SCRN3 peptide

<400> SEQUENCE: 57

Lys Glu Phe Asp Phe Ala Ala Ala Tyr Ser Tyr Leu Asp Thr Ala Lys
1               5                   10                  15

Met

<210> SEQ ID NO 58
<211> LENGTH: 10
<212> TYPE: PRT
<213> ORGANISM: Artificial Sequence
<220> FEATURE:
<223> OTHER INFORMATION: SCRN3 peptide

<400> SEQUENCE: 58

Lys Lys Ser His Phe Lys Pro Asp Arg Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: SCRN3 peptide

<400> SEQUENCE: 59

Arg Asn Ile Ser Asn Gln Leu Ser Ile Thr Thr Lys Ile
1               5                   10

<210> SEQ ID NO 60
<211> LENGTH: 15
<212> TYPE: PRT
<213> ORGANISM: Artificial Sequence
<220> FEATURE:
<223> OTHER INFORMATION: SCRN3 peptide
```

```
<400> SEQUENCE: 60

Lys Asp Glu Ile Gln Ile Tyr Gln Ser Asn Leu Ser Val Lys Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: SCRN3 peptide

<400> SEQUENCE: 61

Lys Gly Asn Ile Thr Phe Glu Thr Met Met Glu Ile Leu Arg Asp
1               5                   10                  15

<210> SEQ ID NO 62
<211> LENGTH: 13
<212> TYPE: PRT
<213> ORGANISM: Artificial Sequence
<220> FEATURE:
<223> OTHER INFORMATION: SCRN3 peptide

<400> SEQUENCE: 62

Arg Asn Glu Ala Trp Ile Leu Glu Thr Ala Gly Lys Tyr
1               5                   10

<210> SEQ ID NO 63
<211> LENGTH: 16
<212> TYPE: PRT
<213> ORGANISM: Artificial Sequence
<220> FEATURE:
<223> OTHER INFORMATION: SCRN3 peptide

<400> SEQUENCE: 63

Lys His Gln Gln Ala Leu Glu Val Val Asn Asn Glu Glu Lys Ala
1               5                   10                  15

<210> SEQ ID NO 64
<211> LENGTH: 21
<212> TYPE: PRT
<213> ORGANISM: Artificial Sequence
<220> FEATURE:
<223> OTHER INFORMATION: SCRN3 peptide

<400> SEQUENCE: 64

His Ile Ser Gln Leu Leu Asp Thr Ser Ser Pro Thr Phe Glu Leu Glu
1               5                   10                  15

Asp Leu Val Lys Lys
            20

<210> SEQ ID NO 65
<211> LENGTH: 9
<212> TYPE: PRT
<213> ORGANISM: Artificial Sequence
<220> FEATURE:
<223> OTHER INFORMATION: SCRN3 peptide

<400> SEQUENCE: 65

Arg Arg His Pro Leu Tyr Gln Lys His
1               5

<210> SEQ ID NO 66
<211> LENGTH: 9
<212> TYPE: PRT
<213> ORGANISM: Artificial Sequence
```

```
<220> FEATURE:
<223> OTHER INFORMATION: SCRN3 peptide

<400> SEQUENCE: 66

Lys Ile Met Leu Asp Asn Met Arg Lys
1               5

<210> SEQ ID NO 67
<211> LENGTH: 11
<212> TYPE: PRT
<213> ORGANISM: Artificial Sequence
<220> FEATURE:
<223> OTHER INFORMATION: SCRN3 peptide

<400> SEQUENCE: 67

Arg Met Val Phe Ser Tyr His Asn Ser Phe Leu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: SCRN3 peptide

<400> SEQUENCE: 68

Lys Ser His Phe Lys Pro Asp Arg Arg His
1               5                   10

<210> SEQ ID NO 69
<211> LENGTH: 6
<212> TYPE: PRT
<213> ORGANISM: Artificial Sequence
<220> FEATURE:
<223> OTHER INFORMATION: 6x-His Tag

<400> SEQUENCE: 69

His His His His His His
1               5
```

CHEMOPROTEOMIC PROFILING OF PROTEIN ELECTROPHILIC AND OXIDATIVE POST-TRANSLATIONAL MODIFICATIONS

CROSS REFERENCE TO RELATED APPLICATION

This application is entitled to priority pursuant to 35 U.S.C. § 119(e) to U.S. Provisional Patent Application No. 62/579,497, filed Oct. 31, 2017, which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with file name "689270-1 Sequence Listing," creation date of Jan. 17, 2019 and having a size of 21.7 KB. The sequence listing submitted via EFS-Web is part of the specification and is herein incorporated by reference in its entirety.

BACKGROUND OF THE INVENTION

Post-translational modifications (PTMs) serve to diversify protein structure and function in important ways, including, but not limited to, the regulation of protein activity, protein-protein interactions, and protein localization and stability in cells[1]. Proteins are subject to a wide array of chemically diverse PTMs, which have historically been discovered on a case-by-case basis by in-depth investigations of individual proteins[2]. Advances in mass spectrometry (MS) technologies have, however, made it possible to discover novel PTMs with improved scope, sensitivity, and structural resolution, leading to an expanded understanding of diverse modification states, such as the N-acetylation/acylation of lysines[3] and electrophilic/oxidative modification of cysteines[4,5]. It is likely, however, that many functionally important PTMs remain to be discovered because they are, as-of-yet, structurally unpredicted and/or occur on proteins of unknown function[3].

Various approaches have been used to discover and characterize PTMs, including exploiting their often atypical chemical reactivity for covalent tagging and enrichment[6-8]. For example, activity-based protein profiling (ABPP) is an approach used to discover and characterize functional amino acids in proteins on the basis of their enhanced reactivity towards small-molecule probes. ABPP uses chemical probes that react with large classes of proteins based on shared functional and/or structural properties[9]. Such atypical chemical 'reactivity' can originate from conserved amino acid residues that confer special activities to proteins, such as enzymatic catalysis, and, accordingly, ABPP has been applied to characterize diverse enzyme classes in native biological systems[9]. However, to date, the ABPP approach has mainly targeted nucleophilic functional groups[10], such as the side chains of serine and cysteine, using electrophilic probes, largely because the main twenty proteinogenic amino acids are replete with nucleophilic side chains, but devoid of reactive electrophiles. Proteins, however, also use electrophilic groups for function, which are typically acquired through installation as covalent PTMs[1,2,11] or by binding of exogenous cofactors[12].

Previous studies have used nucleophilic probes to characterize PTMs such as N-linked glycosylation[13] and ADP-ribosylation[14], but, in these cases, additional chemistry is required (oxidation and exogenous catalysts, respectively) to promote reactions. Nucleophilic probes have also been applied to characterize various protein modifications that are caused by oxidative stress and aging, including direct oxidation of amino acids (e.g., cysteine sulfenylation[15]; protein carbonylation[16]) and aspartyl and asparaginyl cyclized amino-succinimide modifications[17,18], respectively.

Because electrophilic PTMs and oxidative PTMs can also define reactive centers that are essential for protein function but uncommon and not easily predicted from the primary structures of proteins, additional uncharacterized (not presently known) electrophilic or oxidative sites (sites are PTMs that include but are not limited to amino acid modifications or binding/coordination of other ions or molecules to the protein) may exist in the human proteome. Electrophilic PTMs and oxidative PTMs may serve as biomarkers for certain diseases, or therapeutic targets for treating diseases. For example, monoamine oxidase (MAO) is an enzyme having a flavin cofactor that is targeted by hydrazine drugs (MAOIs). By targeting the flavin cofactor, the activity of MAO is inhibited to provide a therapeutic effect. Discovery and identification of other PTMs on proteins may thus provide new therapeutic targets and biomarkers for disease treatment and diagnosis, e.g., cancer treatment and diagnosis.

BRIEF SUMMARY OF THE INVENTION

Accordingly, there is a need in the art for probes and methods that can be used to discover, identify and characterize electrophiles and oxidative groups installed onto proteins as covalent PTMs or noncovalent PTMs that assist in covalent labeling by the probes. The invention satisfies this need by providing methods for "reverse polarity" (RP)-ABPP using clickable hydrazine probes that can be used to identify functional electrophilic PTMs on proteins in proteomic mixtures, including proteins in living cells (in situ). The inventors surprisingly discovered that by reversing the polarity of activity probes from electrophilic to nucleophilic, ABPP could be used, for example, to identify protein-bound electrophiles, such as those installed as covalent PTMs as well as covalently and non-covalently bound oxidative cofactors, in native biological systems, uncover structurally novel electrophilic PTMs that occur on conserved residues in proteins of uncharacterized function, and reveal dynamic changes in protein-bound electrophile status in response to metabolic perturbations.

In one general aspect, the invention relates to a method for detecting an electrophilic post-translational modification (PTM) or oxidative PTM of at least one protein in a proteomic mixture, the method comprising:
  (i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the at least one protein, thereby forming a mixture comprising at least one alkyne-derivatized protein;
  (ii) labeling the at least one alkyne-derivatized protein with an azide-modified tag, optionally in the presence of a copper catalyst, to obtain at least one labelled protein; and
  (iii) analyzing the at least one labelled protein to thereby detect the PTM of the at least one protein.

In another general aspect, the invention relates to a method for profiling an electrophilic post-translational modification (PTM) or oxidative PTM of at least one protein in a proteomic mixture, the method comprising:
(i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the at least one protein to obtain an alkyne-derivatized protein;
(ii) labeling the alkyne-derivatized protein with an azide-modified tag, optionally in the presence of a copper catalyst, to obtain a labelled protein;
(iii) enriching the labelled protein; and
(iv) quantifying the labelled protein.

In some embodiments, the electrophilic post-translational modification (PTM) is a pyruvoyl modification, glyoxylyl modification, formylglycyl modification, aspartimide (succinimide) modification (internal or C-terminal as in intein chemistry), aspartyl phosphate modification, or quinone modification.

In some embodiments, the oxidative PTM is a Flavin cofactor, quinone cofactor, heme iron cofactor, or non-heme iron cofactor.

In some embodiments, the alkyne moiety of the probe is a terminal alkyne.

In yet another general aspect, the invention relates to a protein conjugate comprising a structure of formula (I), formula (II), formula (III), or formula (IV):

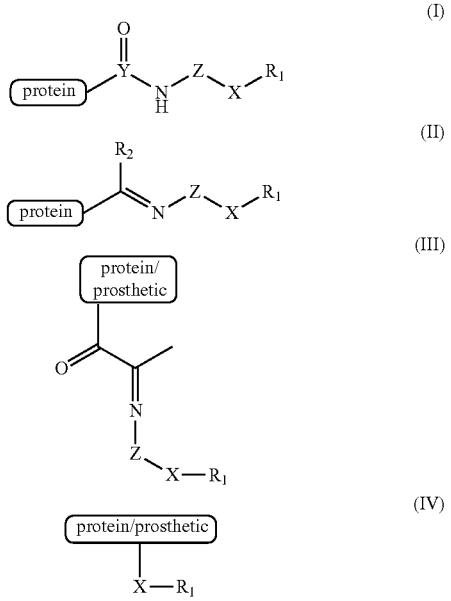

wherein $R_1$ is an alkyne; $R_2$ is hydrogen or alkyl; X is a linker; Y is carbon or sulfur; and Z is NH or oxygen.

In some embodiments, a proteomic mixture or protein conjugate is present in a living cell.

Other general aspects of the invention relate to a composition comprising cells and at least one probe comprising a hydrazine or oxyamine moiety and an alkyne moiety as well as a kit comprising a probe comprising a hydrazine or oxyamine moiety and an alkyne moiety; and an azide-modified tag.

BRIEF DESCRIPTION OF THE FIGURES

The patent or application file contains at least one drawing executed in color. Copies of this patent or patent application publication with color drawing(s) will be provided by the Office upon request and payment of the necessary fee. The foregoing summary, as well as the following detailed description of the invention, will be better understood when read in conjunction with the appended drawings. It should be understood that the invention is not limited to the precise embodiments shown in the drawings.

In the figures:

FIG. 1 shows the structures of clickable reverse polarity (RP)-ABPP hydrazine probes 1 and 2 and the corresponding non-clickable competitor probes 3 and 4; the synthesis of clickable hydrazine probes 1 and 2 is described in Example 1;

FIGS. 2A-2D show SDS-PAGE analysis of hydrazine probe-treated HEK293T cells (30 minutes) as described in Example 2; concentrations, molecular weight markers (left) and exposure intensities (right) are indicated; FIG. 2A shows concentration-dependent labelling profiles for soluble (left) and membrane proteomes (right) of probe 1-treated HEK293T cells (upper) with the corresponding expression profiles (lower); the data demonstrate that labeling of proteins by probe 1 as measured by copper (I)-catalyzed alkyne-azide cycloaddition (CuAAC) to a rhodamine-azide tag is concentration-dependent (fluorescent gel shown in gray-scale); FIG. 2B shows concentration-dependent labelling profiles for soluble (left) and membrane proteomes (right) of probe 2-treated HEK293T cells with the corresponding expression profile (lower);

FIG. 2C shows competition of probe 1 labelling by non-clickable probe 3 for soluble (left) and membrane proteomes (right) of HEK293T cells co-administered with probe 1 and varying concentrations of probe 3 (upper) with the corresponding expression profiles (lower); the data demonstrate that treatment of HEK293T cells with competitor probe 3 blocks the labeling of proteins by probe 1 (3 mM, 30 min) in a concentration-dependent manner; FIG. 2D shows competition of probe 1 versus probe 2 labelling by non-clickable probe 4 for soluble (left) and of probe 2 only for membrane proteomes (right) of HEK293T cells co-administered with probe 1 or probe 2 and varying concentrations of non-clickable probe 4;

FIGS. 3A-3F show identification of protein targets of the hydrazine probes, as described in Example 3; FIG. 3A shows a schematic representation of MS-based quantitative (SILAC) proteomics experiments (enrichment and competition); heavy (H) and light (L) cells, proteomes, and peptides are depicted in blue and red, respectively; FIG. 3B shows a quadrant plot of average competition versus enrichment SILAC ratios from quantitative proteomics experiments (left); probe-1 targeted proteins (upper right quadrant) are highlighted in red and listed to the right of the plot; FIG. 3C shows extracted parent ion chromatograms and corresponding H/L ratios for representative tryptic peptides of three protein targets of probe 1 (AMD1, SCRN3, and LGMN) quantified in enrichment, competition, and probe vs. probe control experiments; FIG. 3D shows Western blots (upper) and RP-ABPP data (lower) for hydrazine probe-treated transfected cells expressing the indicated protein targets (AMD1, SCRN3, KEAP1, or FTO) with molecular weights (kDa) indicated; the first lane in each panel corresponds to a control transfection ('mock') with the appropriate empty expression vector;

FIG. 3E shows a quadrant plot of average competition versus enrichment SILAC ratios from quantitative proteomics experiments (left); high-reactivity targets of probe 2 are found in the upper right hand quadrant (33 total); among them is FTO (11) (highlighted in blue), which was selected for validation in FIG. 3D; the ten high-reactivity targets of probe 1 shown in FIG. 3B are numbered and highlighted in red on the plot (left) and listed by name to the right of the plot to show profile overlap; high-reactivity protein targets of both probes are listed in red and those either undetected or not quantified with probe 2 are listed in gray; note that average competition ratios for LGMN (2) and KEAP1 (7) fall below the threshold ratio; FIG. 3F shows extracted parent ion chromatograms and corresponding heavy/light ratios for representative tryptic peptides of FTO quantified in enrichment and competition experiments;

FIGS. 4A-4H show the functional profiling of the pyruvoyl cofactor of AMD1 by hydrazine probes as described in Example 4; FIG. 4A shows three forms of AMD1, including (1) inactive proenzyme (38 kDa), (2) catalytically competent N-terminal pyruvoyl-containing enzyme (30 kDa) expected to be probe-reactive (pyruvoyl functionality shown in red), and (3) inactivated enzyme bearing an alanine form of the cofactor; FIG. 4B shows expression and probe 1-labeling profiles of N- (left) versus C-terminal (right) FLAG-tagged AMD1 in transfected HEK293T cells; forms (1)-(3) as shown in FIG. 4A are indicated; FIG. 4C shows extracted parent ion chromatograms (left) and corresponding isotopic envelope (right) for the N-terminal pyruvoyl peptide of AMD1 labelled by probe 1 (SEQ ID NO: 1); FIG. 4D shows MS2 spectra of the N-terminal pyruvoyl peptide of AMD1 labelled by probe 1 (SEQ ID NO: 1); the b- and y-ions assign the labelled site (*) to the N-terminal Ser69 residue; FIG. 4E shows expression and probe 1-labeling profiles of endogenous AMD1 in HEK293T cells following treatment with difluoromethylornithine (DFMO); FIG. 4F shows expression and probe 1-labeling profiles of AMD1-transfected cells cultured in media containing 10 M versus 200 M L-methionine (left) and corresponding band intensities for each (right); profiles were generated for three biological replicates; standard deviation is represented by error bars for the low methionine condition, as band intensities were normalized for the high methionine condition;

FIG. 4G shows from cells generated as in FIG. 4F, ratios for AMD1 peptides—probe 1-labelled pyruvoyl (SEQ ID NO: 1) (A) and alanine (SEQ ID NO: 2) (B) forms of N-terminal peptide, as well as an internal peptide (SEQ ID NO: 3) (C) (shown in FIG. 4H)—in experiments comparing cells grown in low (10 μM) versus high (200 μM) methionine and compared by modifying corresponding peptides with light and heavy formaldehyde, respectively; FIG. 4H shows a summary table of the data graphically represented in FIG. 4G; results shown are from a single experiment representative of two independently performed experiments;

FIGS. 5A-5D show in vitro reactivity of probe 1 with purified AMD1 as described in Example 4; FIG. 5A shows a schematic representation of how parallel samples of reconstituted active AMD1, expressed and purified from E. coli, were incubated in the absence (green traces) or presence (red traces) of probe 1; trypsin-digested peptides from each sample were compared. FIG. 5B shows extracted parent ion chromatograms for the unlabelled pyruvoyl-containing tryptic peptide (pyruvoyl68-Lys74, SEQ ID NO: 4) from both samples, showing loss of signal in the sample treated with probe 1; FIG. 5C shows sequence coverage of all unmodified peptides (highlighted in yellow) versus the modified peptide that harbors the cofactor (highlighted in blue) of the AMD1 sequence (SEQ ID NO: 5); FIG. 5D shows extracted parent ion chromatograms for tryptic peptides highlighted in FIG. 5C (SEQ ID NOs: 6-21); with the exception of pyruvoyl68-Lys74, all AMD1 peptides detected in the untreated sample were also detected with comparable intensity in the probe-treated sample;

FIGS. 6A-6F shows the identification of a hydrazine-reactive site in secernin-3 (SCRN3); FIG. 6A shows a schematic representation of the characterization of probe labelled peptides using the isoTOP-ABPP method as described in Example 4; FIG. 6B shows N-terminal sequence alignment of human secernin proteins (SEQ ID NOs: 22-24); the predicted catalytic residues for the putative Ntn hydrolase activities of secernins are highlighted (in red) and the associated cleavage sites of predicted proforms are indicated by the arrow; FIG. 6C shows extracted double-charged MS1 ion chromatograms (left) and corresponding isotopic envelopes (right) for co-eluting heavy- and light-tagged peptides labelled by probe 2 (in blue and red, respectively); FIG. 6D shows a comparison of high-resolution MS2 spectra generated from light-versus heavy-tagged parent ions (left); the y-ions resolve the modified site (*) to the N-terminal cysteine and/or adjacent aspartate (right) (SEQ ID NO: 25); FIG. 6E shows probe 2-labeling and expression profiles of $Cys_6$-to-$Ala_6$ (C6A) and $Asp_7$-to-$Phe_7$ (D7F) mutant SCRN3 proteins compared to wild-type (WT) SCRN3; FIG. 6F shows a reaction scheme (upper schematic) (SEQ ID NOs: 25 and 28) and MS results-based prediction of the structure of the probe 2-SCRN3 adduct (lower schematic);

FIGS. 7A-7I show MS characterization of probe 1-labelled and probe 2-labelled peptides of AMD1 as described in Example 4; FIG. 7A shows structures and theoretical parent masses of heavy- and light-tagged AMD1 pyruvoyl peptides labelled by probe 1 (SEQ ID NO: 26) and processed by the isoTOP-ABPP method; FIG. 7B shows extracted parent ion chromatograms (upper) and corresponding isotopic envelopes (lower) for heavy- (blue) and light- (red) tagged peptides detected in endogenous (left) versus transfected (right) forms of AMD1 in HEK293T cells; FIG. 7C shows MS2 spectra generated from parent ions in FIG. 7B (right); y-ions are shown in green, fragment ions that retain the heavy or light portions of the tag are shown in blue and red, respectively, and those that lost this isotopic signature are shown in purple; FIG. 7D shows a summary table of theoretical versus observed spectra assignments for peptides isolated from endogenous versus transfected AMD1 and generated under low- versus high-resolution MS2 conditions, respectively; FIG. 7E shows a structure assignment for non-canonical $Y_{tag}$ and $B_{tag}$ fragment ions; FIG. 7F shows structures and theoretical parent masses of heavy- and light-tagged AMD1 pyruvoyl peptides labelled by probe 2 (SEQ ID NO: 27) and processed by the isoTOP-ABPP method; FIG. 7G shows extracted parent ion chromatograms (upper) and corresponding isotopic envelopes (lower) for heavy- (blue) and light- (red) tagged peptides isolated from AMD1-transfected HEK293T cells; FIG. 7H shows structure assignment for non-canonical $Y_{tag}$ and $B_{tag}$ fragment ions required for identification; FIG. 7I is a summary table of theoretical versus observed spectra assignments for peptide pairs generated under high-resolution MS2 conditions;

FIGS. 8A-8C show data supporting the structural assignment of an N-terminal glyoxyl group in SCRN3 as described in Example 4; FIG. 8A shows a schematic of heavy-Arg/Lys-labelled SCRN3-transfected cells treated with probe 2, followed by processing by isoTOP-ABPP, furnishing an isotopically differentiated probe 2-labelled SCRN3 peptide pair (red and blue) (SEQ ID NO: 28), which co-elutes with a light amino acid-labelled probe 2-$Glyoxylyl_6$-$Arg_{20}$ standard (also an isotopically differentiated peptide pair; black and green); FIG. 8B shows inset chromatogram with all four traces scaled to the same intensity (upper right, insetplot) to show co-elution of endogenous and standard 2-Glyoxylyl$_6$-Arg$_{20}$ SCRN3 peptides; corresponding isotopic envelopes are shown below the chromatograms; FIG. 8C is a comparison of high-resolution MS2 spectra for light-tagged standard versus endogenous 2-Glyoxylyl$_6$-Arg$_{20}$ SCRN3 peptides (inverted y-axis) distinguished by the expected 10 Da mass shift for y$_8$-ions containing the C-terminal Arg residue;

FIG. 9A shows the structures and theoretical parent masses of heavy- and light-tagged SCRN3 glyoxylyl peptides labelled by probe 1 (SEQ ID NO: 29) and processed by the isoTOP-ABPP method; FIG. 9B shows extracted parent ion chromatograms (upper) and corresponding isotopic envelopes (lower) for heavy- (blue) and light- (red) tagged peptides detected from SCRN3-transfected HEK293T cells; FIG. 9C is summary table of theoretical versus observed spectra assignments generated under high-resolution MS2 conditions; FIG. 9D shows MS2 spectra generated from parent ions of FIG. 9B; y-ions are shown in green and the b7-ion series in blue (heavy) and red (light).

FIG. 11A shows a schematic of the reaction of hydrazine probes with glyoxylyl/pyruvoyl groups; FIG. 11B shows the chemical mechanism for reaction shown in FIG. 11A; FIG. 11C shows a schematic of the reaction of hydrazine probes with an aspartimide group;

FIGS. 13A-13D show MS characterization of cysteine-derived glyoxylyl and pyruvoyl groups; FIG. 13A shows extracted parent ion chromatograms for heavy- and light-tagged pairs of probe 2-labelled glyoxylyl (SEQ ID NO: 28) (A, in blue and red, respectively) and pyruvoyl (SEQ ID NO: 31) (B, in green and black, respectively)N-termini; FIG. 13B shows the relative intensity of A vs. B pairs is generally unaffected by exposure to TCEP, a reductant, which can, under certain conditions, catalyze desulfurization of peptides[8]; this ratio was monitored under the following conditions: 1) standard protocol according to Example 2, 2) TCEP reduction omitted, 3) added alkylation step prior to click chemistry, 4) added alkylation step following click chemistry and TCEP reduction omitted and 5) added alkylation step following click chemistry; unless otherwise indicated, standard reduction and alkylation were included; FIGS. 13C and 13D show shifts in the b7-ion series of the MS2 spectra for 2-labelled pyruvoyl (SEQ ID NO: 31) (FIG. 13C) and glyoxylyl (SEQ ID NO: 28) (FIG. 13D) peptides caused by growing SCRN3-transfected cells in media containing L-[$^{15}$N$^{13}$C$_3$]cysteine (inverted y-axis); structures for interpreting MS2 spectra with heavy atoms (in purple) retained in the N-terminus are shown to the left of each spectrum; the parent m/z (indicated on the y-axis) values and b7-ion series values increase by 3 versus 2 Da for formation and capture of the pyruvoyl and glyoxylyl forms, respectively; note that the y$_8$-ion values, which would correspond to a C-terminal mass shift, are unchanged in L-[$^{15}$N$^{13}$C$_3$]cysteine samples;

FIG. 14A shows the reductive aniline exchange of probe 2 from probe 2 labeled glyoxyl-modified SCRN3 (SEQ ID NO: 32) to arylamine N-terminal peptide (SEQ ID NO: 33) after digestion to release internal peptide (SEQ ID NO: 34); FIG. 14B shows peak areas and absolute amounts of heavy SCRN3 peptides (blue) and light (red) standards (SEQ ID NOs: 33 and 34) quantified in a representative experiment; FIG. 14C shows the extracted parent ion chromatograms (left) and isotopic envelopes (right) for arylamine N-terminus (upper) and an internal peptide (lower) indicating the amount of respective standard added to the sample; FIG. 14D shows the MS2 spectra of the arylamine products of the synthetic standard (red) versus endogenous (blue) SCRN3 peptides; the y-ion values for the heavy SCRN3 peptide reflect a C-terminal mass shift (inverted axis);

FIG. 15A shows the peak areas and absolute amounts of heavy SCRN3 peptides (blue) and light (red) standards (SEQ ID NOs: 34 and 35) quantified in a representative experiment; FIG. 15B shows the extracted parent ion chromatograms (left) and isotopic envelopes (right) for the alkylated cysteine N-terminus (upper) and an internal peptide (lower) indicating the amount of respective standard added to the sample;

FIGS. 20A-20D shows the structures of embodiments of protein conjugates according to the invention; FIG. 20A shows the structure of a protein conjugate of formula (I) formed by reaction of a hydrazine or oxyamine probe of the invention with an ester or thioester electrophilic PTM of a protein; specific structures of ester and thioester electrophilic PTMs are shown below, some of which are also shown in FIG. 19; FIG. 20B shows the structure of a protein conjugate of formula (II) formed by reaction of a hydrazine or oxyamine probe of the invention with a carbonyl containing electrophilic PTM of a protein; specific structures of carbonyl containing electrophilic PTMs are shown below, some of which are also shown in FIG. 19; FIG. 20C shows the structure of a protein conjugate of formula (III) formed by reaction of a hydrazine or oxyamine probe of the invention with a quinone modification installed as a covalent modification or a quinone cofactor attached to a protein as prosthetic group; specific structures of quinone modifications and cofactors are shown below, some of which are also shown in FIG. 19; and FIG. 20D shows the structure of a protein conjugate of formula (IV) formed by reaction of a hydrazine or oxyamine probe of the invention with an oxidative PTM; specific structures of conjugates formed with Flavin, heme iron, and non-heme iron cofactors are shown below in which $N_2$ is released a byproduct of the reaction of the probe with the oxidative PTM; also shown is a protein conjugate formed by reaction of a hydrazine probe with a 4-methylideneimidazole-5-one (MIO) cofactor, which is similar in structure to a protein conjugate of formula (IV), except that an —NH—NH— (when hydrazine probe is used) or —NH—O— (when oxyamine probe is used) is inserted between the linker X and protein/prosthetic group in formula (IV);

FIG. 21A shows the structure of oxyamine probe 3; FIG. 21B shows Western blots (upper) and RP-ABPP data (lower) for oxyamine probe-treated transfected cells expressing the indicated target proteins (SCRN3 and KEAP1) with molecular weights (kDa) indicated; labelling with oxyamine probe 3 is compared to labelling with hydrazine probe 2;

FIGS. 22A-22C show MS characterization of cysteine-derived glyoxylyl and pyruvoyl groups; FIG. 22A shows the structure of captured glyoxylyl and pyruvoyl groups;

FIG. 22B shows an extracted parent ion chromatogram for probe 3-labelled glyoxylyl (A) and pyruvoyl (B); and FIG. 22C shows relative intensity of probe 1, 2, and 3-labelled glyoxylyl and pyruvoyl groups;

FIG. 23A shows a schematic representation of the general method for validation of a probe reactive group; FIG. 23B shows a schematic representation of the characterization of probe labelled peptides using the isoTOP-ABPP method as described in Example 4 for probe 3-treated KEAP-1transfected cells; FIG. 23C shows extracted MS1 ion chromatographs (top) and corresponding isotopic envelopes (bottom) for co-eluting heavy and light-tagged peptides labelled by probe 3;

FIG. 24A shows images of gels visualized by fluorescence (left) and coomassie stain (right) of the soluble proteome of lung, liver, and brain tissue of mice i.p. injected with probe 2; FIG. 24B shows images of gels visualized by fluorescence (left) and coomassie stain (right) of the membrane proteome of lung, liver, and brain tissue of mice i.p. injected with probe 2;

FIG. 25 shows the results of competition experiments with the competitor drugs phenelzine (having a hydrazine moiety) and isoniazid (having a hydrazide moiety) as described in Example 7; a schematic diagram of the experimental design is shown at the left; extracted parent ion chromatograms and corresponding H/L ratios for representative tryptic peptides of four protein targets of probe 1 (AMD1, SCRN3, SCRN 1 and LGMN) quantified in the competition experiments with isoniazide and phenelzine is shown at the right; and FIGS. 26A-26D show the structures and syntheses of probe-labelled peptides as described in Example 5 and used in the study described in Example 4; FIG. 26A shows the synthesis of Glyoxylyl6-Arg20 peptide (SI-7) (SEQ ID NO: 37) from SI-6 peptide (SEQ ID NO: 36); FIG. 26B shows the synthesis of the hydrazone product of probe 2-labelled glyoxylyl6-Arg20 peptide (SI-8) (SEQ ID NO: 38) from SI-7 (SEQ ID NO: 37); FIG. 26C shows the structures of an enzymatic cleavage of the isotopic protease-cleaved azide tags (SI-10$_{heavy}$/SI-10$_{light}$) (SEQ ID NO: 40) from SI-9$_{heavy}$/SI-9$_{light}$ (SEQ ID NO: 39); and FIG. 26D shows the hydrazone product of probe 2-labelled glyoxylyl6-Arg20 peptide (SI-11$_{heavy}$/SI-11$_{light}$) (SEQ ID NO: 41) obtained from SI-8 (SEQ ID NO: 38) and SI-10$_{heavy}$/SI-10$_{light}$ (SEQ ID NO: 40).

DETAILED DESCRIPTION OF THE INVENTION

Figure 7A:
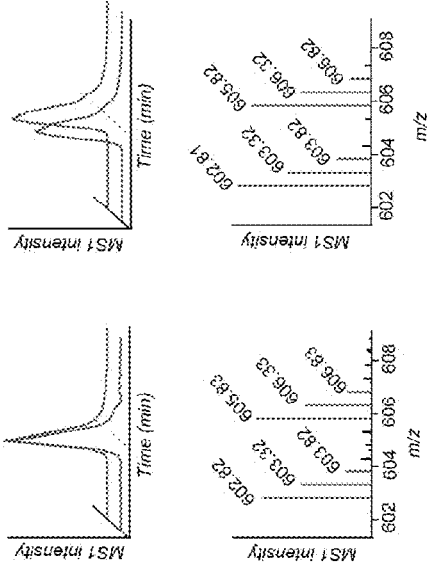
Figure 7C:
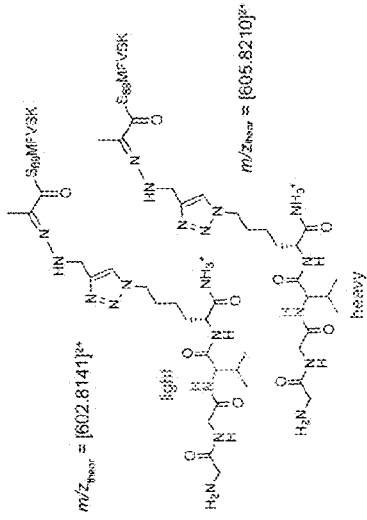
Figure 7B:
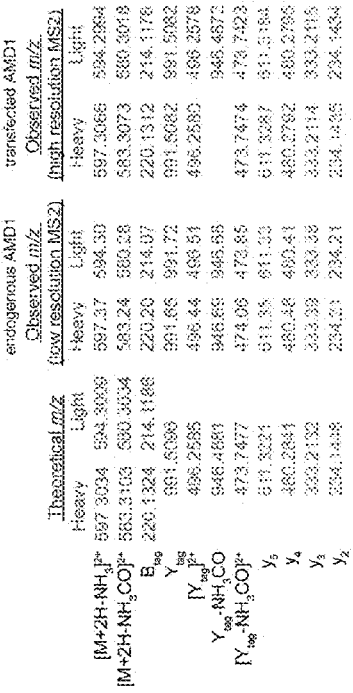
Figure 7D:
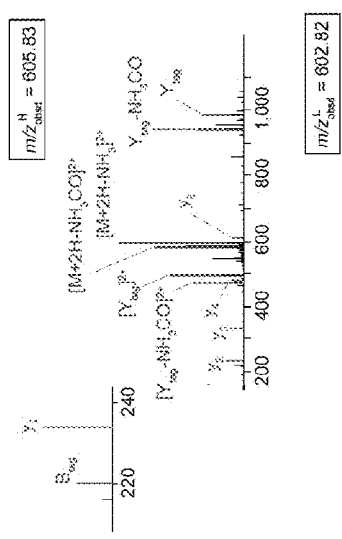
Figure 7E:
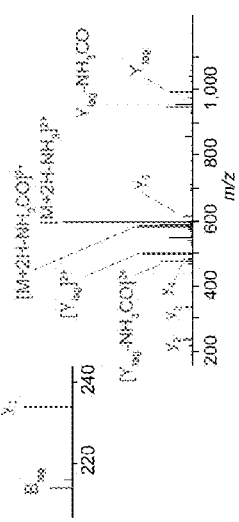
Figure 9A:
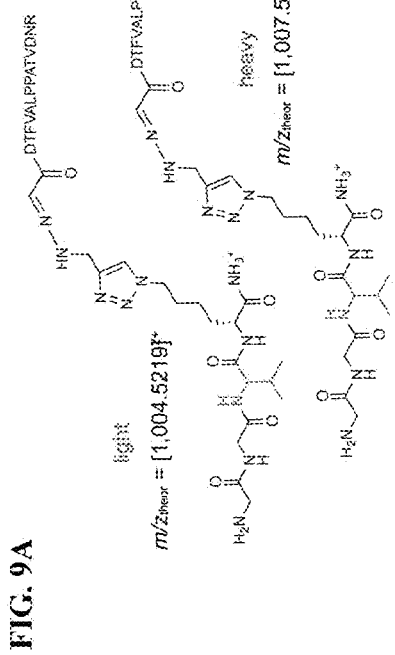
FIGS. 9A-9D show MS characterization of the probe 1-labelled glyoxylyl group of SCRN3.
Figure 9B:
Figure 9C:
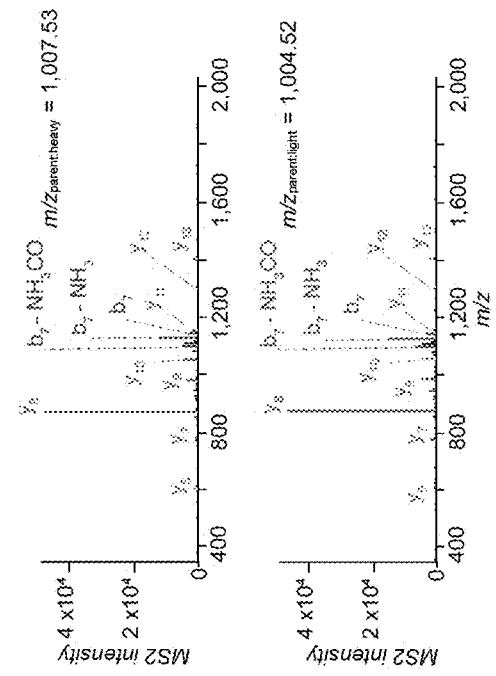
Figure 9D:
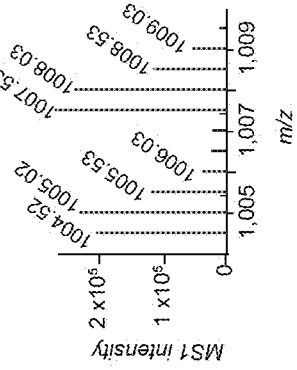

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

The invention relates to chemoproteomic methods of detecting and profiling electrophilic post-translational modifications (PTMs) and oxidative PTMs on proteins and protein conjugates in complex proteomic mixtures, such as in living cells (in situ), as described in Matthews et al. "Chemoproteomic profiling and discovery of protein electrophiles in human cells," *Nature Chemistry*, (2017) 9(3), 234-243, which is herein incorporated by reference in its entirety. Using the methods of the invention, both known and novel electrophilic and oxidative PTMs on proteins can be detected, identified, and profiled in cells using clickable hydrazine probes. The methods described herein use hydrazine probes or oxyamine probes capable of capturing functional electrophilic sites and redox active sites on proteins in living cells (in situ) without the need for exposing the cells to exogenous oxidative stressors, and thus can be used to study regulation of these PTMs in native biological systems, e.g., living cells, tissue systems, or in vivo in living organisms, for instance bacteria, pathogens, particularly human pathogens, and animals.

Notably, the methods described herein can be used to discover both known and novel PTMs, particularly electrophilic PTMs and oxidative PTMs, with no a priori knowledge of the presence or identity of the PTM. The electrophilic and oxidative PTMs detected, identified and/or discovered by the methods of the invention are typically naturally occurring, enzymatically installed, and generally functional, but usually cannot be predicted based on gene or protein sequence. Because such PTMs are typically cryptic, the methods of the invention can be applied for global discovery of electrophilic and oxidative PTMs.

In one aspect, the invention relates to a method for detecting an electrophilic post-translational modification (PTM) or oxidative PTM of at least one protein in a proteomic mixture, the method comprising:
  (i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the at least one protein, thereby forming a mixture comprising at least one alkyne-derivatized protein;
  (ii) labeling the at least one alkyne-derivatized protein with an azide-modified tag, optionally in the presence of a copper catalyst, to obtain at least one labelled protein; and
  (iii) analyzing the at least one labelled protein to thereby detect the PTM of the at least one protein.

Post-translational modifications (PTMs) are chemical modifications of a protein introduced after translation. PTMs typically occur at particular amino acid side chains or peptide linkages. Protein electrophiles refer to functional groups on proteins that react with nucleophilic groups. Protein electrophiles can generally be divided into two groups: (1) modifications installed as covalent PTMs; and (2) binding of exogenous molecules, such as oxidative prosthetic groups. PTMs can be covalent modifications or non-covalent modifications. According to embodiments of the invention, the methods of the invention can be used to identify PTMs acquired by a protein that react or interact with a hydrazine functional group or oxyamine functional group.

The phrases "electrophilic post-translational modification" and "electrophilic PTM" as used herein refer to a chemical modification installed onto a protein during post-translational processing of the protein that is reactive with nucleophilic groups. Electrophilic PTMs are part of the "electrophilome," which is the part of the proteome harboring electrophilic PTMs. Electrophilic PTMs typically comprise a carbonyl group, ester group, or thioester group that is installed onto a protein as a covalent modification. Examples of electrophilic PTMs comprising a carbonyl group include, but are not limited to, pyruvoyl modifications, glyoxylyl modifications, formylglycyl modifications, and quinone modifications. Examples of electrophilic PTMs comprising an ester or thioester group include, but are not limited to, aspartimide modifications, aspartyl phosphate modifications, and methyl ester modifications of aspartic acid and glutamic acid side chains. See, e.g., FIGS. 19 and 20A-20C for structures of electrophilic PTMs that can react with hydrazine probes or oxyamine probes according to the methods of the invention. Typically, such electrophilic PTMs are installed on enzymes, and are part of the catalytic machinery of the enzyme.

The phrases "oxidative post-translation modification" and "oxidative PTM" as used herein refer to a redox active site of a protein, which can be a covalently bound prosthetic group or non-covalently bound prosthetic group. A "prosthetic group" refers to a non-polypeptide unit used by proteins to carry out certain biological functions or activities. A prosthetic group can be an organic group (e.g., vitamin, sugar, lipid, etc.) or inorganic group (e.g., metal ion). Examples of oxidative PTMs include, but are not limited to, quinone cofactors, flavin cofactors, heme iron cofactors, and non-heme iron cofactors. Note that quinone can refer to an electrophilic PTM installed onto an amino acid residue of a protein, or an oxidative PTM, i.e., prosthetic group. See, e.g., FIGS. 19, 20C, and 20D for the structures of oxidative PTMs that can react with hydrazine probes or oxyamine probes according to the methods of the invention. For example, iron can coordinate to amino acid side chains (noncovalent), but may induce a reaction that leads to covalent modification of the protein by the probe. See, e.g., FIG. 20D. Electrophilic PTMs and oxidative PTMs are typically functional protein modifications installed at one or more amino acid residues of a protein that affect the biological activity of a protein and are generally not predictable from protein sequence analysis.

According to embodiments of the invention, electrophilic PTMs and oxidative PTMs react with hydrazine and/or oxyamine. In one embodiment, an electrophilic PTM that reacts with hydrazine and/or oxyamine comprises a carbonyl group (e.g., pyruvoyl modifications, glyoxylyl modifications, formylglycyl modifications, quinone modifications, etc.). In another embodiment, an electrophilic PTM that reacts with hydrazine and/or oxyamine comprises an ester group or thioester group (e.g., aspartimide modifications, aspartyl phosphate modifications, etc.). In yet another embodiment, an oxidative PTM that reacts with hydrazine and/or oxyamine comprises a redox active prosthetic group (e.g., Flavin cofactor, quinone cofactor, heme iron cofactor, non-heme iron cofactor, etc.).

Functional electrophilic PTMs and oxidative PTMs can be installed naturally onto a protein via a variety of mechanisms including, but not limited to, self-assembly often triggered by substrate binding, installation by dedicated enzyme machinery or high affinity binding of metabolite-derived small molecules. The majority of these groups serve as cofactors for enzyme catalysis, but can also form as enzyme intermediates in catalytic cycles (phosphatases) or serve as regulators of important processes (phosphorelay in bacteria or other species) and are found in bioactive peptide natural products or hormones. By contrast to functional nucleophiles, which are often revealed by gene and protein sequence, the majority of electrophilic PTMs and oxidative PTMs, especially in higher organisms, cannot readily be predicted because they are acquired post-translationally.

According to embodiments of the invention, electrophilic and oxidative PTMs can be detected on proteins in proteomic mixtures in vitro, in situ, or in vivo. As used herein, a "proteomic mixture" is a composition comprising one or more proteins. The proteomic mixture can be purified, meaning that it is free from other cellular components, or the proteomic mixture can be a complex mixture including other cellular components. Proteomic mixtures include, but are not limited to, intact, living cells (e.g., mammalian cells, human cells, bacterial cells, etc.), cell lysates, tissue from animal models, brain proteomes or brain tissue, primary biliary cirrhosis (PBC), tumors, in vitro mixtures of purified proteins, and other biological specimens/fluids (e.g., blood, urine, amyloid plaques, fecal samples). In one embodiment, a proteomic mixture is a cell. In another embodiment, a proteomic mixture is a tissue. In yet another embodiment, a proteomic mixture is a biological sample from a patient, which can include a cell or tissue. In yet other embodiments, the proteomic mixture is in a cell within a living organism (e.g., worms, mice, and other mammals), such that proteins are labelled with probes in vivo.

In preferred embodiments of the invention, the proteomic mixture is in a living cell (in situ) or living organism (in vivo).

According to embodiments of the invention, a method for detecting an electrophilic PTM or oxidative PTM of at least one protein in a proteomic mixture comprises contacting the proteomic mixture with a probe. The probes used in the methods of the invention can be considered activity-based probes (ABPs). "Activity-based probes" and "ABPs" are polyfunctional molecules with substantial irreversible binding to a target protein. ABPs thus typically comprise (1) a reactive functionality with affinity for a related group of proteins, such that the ABP will bind to the proteins, preferably irreversibly, and substantially inactivate the protein; and (2) a second functional moiety that permits detection, labeling, isolation, etc., of probe modified proteins. In some embodiments, probes useful in the methods of the invention comprise a hydrazine moiety and an alkyne moiety. The hydrazine moiety of the probe acts as the reactive functionality with affinity for electrophilic and oxidative PTMs in proteins, such as those described above, and has at least partial irreversible binding to proteins harboring such electrophilic and oxidative PTMs. The alkyne moiety of the probe permits detection, labeling, isolation, etc. of probe modified proteins by acting as a handle in "click chemistry" reactions for conjugation with azide labelled molecules via a 1,3-cycloaddition reaction to form a triazole linker. In other embodiments, probes useful in the methods of the invention comprise an oxyamine moiety and an alkyne moiety.

A "hydrazine moiety" refers to a hydrazine functional group having a structure —NH—NH$_2$. An "oxyamine moiety" refers to functional group having a structure —O—NH$_2$. An "alkyne moiety" refers to a functional group comprising a carbon-carbon triple bond. Alkyne moieties include terminal alkynes and cyclic alkynes, preferably terminal alkynes and cyclic alkynes that are reactive with azide (—N$_3$) groups. A terminal alkyne has at least one hydrogen atom bonded to a triply bonded carbon atom. A cyclic alkyne is a cycloalkyl ring comprising one or more carbon-carbon triple bonds, typically one carbon-carbon triple bond. Examples of cyclic alkynes include cyclooctyne and cyclooctyne derivatives, such as bicyclononyne (BCN), dibenzoazacyclooctyne (DIBAC), and dibenzocyclooctyne (DBCO). Click chemistry reactions between terminal alkynes and azides typically require the addition of a copper catalyst to promote the 1,3-cycloaddition reaction, and are known as copper-catalyzed azide-alkyne cycloaddition (CuAAC) reactions. However, click chemistry reactions between cyclooctyne or cyclooctyne derivatives and azides typically do not require the addition of a copper catalyst, and instead proceed via strain-promoted azide-alkyne cycloaddition (SPAAC).

In some embodiments, the alkyne moiety is a terminal alkyne.

According to embodiments of the invention, a probe can have a structure according to one of the following formulas:

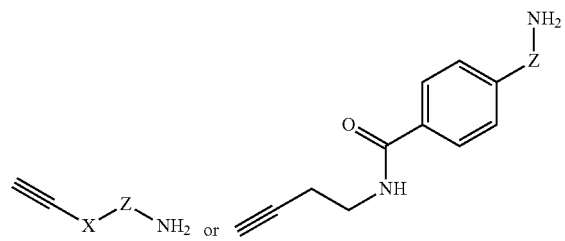

wherein X is a linker; and Z is oxygen or NH. In particular embodiments of the invention, a probe has one of the following structures:

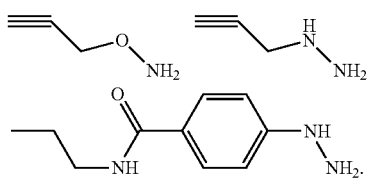

In general, when Z is NH, a probe is referred to as a hydrazine probe, or a probe comprising a hydrazine moiety; and when Z is oxygen, a probe is referred to as an oxyamine probe, or a probe comprising an O- or N-hydroxylamine moiety. Such probes can also be referred to as nitrogenous probes or alpha-nucleophiles. A linker can be used to introduce structural diversity into the probes. Exemplary and non-limiting examples of hydrazine probes having a terminal alkyne suitable for use in the invention are shown in FIG. 1A (see Probes 1 and 2).

According to embodiments of the invention, upon contacting the proteomic mixture with a probe comprising a hydrazine or oxyamine moiety and an alkyne moiety, a covalent linkage is formed between the hydrazine or oxyamine moiety of the probe and the electrophilic or oxidative post-translational modification of the at least one protein, resulting in a mixture comprising at least one alkyne-derivatized protein. As used herein, an "alkyne-derivatized protein" refers to a protein that is modified to include a covalently bound alkyne group. According to embodiments of the invention, an alkyne-derivatized protein is modified to include a covalently bound alkyne group by reaction of the hydrazine and/or oxyamine probes described herein with protein electrophiles.

The type of covalent linkage, or adduct, formed with the probe depends on the electrophilic PTM or oxidative PTM that reacts with the hydrazine or oxyamine moiety of the probe. In some embodiments, the hydrazine moiety reacts with an electrophilic PTM comprising an ester or thioester functionality (e.g., aspartyl phosphate, aspartamide, etc.) to produce a hydrazide adduct. In other embodiments, the hydrazine moiety reacts with electrophilic PTMs comprising a carbonyl functional group (e.g., glyoxyl modification, pyruvoyl cofactor, formylglycyl modification, quinone modification, etc.) to produce a hydrazone adduct. In yet other embodiments, the hydrazine moiety reacts with an oxidative PTM by alkylation. Non-limiting examples of covalent linkages or adducts that can be formed upon reaction of the hydrazine moiety and an electrophilic PTM or oxidative PTM of a protein include hydrazides, hydrazones, alkylated hydrazines, and alkylated exogenous cofactors. In other embodiments, the oxyamine moiety of the probe reacts with electrophilic PTMs as described above to form oxime adducts.

In some embodiments, the mixture comprising the at least one alkyne-derivatized protein is contacted with a reducing agent. The addition of a reducing agent can reduce certain adducts formed between the hydrazine moiety of the probe and electrophilic PTMs or oxidative PTMs of the proteins in the proteomic mixture to form a more stable covalent linkage that is less susceptible to degradation during subsequent processing steps. For example, capture of certain carbonyl electrophiles by the hydrazine moiety of the probes may form unstable or more labile hydrazone adducts, which can be converted to more stable hydrazide adducts by a reducing agent. Any reducing agent known in the art in view of the present disclosure can used. Examples of reducing agents suitable for use in the invention include, but are not limited to, sodium borohydride ($NaBH_4$) and sodium cyanoborohydride ($NaCNBH_3$). For example, when the proteomic mixture is in a living cell, a reducing agent can be added during cell lysis.

According to embodiments of the invention, the at least one alkyne-derivatized protein is labelled with an azide-modified tag to obtain labelled protein(s). The azide moiety of the tag reacts with the alkyne moiety of the alkyne-derivatized protein via a "click chemistry" reaction to form a triazole based linkage. In such embodiments in which the alkyne moiety is a terminal alkyne, a copper catalyst can be added to the labeling reaction to promote a reaction between the alkyne moiety of the alkyne-derivatized protein and the azide moiety of the azide-modified tag. Any copper catalyst that promotes cycloaddition reactions between azides and alkynes known in the art in view of the present disclosure can be used. Examples of copper catalysts suitable for use in the invention include, but are not limited to, copper sulfate ($CuSO_4$). The tag-labelled alkyne-derivatized protein in the mixture can be enriched, isolated or purified from the mixture. A tag can be, for example, an imaging agent, an enrichment tag, an isotope tag, degradation tag, or chemical or enzymatic cleavage tag.

In one embodiment, a tag is an imaging agent. An imaging agent is an agent that allows for visualization, and optionally quantification, of proteins having electrophilic PTMs or oxidative PTMs that form covalent adducts with hydrazine or oxyamine probes according to the methods of the invention. Examples of imaging agents include, but are not limited to, fluorescent dyes and radioisotopes. Any fluorescent dye or radioisotope known to those skilled in the art in view of the present disclosure can be used. Examples of fluorescent dyes suitable for use in the invention include, but are not limited to, rhodamine dyes, e.g., 6-TAMRA (6-carboxytetramethylrhodamine), etc.; coumarin dyes, e.g., coumarin, methoxycourmarin, hydroxycoumarin, aminocoumarin, etc.; cyanine dyes, e.g., Cy2, Cy3, Cy5, etc.; fluorescein dyes, e.g., fluorescein isothiocyanate (FITC), etc., boron-dipyrromethene (BODIPY) dyes; alexa fluor dyes (available from Molecular Probes), e.g., Alexa Fluor 350 (blue), 405 (violet), 430 (green), 488 (cyan-green), etc.; acridine orange; and Hoechst stains. Fluorescent dyes and other imaging agents used for, e.g., tissue imaging are well known to those of ordinary skill in the art in view of the present disclosure. In one specific embodiment, the azide modified tag is azide-rhodamine ($Rh-N_3$), in which the imaging agent is the fluorescent dye rhodamine.

In one embodiment, a tag is an enrichment tag. An enrichment tag is a molecular entity that can be used to isolate and/or purify hydrazine probe modified proteins from a proteomic mixture. An enrichment tag can be an affinity tag. Any enrichment or affinity tag known to those skilled in the art in view of the present disclosure can be used. Examples of affinity tags include, but are not limited to, biotin, desthiobiotin, FLAG tag (DYKDDDDK) (SEQ ID NO: 42), polyhistiding tag (His-tag), glutathione S-transferase tag (GST tag), and epitope tags.

In another embodiment, an affinity tag, is a photoaffinity tag.

In another embodiment, a tag is an isotope tag. As used herein, "isotope tag" refers to a chemical moiety having suitable chemical properties for incorporation of an isotope, allowing the generation of chemically identical reagents of different mass, which can be used to differentially tag a polypeptide in two samples. An isotope tag can also be an isotopically labelled affinity tag or enrichment tag. A non-limiting example of an isotopically labelled affinity tag that can be used for enrichment and/or detection of probe labelled proteins includes isotopically labelled biotin-azide tags.

In yet other embodiments, a tag is a degradation tag, or a chemical or enzymatic cleavage tag. Degradation tags can be used to mark probe-labelled proteins for degradation, e.g., by cellular machinery. Chemical or enzymatic cleavage tags can be used to mark probe-labelled proteins for cleavage, either by means of a chemical or enzyme.

In some embodiments of the invention, a probe of the invention can be pre-conjugated to a tag, e.g., an azide-modified tag, prior to contacting the probe with a proteomic mixture. In such embodiments, contacting the proteomic mixture with a probe results in a labelled protein upon reaction of the hydrazine or oxyamine moiety of the probe with an electrophilic PTM or oxidative PTM of protein(s) in the proteomic mixture. The labelled proteins can then be enriched, detected, and/or identified according to the methods described herein.

In some embodiments, the proteomic mixture is in an intact, living cell. In such embodiments, the methods of the invention further comprise a step of lysing the cells. Cell lysis produces a cell lysate containing the alkyne-derivatized proteins. Cell lysis is preferably performed after the cells are contacted or incubated with a hydrazine or oxyamine probe for a sufficient amount of time to form a covalent linkage between the hydrazine or oxyamine probe and electrophilic and/or oxidative PTMs of protein(s) in the cells. The alkyne-derivatized proteins can be purified or enriched from the cell lysate prior to labelling with an azide-modified tag, or the alkyne-derivatized proteins can be labelled with an azide-modified tag within the cell lysate. Typically, the alkyne-derivatized proteins will be labelled with an azide-modified tag prior to enrichment or purification. Any method known to those skilled in the art in view of the present disclosure can be used for cell lysis including, but not limited to, sonication, freeze/thaw cycles, and/or chemical lysis using, e.g., detergents.

In some embodiments, proteins are labelled by probes according to the methods of the invention in living organism, i.e., in vivo. In such embodiments, probe is injected into the organism. Tissue or other biological sample is harvested from the organism and then incubated with azide-modified tag to detect the alkyne-derivatized proteins.

According to embodiments of the invention, the alkyne-derivatized proteins are detected subsequent to labeling with an azide-modified tag. In some embodiments, the labelled proteins are analyzed by detecting the tag, e.g., when the tag is an imaging agent, such as a fluorescent dye, thereby detecting the electrophilic PTM or oxidative PTM of the at least one protein. In other embodiments, the tag is used to enrich or purify the labelled proteins from the proteomic mixture to facilitate detection and analysis of the labelled proteins, such as by mass spectrometry (MS), as described in greater detail below. Thus, the detection or analysis method often, but not always, depends upon the particular type of tag selected to label the alkyne-derivatized proteins. For example, in those embodiments in which an imaging agent (e.g. a fluorescent dye) is used as the tag, SDS-PAGE analysis and in-gel fluorescence scanning can be used to detect the tag, thereby detecting the labelled proteins. In other embodiments in which an affinity tag (e.g., epitope tag) is used, SDS-PAGE followed by Western blot analysis using antibodies specific for the affinity tag can be used to detect the tag, thereby detecting the labelled proteins. In yet other embodiments in which an isotope tag is used (e.g., isotopically labelled affinity tag), mass spectrometry (MS) analysis can be used to detect the labelled proteins.

In some embodiments, a method of detection comprises an enrichment step, in which labelled proteins are enriched or purified from the proteomic mixture. An enrichment step is typically performed after the alkyne-derivatized proteins are labelled with an azide modified tag prior to the detection or analysis step, e.g., detection by mass spectrometry, in gel fluorescence, Western blot, etc. Enrichment can be accomplished by, e.g., labelling the alkyne-derivatized proteins with an affinity tag, such as biotin, and immobilizing the biotin-labelled proteins on streptavidin coated beads or a streptavidin coated column. Enrichment removes the majority of cellular components and proteins not labelled with hydrazine or oxyamine probes from the alkyne derivatized proteins. Thus, an enriched sample of alkyne-derivatized proteins is one in which the majority of cellular components and proteins not labelled with the hydrazine or oxyamine probes have been removed.

In some embodiments, mass spectrometry is used to detect or analyze the labelled proteins. Mass spectrometry is an analytical technique that ionizes chemical species and sorts the ions based on their mass-to-charge-ratio. In general, an ionization source is used to generate gas phase ions from a biological or chemical molecule (e.g., peptide), and the gas phase ions are detected using an ion detector. Mass spectra, plots generated from the ion signal as a function of the mass-to-charge ratio, are used to determine the elemental or isotopic signature of a sample, the masses of particles and or molecules (e.g., peptides), and to elucidate the chemical structures of molecules, such as peptides. A variety of mass spectrometry systems and methods can be employed in the methods of the invention including, but not limited to, orbitrap, ion trap, triple quadrupole, time-of-flight, quadrupole time-of-flight, and Fourier transform ion cyclotron mass analyzers (FT-ICR-MS). Mass spectrometers are typically equipped with matrix-assisted laser desorption (MALDI) and electrospray/nanospray ionization (ESI) ion sources to ionize peptides, although other methods of peptide ionization can be used. Such methods of mass spectrometry analysis are well known to those skilled in the art.

In some embodiments of the invention, proteins having electrophilic PTMs or oxidative PTMs labelled by hydrazine or oxyamine probes are isotopically labelled and characterized by mass spectrometry (MS). The incorporation of an isotope tag can be used to facilitate quantification of probe labelled proteins by mass spectrometry. In using an isotope tag, differential isotopes can be incorporated, which can be used to compare a known amount of a standard labelled molecule having a differentially labelled isotope from that of the sample molecule. Thus, a standard peptide having a differential isotope can be added at a known concentration and analyzed in the same MS analysis or similar conditions in a parallel MS analysis. A specific calibrated standard can be added with known absolute amounts to determine an absolute quantity of a probe labelled protein in sample. In addition, standards can be added so that relative quantification is performed. Isotopic labels can be incorporated directly into proteins (e.g., metabolically in living cells), or by conjugation of an isotopically labelled tag to the protein. Particular methods for isotopically labelling and characterizing proteins by mass spectrometry include, but are not limited to, fragment-based screening, SILAC (stable isotope labelling by amino acids in cell culture) methodology followed by MS analysis, isotopic tandem orthogonal proteolysis-ABPP (isoTOP-ABPP), tandem mass tag (TMT) channels, reductive demethylation (ReDiMe), isobaric tags for relative and absolute quantitation (iTRAQ) and label free quantitation.

Mass spectrometry analysis can also be combined with separation methods or other purification methods, such as chromatographic techniques, in gel digestion, etc. Separation methods, such as chromatographic techniques, are typically used prior to mass spectrometry analysis. Examples of chromatographic techniques suitable for use in the invention include, but are not limited to, liquid chromatography (including high performance liquid chromatography), ion exchange (strong and weak anion and cation exchange resins), hydrophobic and reverse phase, size exclusion, affinity, hydrophobic charge-induction chromatography, dye-binding and the like.

In a particular embodiment, multidimensional liquid chromatography-tandem mass spectrometry (LC-MS/MS), optionally combined with SILAC (stable isotope labelling by amino acids in cell culture) methodology is used to detect electrophilic PTMs of proteins. SILAC is a technique based on mass spectrometry that detects differences in protein abundance among samples using non-radioactive isotope labeling. Cells are differentially labelled by growing them in "light" medium containing naturally abundant amino acids or "heavy" medium containing amino acids labelled with stable (non-radioactive) heavy isotopes, e.g., $^{13}C$ instead of $^{12}C$ and/or $^{15}N$ instead of $^{14}N$. When the isotopically labelled analog of an amino acid is supplied to cells in culture instead of the natural amino acid, it is incorporated into all newly synthesized proteins. After a number of cell divisions, each instance of this particular amino acid will be replaced by its isotope labelled analog. Metabolic incorporation of the amino acids into proteins results in a mass shift of the corresponding peptides, which can be detected by mass spectrometry. SILAC can also be used to quantify the amount of protein in a sample. In particular, when the heavy and light samples are combined, the ratio of peak intensities in the mass spectra reflects the relative protein abundance. MudPIT (LC/LC-MS/MS) and SILAC methodology have been previously described by, e.g., Washburn et al. "Large-scale analysis of the yeast proteome by multidimensional protein identification technology" *Nat. Biotechnol.* 19, 242-247 (2001) and Mann, M. "Functional and Quantitative Proteomics Using SILAC" *Nat. Rev. Mol. Cell Biol.* 7, 952-958 (2006) which are herein incorporated by reference in their entireties. Quantitative proteomic analysis has routinely been employed as part of previously described ABPP platforms. SILAC methodology is particularly useful in those embodiments in which the proteomic mixture is in an intact, living cell, as the amino acids labelled with heavy isotopes are metabolically incorporated into proteins by the endogenous cellular machinery.

In other embodiments, isotopic tandem orthogonal proteolysis-ABPP, termed isoTOP-ABPP, can be used to detect and optionally quantify electrophilic PTMs in proteins. IsoTOP-ABPP uses chemical probes and quantitative mass spectrometry (MS). IsoTOP-ABPP and its use for quantitative proteomic analysis has been previously described by, e.g., Weerapana et al. "Tandem orthogonal proteolysis activity-based protein profiling (TOP-ABPP)—a general method for mapping sites of probe modification in proteomes" Nature Protocols, 2, 1414-1425 (2007); and Weerapana et al. "Quantitative reactivity profiling predicts functional cysteines in proteomes" Nature 468, 790-795 (2010), which are herein incorporated by reference in their entireties. In the IsoTOP-ABPP method, only probe-labelled peptides are enriched. Probe-labelled proteins can then be detected from their 1:1 ratio and co-elution of a peptide pair with a specific mass differential. Here, the inventors have applied IsoTOP-ABPP to discover modifications on proteins, whereas in previously published applications of IsoTOP-ABPP the site of probe labelling and structure of the labelled site is known a priori. By analyzing the data generated from Iso-TOP-ABPP, as described in greater detail below in Example 4, modifications on proteins can be discovered without prior knowledge of the site or structure of a modification.

In some embodiments, a method of detecting electrophilic PTMs or oxidative PTMs is used to identify proteins having such PTMs. In such embodiments of the invention, a method of detection further comprises identifying the protein(s) targeted and covalently modified by the hydrazine reactive probes.

In one embodiment, labelled proteins can be identified using LC-MS/MS in combination with SILAC methodology. For example, cells can be grown in "light" medium or "heavy" medium. The cells can then be contacted with a probe having hydrazine/oxyamine and alkyne moieties. The probe treated cells (heavy and light) are then mixed together and labelled with an affinity tag, such as biotin azide. The probe labelled proteins are enriched by affinity purification using streptavidin coated beads or a streptavidin coated column. The captured proteins are digested on bead or column by trypsin, and the tryptic digests are analyzed by LC-MS/MS. See, e.g., FIG. 3A. Once a peptide is analyzed by MS/MS, the resulting spectra can be compared to databases for determination of the identity of the protein harboring the electrophilic PTM or oxidative PTM. Methods for protein identification using one or more single peptide fragments to identify a parent polypeptide or protein from which the fragments were derived by, e.g., tryptic digest, is well known to those skilled in the art. An exemplary example of how LC-MS/MS combined with SILAC methodology can be used to identify probe labelled proteins in describe in more detail below (see Example 3).

It is also possible to identify the site (e.g., amino acid residue) at which the electrophilic PTM or oxidative PTM is installed using the methods of the invention. Thus, in some embodiments, a method of detecting an electrophilic PTM or oxidative PTM further comprises identifying the site (e.g. amino acid residue or residues) of post-translational modification, which may involve multiple residues or crosslinks. A site of post-translational modification can be identified using mass spectrometry as described in the present disclosure. See, e.g., Example 4.

In one particular embodiment, IsoTOP-ABPP is used to identify the site at which an electrophilic PTM is installed. For example, probe labelled proteomic mixtures are conjugated to isotopically labelled affinity tags containing an enzymatic cleavage site, such as biotin-TEV-azide. As used herein, "TEV" refers to the sequence recognized by the cysteine protease Tobacco Etch Virus (TEV) protease. However, it is possible to use other enzymatic cleavage sites and/or other affinity tags. The probe labelled proteins are enriched by affinity purification, e.g., using streptavidin coated beads or a streptavidin coated column. The captured proteins are digested with trypsin on bead or on column and unmodified peptides (i.e., the peptide fragments that do not contain the site of modification with the hydrazine probe) are removed. Remaining immobilized peptides containing the site of probe modification are further digested with an enzyme recognizing the enzymatic cleavage site, e.g., TEV protease, to release the peptide containing the site of probe modification from the bead or column. The released peptides are then analyzed by LC-MS/MS to identify the site of the protein at which the electrophilic PTM is installed. See, e.g., FIG. 6A. An exemplary example of how IsoTOP-ABPP can be used to identify a site of electrophilic post-translational modification in probe captured proteins is described in more detail below (see Example 4).

In some embodiments, methods of the invention further comprise characterizing the electrophilic or oxidative PTM. The terms "characterize," "characterizing," and "characterization" as used herein with respect to electrophilic or oxidative PTMs, particularly electrophilic or oxidative PTMs identified according to the methods of the invention, refer to identifying the structure and/or function of the electrophilic PTM or oxidative PTM. Any method known in the art in view of the present disclosure can be used to characterize an electrophilic or oxidative PTM. An exemplary and non-limiting analysis that can be used to characterize an electrophilic PTM, e.g., by identifying the structure of the electrophilic PTM, is described in greater detail below (see Example 4). Thus, the methods of the invention can also be used to assign protein function, because the structure of the electrophilic or oxidative PTM, once identified and characterized, will often define the type of catalytic activity the protein will have. The function of an electrophilic PTM or oxidative PTM can be further characterized by modulating biology to determine effects on cellular regulation, e.g., methionine dependence of proteins as described in Example 3.

In particular embodiments, a protein detected according to a method of the invention comprises a reactive carbonyl group, a reactive ester group, or a reactive thioester group installed on the protein as a PTM. In other particular embodiments, a protein detected according to a method of the invention is at least one protein selected from the group consisting of those proteins listed in Tables 1 and 3, and preferably at least one protein selected from the group consisting of those proteins listed in Table 2.

According to embodiments of the invention, methods of detecting electrophilic PTMs and oxidative PTMs can be used to detect and/or identify such modifications in uncharacterized proteins as well as detect and/or identify proteins not previously known to have such modifications. It is also possible to further study proteins captured by the hydrazine/oxyamine probes, such as by expressing identified proteins in cells using recombinant technology and using the hydrazine probes according to the methods of detection and identification described herein to, e.g., identify the site of probe modification and thus the site at which the electrophilic or oxidative post-translational modification is installed and/or characterize the electrophilic or oxidative PTM.

It is also possible that the structure of the electrophilic PTM and/or oxidative PTM captured by the hydrazine/oxyamine probes of the invention was previously unknown, e.g., novel carbonyl, ester, or thioester containing electrophilic PTMs, such that electrophilic and/or oxidative PTMs of novel structure may be identified using the methods described herein. Thus, in other embodiments of the invention, a method of detecting an electrophilic PTM or oxidative PTM can be used for de novo discovery of electrophilic PTMs and/or oxidative PTMs on proteins. The methods of the invention can thus also be used for discovery and identification of new proteins and/or discovery of previously unknown electrophilic PTMs on proteins that may provide new therapeutic targets for disease treatment (e.g., for drug discovery) and/or biomarkers for disease diagnosis, prognosis, or monitoring.

In another general aspect, the invention relates to a method for profiling an electrophilic post-translational modification (PTM) or oxidative PTM of at least one protein in a proteomic mixture, the method comprising:
 (i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the target protein to obtain at least one alkyne-derivatized protein;
 (ii) labeling the at least one alkyne-derivatized protein with an azide-modified tag, optionally in the presence of a copper catalyst, to obtain at least one labelled protein;
 (iii) enriching the at least one labelled protein; and
 (iv) quantifying the at least one labelled protein.

As used herein, the terms "profile" and "profiling" refer to monitoring post-translational regulation of proteins that use electrophilic cofactors. Preferably, post-translation regulation of proteins is monitored in a native biological system, such as in a living cell (in situ) or living organism (in vivo). In one embodiment, "profile" and "profiling" refer to differentiating protein activity from protein expression by detecting post-translational modifications of proteins. In another embodiment, "profile" and "profiling" refer to quantifying occupancy of post-translationally-installed modifications on proteins. As used herein, "occupancy" refers to a fraction of protein expressed in a cell that has an electrophilic PTM or oxidative PTM installed, and represents PTM stoichiometry of a protein in a cell. Typically, there is one electrophilic PTM or oxidative protein per protein. In another embodiment, "profile" and "profiling" refer to monitoring formation of an active form of an enzyme from an inactive state, and vice versa. In another embodiment, "profile" and "profiling" refer to evaluating protein function in cellular systems. In yet another embodiment, "profile" and "profiling" refer to monitoring the effects of different cellular conditions on post-translational modification states of proteins. In yet other embodiments, "profile" and "profiling" refer to monitoring changes in protein activity that result from electrophilic PTMs and/or oxidative PTMs; perturbing changes in protein activity that result from electrophilic PTMs and/or oxidative PTMs; and probing for cellular determinants of PTM installation and function. In other embodiments, "profile" and "profiling" refer to determining the tissue specificity of proteins having certain electrophilic PTMs and/or oxidative PTMs, e.g., for proteins ubiquitously expressed in an organism, but which may harbor an electrophilic PTM and/or oxidative PTM only in particular tissue(s) of the organism.

In a particular embodiment of the invention, "profile" and "profiling" refer to determining the stoichiometry of a functional PTM (electrophilic or oxidative) installed on a protein in a cell, e.g., the percentage of a protein expressed in a cell harboring a particular electrophilic or oxidative PTM. The percentage of protein expressed in a cell harboring a particular electrophilic or oxidative PTM can be calculated by determining the absolute amount of total protein versus the absolute amount of modified protein. The percent modified protein can be calculated according to (absolute amount modified protein)/(absolute amount of total protein)×100%. The absolute amount of total protein versus the absolute amount of modified protein can be determined by using "heavy" protein and two "light" synthesized peptides (one peptide containing the modification, and the other peptide being an internal unmodified protein that represents the total protein). By doping in known amounts of both peptides and conducting ratiometric comparison with the "heavy" equivalents, the absolute amounts can be determined. See, e.g., FIGS. 14A-14D and 15A-15B.

Electrophilic and oxidative post-translational modifications of proteins, proteomic mixtures, probes comprising a hydrazine or oxyamine moiety and an alkyne moiety, and tags for labeling alkyne-derivatized proteins are described above with respect to the methods of detecting electrophilic and oxidative PTMs of the invention.

The at least one protein to be profiled according to the methods of the invention can be a protein known to have electrophilic PTMs or oxidative PTMs, or it can be a protein identified as having a previously unknown electrophilic PTM or oxidative PTM. Previously unknown electrophilic PTMs and oxidative PTMs in proteins can be identified using the methods for detecting and/or identifying electrophilic PTMs and oxidative PTMs according to the invention.

According to embodiments of the invention, electrophilic PTMs and oxidative PTMs can be profiled in vitro (e.g., lysates, tissues, bodily fluids etc.), in situ (e.g., in living cells, or in vivo (e.g., in living organisms). Electrophilic and oxidative PTMs can be profiled in one cell type or in multiple different cell types to compare post-translation modification states of proteins in different cell types. For example, electrophilic and oxidative PTMs can be profiled in a cancerous cell line and a non-cancerous cell line to identify potentially relevant disease targets by quantifying differences in, e.g., occupancy of electrophilic and oxidative PTMs of one or more proteins. In other non-limiting embodiments, electrophilic and oxidative PTMs can be profiled in neurons.

According to embodiments of the invention, a method for profiling an electrophilic or oxidative PTM comprises enriching labelled proteins subsequent to labeling of the alkyne-derivatized proteins with an azide-modified tag. Any method known in the art in view of the present disclosure can be used to enrich the labelled proteins. Enrichment can be accomplished by, e.g., labeling the alkyne-derivatized proteins with an affinity tag, such as biotin, and immobilizing the biotin-labelled proteins on streptavidin coated beads or a streptavidin coated column. An enriched sample of labelled proteins is typically free of other cellular components and proteins not labelled with the hydrazine probes.

In a particular embodiment, the alkyne-derivatized proteins are labelled with azide-modified biotin, or azide-TEVbiotin, and subsequently enriched by capturing the biotin labelled proteins on streptavidin beads.

A method of profiling according to the invention further comprises quantifying the labelled protein. The terms "quantifying" and "quantification" as used herein with respect to a labelled protein refer to measuring the labelled protein to determine an amount, occupancy, or activity of the labelled protein. The quantification method can be an absolute measurement, or a relative measurement, e.g., an amount of a first protein can be determined based on, or relative to an amount of a second protein or other marker. Any method known in the art in view of the present disclosure can be used to quantify the labelled protein including, but not limited to, mass spectrometry, Western blot, fluorescence, etc.

In a preferred embodiment, labelled proteins are quantified by mass spectrometry, and more preferably LC-MS/MS. In such embodiments, the labelled proteins can be isotopically labelled to facilitate analysis using LC-MS/MS in combination with SILAC methodology or IsoTOP-ABPP, as described above and illustrated below in greater detail (see, e.g., Examples 3 and 4).

In yet another general aspect, the invention relates to a protein conjugate comprising a covalent bond between a hydrazine moiety of a probe comprising an alkyne moiety and an electrophilic post-translational modification (PTM) or oxidative PTM of a protein. According to embodiments of the invention, a protein conjugate comprises a structure of formula (I), formula (II), formula (III), or formula (IV):

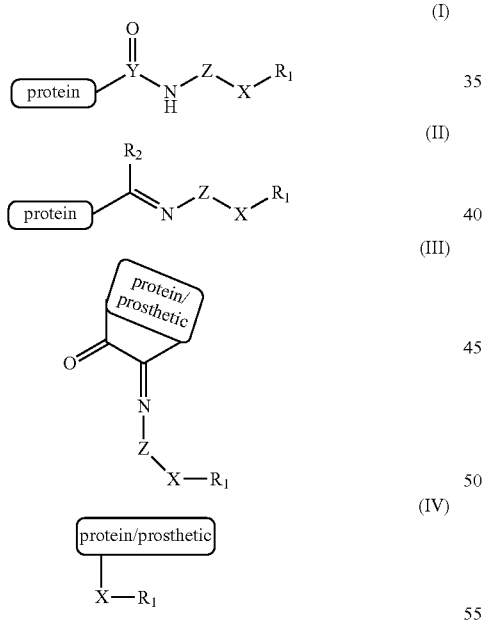

wherein $R_1$ is an alkyne; $R_2$ is a hydrogen or alkyl; X is a linker or spacer group; Y is carbon or sulfur; and Z is oxygen or NH. The alkyne can be a terminal alkyne or a cyclic alkyne, and is preferably a terminal alkyne. The linker or spacer group is derived from the hydrazine or oxyamine probe. Examples of linker or spacer groups include, but are not limited to alkyl, aryl, arylamines, etc. In some instances, a protein conjugate of formula (IV) can include an —NH—NH— or —NH—O— linkage (derived from the probe) between the linker X and protein/prosthetic group, such as when a probe reacts with a 4-methylideneimidazole-5-one (MIO) cofactor, such that the linker X comprises the —NH—NH— or —NH—O— moiety. See, e.g., FIG. 20D. However, the linker is not particularly limited, and can vary. In particular embodiments of the invention, a linker or spacer group is an alkyl, such as a $C_1$-$C_{10}$ alkyl, more preferably a $C_1$-$C_3$ alkyl; or a phenyl-C(O)—NH$_2$-alkyl group. In some embodiments, the hydrazone functionality of a protein conjugate of formula (II) is reduced using a reducing agent. A protein conjugate of formula (II) or formula (III) in which the hydrazine functionality (when Z is NH) is reduced using a reducing agent has a carbon-nitrogen single bond, rather than a carbon-nitrogen double bond as shown in formulas (II) and (III), when Z is NH.

As used herein, "alkyl" refers to any branched or straight chain saturated aliphatic hydrocarbon group. Examples of alkyl include, but are not limited to methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched chain isomers thereof. In a preferred embodiment, alkyl is methyl.

According to embodiments of the invention, a covalent modification between the hydrazine or oxyamine moiety of a probe and an electrophilic or oxidative PTM of the protein is formed. Such covalent modifications can be formed between the hydrazine or oxyamine moiety of the probe and electrophilic PTMs including, but not limited to, glyoxylyl modifications, pyruvoyl cofactors, formylglycyl cofactors, quinone cofactors, aspartyl phosphate modifications, and aspartamide sites, or oxidative PTMs including, but not limited to, Flavin cofactors, quinone cofactors, and heme and non-heme iron cofactors.

In particular embodiments of the invention, a protein conjugate has a structure of formula (I-a), formula (I-b), formula (II-a), formula (II-b), formula (III-a), formula (III-b), formula (IV-a), or formula (IV-b):

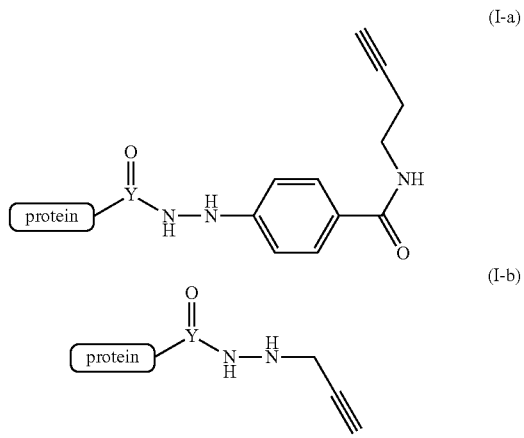

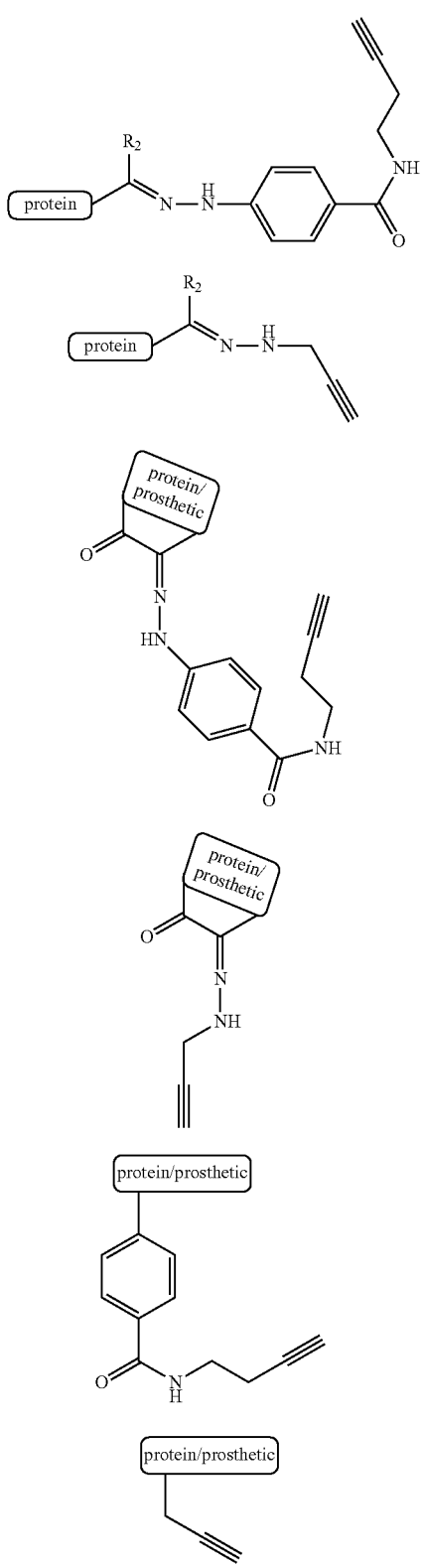

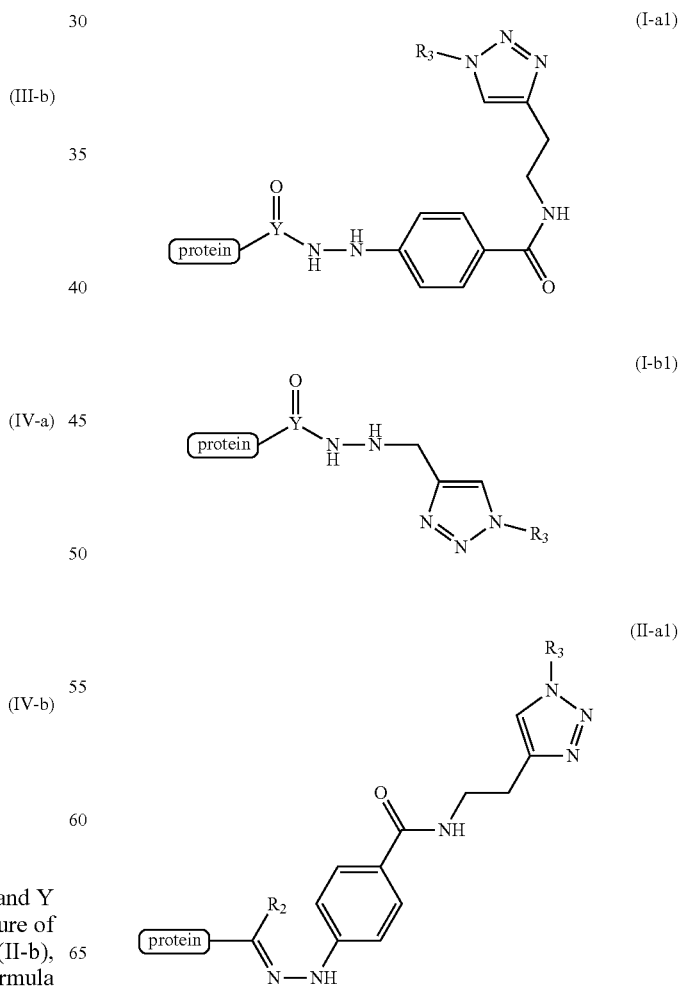

wherein $R_2$ is hydrogen or alkyl, preferably methyl; and Y is carbon or sulfur. Protein conjugates having a structure of formula (I-a), formula (I-b), formula (II-a), formula (II-b), formula (III-a), formula (III-b), formula (IV-a), or formula (IV-b) can be formed by reaction of an electrophilic or oxidative PTM of a protein, such as glyoxyl modification, pyruvoyl cofactor, aspartamide site, quinone modification or cofactor, flavin cofactor, heme cofactor, etc. with a hydrazine moiety of exemplary probes 1 and 2 as shown in FIG. 1A. In some embodiments, the hydrazone/hydrazide functionality of a protein conjugate of formula (II-a), (II-b), (III-a), or (III-b) may be susceptible to reduction using a reducing agent.

According to embodiments of the invention, a protein conjugate can further comprise an imaging agent, an enrichment tag, or an isotope tag covalently bound to the protein conjugate via a triazole linker. Other molecules can be conjugated to a protein conjugate of the invention via a triazole linker, such as a drug or radioisotope optionally bound to a metal chelator. Such labelled protein conjugates can be formed by reacting an azide-modified tag, or other azide-modified molecule, with a protein conjugate of the invention according to a "click chemistry" reaction, resulting in the formation of a stable triazole linker moiety.

In particular embodiments of the invention, a protein conjugate further comprising an imaging agent, an enrichment tag, or an isotope tag covalently bound to the protein conjugate via a triazole linker has a structure of formula (I-a1), (I-b1), (II-a1), (II-b1), (III-a1), (III-b1), (IV-a1), or (IV-b1):

-continued (II-b1)
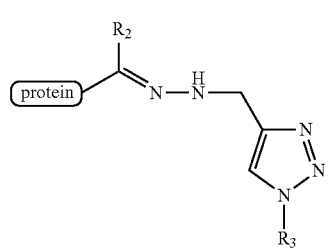

(III-a1)
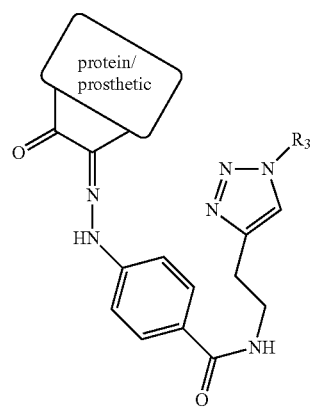

(III-b1)
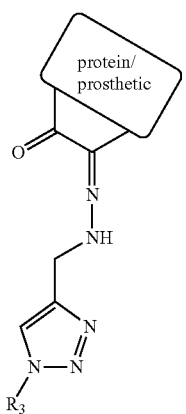

(IV-a1)
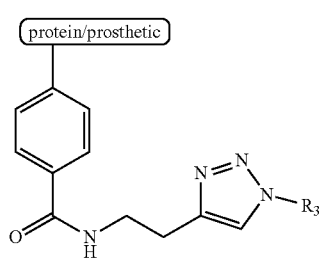

(IV-b1)
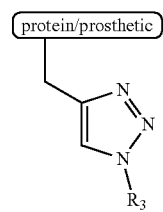

wherein Y is carbon or sulfur; and $R_3$ is an imaging agent, enrichment tag, isotope tag, drug, or radioisotope optionally bound to a metal chelator, or metal chelator optionally bound to a radioisotope. The imaging agent, enrichment tag, isotope tag, drug or radioisotope optionally bound to a metal chelator, or metal chelator optionally bound to a radioisotope, can be directly bound to the triazole moiety, or bound via an optional linker or spacer group. Examples of linker or spacer groups include, but are not limited to, peptide linkers, alkyl groups, polyethylene glycol linkers, and the like.

A protein conjugate of the invention can be present in a proteomic mixture, or it can be isolated or purified, meaning that it is essentially free from other proteins and/or cellular components. A protein conjugate of the invention can be formed in situ or in vivo. Thus, in some embodiments, a protein conjugate of the invention is in a living cell or living organism.

In particular embodiments, the protein of a protein conjugate of the invention is selected from the group consisting of those proteins listed in Tables 1 and 3, and more preferably selected from the group consisting of those proteins listed in Table 2.

Other aspects of the invention relate to a composition comprising cells and at least one probe, wherein the at least one probe comprises a hydrazine moiety or oxyamine moiety and an alkyne moiety. Yet other aspects of the invention relate to a kit comprising:
  (i) a probe comprising a hydrazine moiety or oxyamine moiety and an alkyne moiety; and
  (ii) an azide-modified tag.

The methods and protein conjugates of the invention can be used in a wide range of applications in basic and clinical biology. For example, the methods of the invention can be used to identify proteins modifications, particularly electrophilic PTMs and oxidative PTMs, de novo. The methods of the invention can also be used to quantify occupancies of such protein modifications and activities in native biological systems. The methods of the invention can also be used to study the etiology of diseases and identify new therapeutic targets by increasing our understanding of how protein electrophiles affect disease states. The methods can be used to identify an electrophilic PTM or protein(s) with electrophilic PTMs associated with a disease by comparing the PTM profile of a cell or biological sample from a patient having a disease or suspected of having a disease with the PTM profile of a cell or biological sample from a healthy individual.

Embodiments

Embodiment 1 is a method for detecting an electrophilic post-translational modification (PTM) or oxidative PTM of at least one protein in a proteomic mixture, the method comprising:
  (i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the at least one protein, thereby forming a mixture comprising at least one alkyne-derivatized protein;
  (ii) labeling the at least one alkyne-derivatized protein with an azide-modified tag, optionally in the presence of a copper catalyst, to obtain at least one labelled protein; and
  (iii) analyzing the at least one labelled protein to thereby detect the PTM of the at least one protein.

Embodiment 2 is the method of embodiment 1, further comprising enriching the at least one labelled protein from the proteomic mixture.

Embodiment 3 is the method of embodiment 1 or embodiment 2, further comprising identifying the at least one labelled protein from the proteomic mixture, preferably wherein the method of identification comprises mass spectrometry.

Embodiment 4 is a method for profiling an electrophilic post-translational modification (PTM) of at least one protein in a proteomic mixture, the method comprising:
(i) contacting the proteomic mixture with a probe comprising a hydrazine or oxyamine moiety and an alkyne moiety to form a covalent linkage between the hydrazine or oxyamine moiety of the probe and the electrophilic PTM or oxidative PTM of the at least one protein to obtain at least one alkyne-derivatized protein;
(ii) labeling the at least one alkyne-derivatized protein with an azide-modified tag, optionally in the presence of a copper catalyst, to obtain at least one labelled protein;
(iii) enriching the at least one labelled protein; and
(iv) quantifying the at least one labelled protein.

Embodiment 5 is the method of any one of embodiments 1 to 4, wherein the tag is an imaging agent, enrichment tag, an isotope tag, degradation tag, or chemical or enzymatic cleavage tag.

Embodiment 6 is the method of any one of embodiments 1 to 5, wherein the alkyne moiety of the probe is a terminal alkyne.

Embodiment 7 is the method of any one of embodiments 1 to 6, wherein the electrophilic post-translational modification is a carbonyl containing modification or ester containing modification, such as a pyruvoyl modification, glyoxylyl modification, formylglycyl modification, aspartimide modification, aspartyl phosphate modification or quinone modification.

Embodiment 8 is the method of any one of embodiments 1 to 6, wherein the oxidative PTM is a Flavin cofactor, heme iron cofactor, or non-heme iron cofactor.

Embodiment 9 is the method of any one of embodiments 1 to 8, wherein the at least one protein is selected from a protein listed in Tables 1 and 3, and more preferably Table 2.

Embodiment 10 is the method of any one of embodiments 1 to 9, wherein the proteomic mixture is in a living cell.

Embodiment 11 is a protein conjugate comprising a structure of formula (I), formula (II), formula (III), or formula (IV):

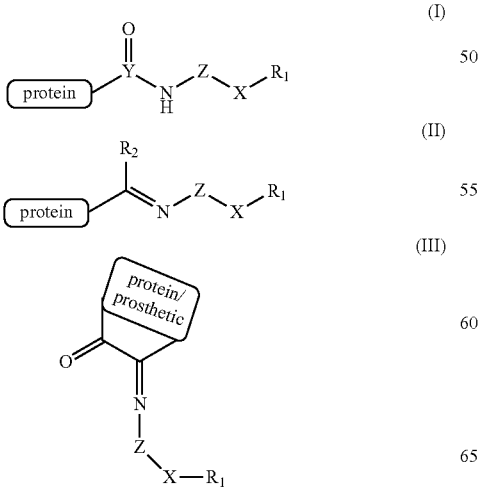

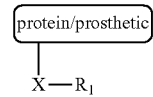

wherein $R_1$ is an alkyne; $R_2$ is hydrogen or alkyl, preferably methyl; Y is carbon or sulfur; X is a linker; and Z is NH or oxygen.

Embodiment 12 is the protein conjugate of embodiment 11, wherein the protein conjugate comprises a structure of formula (I-a), formula (I-b), formula (II-a), formula (II-b), formula (III-a), formula (III-b), formula (IV-a), or formula (IV-b):

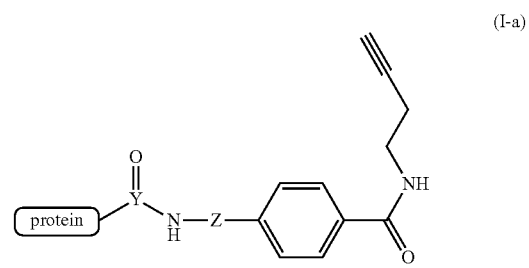

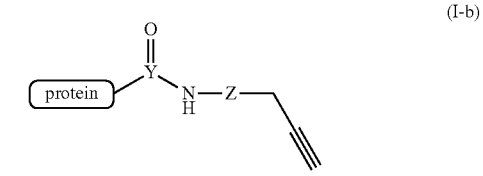

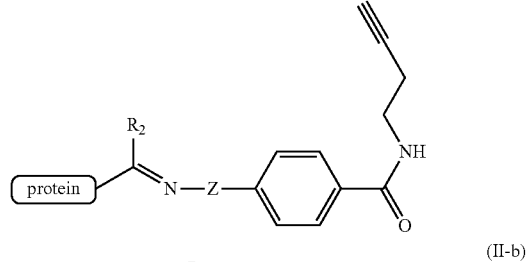

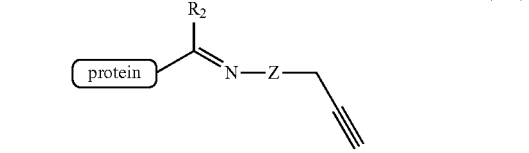

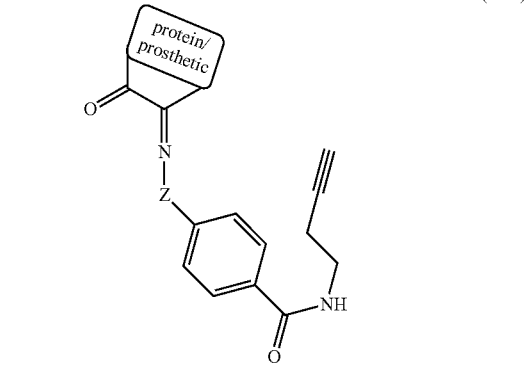

(III-b)

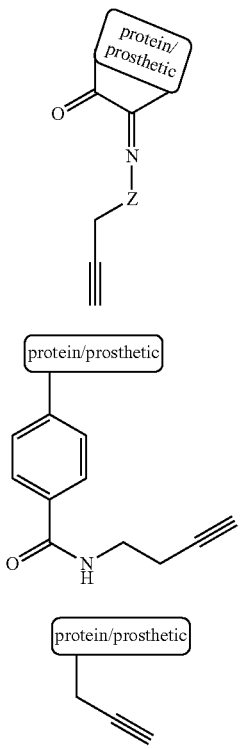

(IV-a)

(IV-b)

wherein $R_2$ is hydrogen or alkyl, preferably methyl; Y is carbon or sulfur; and Y is O or NH.

Embodiment 13 is the protein conjugate of embodiment 11 or 12, further comprising an imaging agent, an enrichment tag, an isotope tag, degradation tag, chemical or enzymatic cleavage tag, drug, or radioisotope optionally bound to a metal chelator, or metal chelator optionally bound to a radioisotope, covalently bound to the protein conjugate via a triazole linker.

Embodiment 14 is the protein conjugate of embodiment 13, wherein the protein conjugate comprises a structure of formula (I-a1), (I-b1), (II-a1), (II-b1), (III-a1), (III-b1), (IV-a1), or (IV-b1):

(I-a1)

(I-b1)

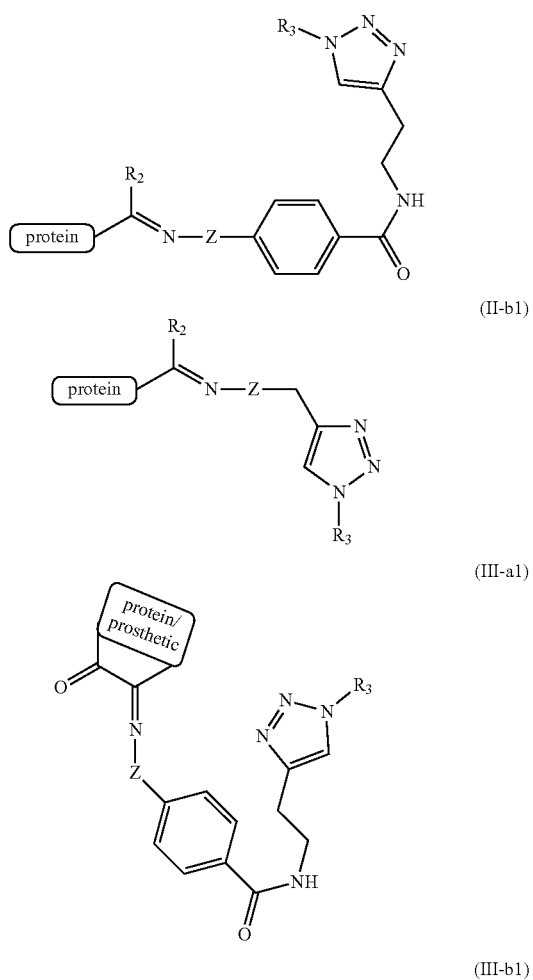

(II-a1)

(II-b1)

(III-a1)

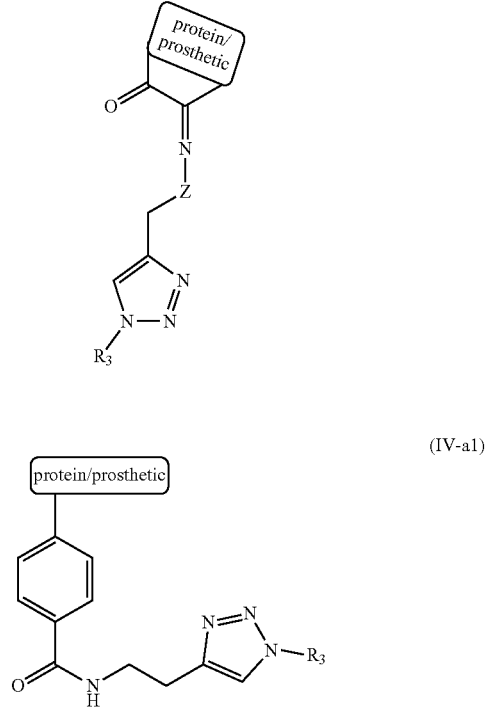

(III-b1)

(IV-a1)

-continued

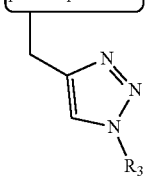
(IV-b1)

wherein Y is carbon or sulfur; Z is NH or O; and R₃ is an imaging agent, enrichment tag, isotope tag, degradation tag, chemical or enzymatic cleavage tag, drug or radioisotope optionally bound to a metal chelator, or metal chelator optionally bound to a radioisotope, optionally bound to the triazole moiety via a linker.

Embodiment 15 is the protein conjugate of any one of embodiments 11 to 14, wherein the protein conjugate is present in a cell, preferably a living cell or living organism.

Embodiment 16 is the protein conjugate of any one of embodiments 11 to 14, wherein the protein is selected from the group consisting of proteins listed in Tables 1 and 3, more preferably a protein selected from the group consisting of amyloid precursor proteins, KEAP1, LGMN, FTO and other Fe/2OG enzymes, AMD1, SCRN2/3, and MAO.

Embodiment 17 is a composition comprising cells, for instance living cells, and at least one probe comprising a hydrazine moiety or oxyamine moiety and an alkyne moiety.

Embodiment 18 is the composition of embodiment 17, wherein the at least one probe is:

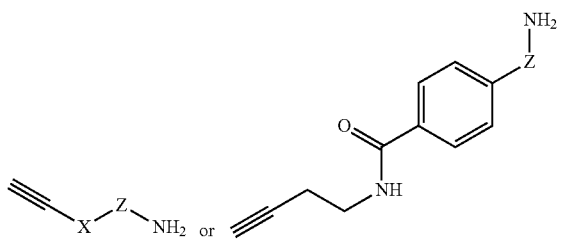

wherein X is a linker; and Z is oxygen or NH; preferably wherein the at least one probe is

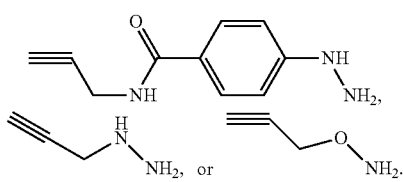

Embodiment 19 is a probe having a structure of:

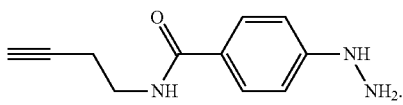

Embodiment 20 is a method of modifying an electrophilic post-translation modification (PTM) or oxidative PTM with an alkyne group, the method comprising contacting the protein with a probe comprising a hydrazine or oxyamine moiety and an alkyne moiety to form a covalent linkage between the hydrazine or oxyamine moiety of the probe and an electrophilic PTM or oxidative PTM of the protein, thereby forming a protein comprising an alkyne modification.

Embodiment 21 is the method of embodiment 20, further comprising reacting the protein comprising an alkyne modification with an azide-modified tag.

Embodiment 22 is the method of any one of embodiments 1-10, wherein the labelled protein is isotopically labelled and detected or quantified by mass spectrometry, preferably multidimensional liquid chromatography-tandem mass spectrometry (LC-MS/MS).

Embodiment 23 is the method of embodiment 22, wherein the LC-MS/MS is combined with SILAC (stable isotope labelling by amino acids in cell culture) methodology.

Embodiment 24 is the method of any one of embodiments 1-10, wherein the labelled protein is detected, identified, or quantified by a method comprising:
(i) labeling the alkyne-derivatized protein with isotopically heavy and light biotin-TEV-azide;
(ii) enriching the biotin-labelled protein on streptavidin beads;
(iii) digesting the biotin-labelled protein on bead with trypsin, such that only probe-modified peptide fragments remain on bead;
(iv) further digesting the probe-modified peptide fragments on bead with TEV protease to release the probe-labelled peptide fragment; and
(v) analyzing the released probe-labelled peptide fragment by LC-MS/MS.

Embodiment 25 is the method of any one of embodiments 1-10 and 20-24, wherein the probe is:

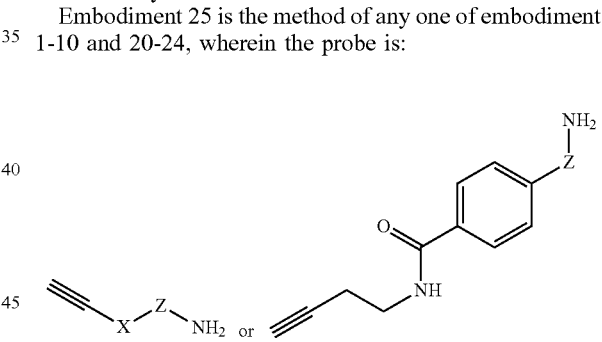

wherein X is a linker; and Z is oxygen or NH; preferably wherein the probe is

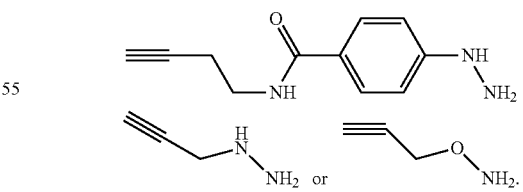

Embodiment 26 is the method of any one of embodiments 1-10 and 20-25, wherein the azide modified tag is biotin-azide or rhodamine-azide.

Embodiment 27 is a kit comprising:
(iii) a probe comprising a hydrazine or oxyamine moiety and an alkyne moiety; and
(iv) an azide-modified tag.

Embodiment 28 is the kit of embodiment 27, wherein the probe is:

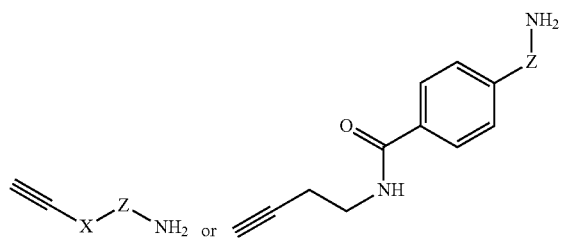

wherein X is a linker; and Z is oxygen or NH; preferably wherein the probe is,

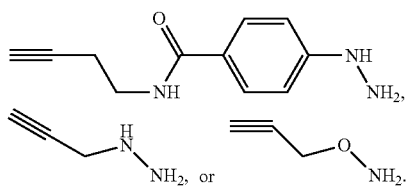

Embodiment 29 is the kit of embodiment 27 or embodiment 28, wherein the azide-modified tag is biotin-azide or rhodamine-azide.

Embodiment 30 is the method of embodiment 26 or the kit of embodiment 29, wherein the biotin-azide tag is isotopically labelled.

Embodiment 31 is the method or kit of any one of embodiments 26, 29, and 30, wherein the biotin-azide tag comprises an enzymatic cleavage site, preferably a TEV cleavage site.

Embodiment 32 is the kit of embodiment 31, further comprising TEV protease.

Embodiment 33 is the method of any one of embodiments 1 to 10 and 22 to 26, further comprising characterizing the electrophilic or oxidative PTM.

Embodiment 34 is a method of inhibiting a function or activity of a protein by targeting an electrophilic post-translation modification (PTM) or oxidative PTM of the protein, the method comprising contacting the protein with a probe comprising a hydrazine or oxyamine moiety and an alkyne moiety to form a covalent linkage between the hydrazine moiety of the probe and the electrophilic PTM or oxidative PTM of the protein, and optionally further reacting the protein with an azide-modified tag, thereby inhibiting the function or activity of the protein.

Embodiment 35 is the method of embodiment 34, wherein the protein is present in a proteomic mixture, preferably wherein the proteomic mixture is in a living cell.

The method of embodiment 34 or 35, wherein the protein is an enzyme.

The method of embodiment 34 or 35, wherein the function or activity of the protein is an enzymatic activity, for instance biochemical activity or native (endogenous) physiological function.

EXAMPLES

The following examples of the invention are to further illustrate the nature of the invention. It should be understood that the following examples do not limit the invention and that the scope of the invention is to be determined by the appended claims.

Example 1: Synthesis of "Clickable" Hydrazine Probes

Materials

All chemicals were obtained from commercial suppliers and were used without further purification. Merck silica gel TLC plates (0.25 mm, 60 F254) were used to monitor reaction progress. Flash chromatography was performed using SiliaFlash F60 silica gel (40-63 am, 60 Å) or Silicycle SiliaBond Silver Nitrate (10% $AgNO_3$, 40-63 μm, 60 Å). Nuclear magnetic resonance (NMR) spectra were recorded at room temperature on a Varian Inova-400 instrument. Chemical shifts are normalized to the residual solvent peak and reported with the following notation: chemical shift (6 in ppm), multiplicity (s=singlet, bs=broad singlet, d=doublet, t=triplet, q=quartet, m=multiplet, bm=broad multiplet), and coupling constant (J, in Hz). High-resolution mass spectra (HRMS) were recorded on an Agilent Mass spectrometer using ESI-TOF (electrospray ionization-time of flight).

Synthesis of Probe 1

Probe 1 was synthesized according to the following reaction scheme, as described previously[87]:

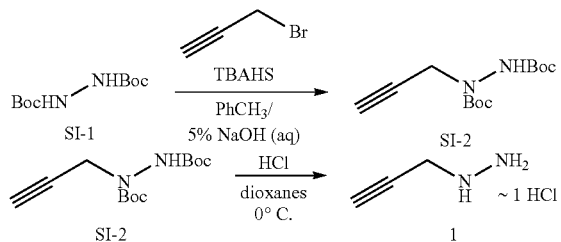

Synthesis of di-tert-butyl 1-(prop-2-yn-1-yl)hydrazine-1,2-dicarboxylate (SI-2)

Sodium hydroxide (5% aqueous solution (w/v); 1.98 g, 43 mmol), tetrabutylammonium hydrogen sulfate (TBAHS; 170 mg, 0.5 mmol), and 3-bromoprop-1-yne (80% wt. solution in toluene; 6 mL, 67 mmol) were added to a stirring solution of SI-1 (di-tert-butyl hydrazine-1,2-dicarboxylate; 5 g, 22 mmol) in toluene. The reaction was complete after about 19 hours, as monitored by thin layer chromatography (TLC) developed in 10% ethyl acetate/hexanes and detected with potassium permanganate ($KMnO_4$) stain. The starting material was completely consumed as judged by the increased $R_f$ value for the product ($R_f$(SI-1)<$R_f$(SI-2)<0.5). The reaction was quenched with water (200 mL) and transferred to a separatory funnel. The product was extracted with ethyl acetate (3×200 mL) and washed once with brine (100 mL). The organic layers were combined, dried over anhydrous sodium sulfate, and concentrated under vacuum. The residue was purified by $SiO_2$ flash chromatography (10-20% ethyl acetate/hexanes) providing SI-2 as a white powder (di-tert-butyl-1-(prop-2-yn-1-yl)hydrazine-1,2-dicarboxylate; 3.4 g, 13 mmol, 60% yield). $^1$H NMR (400 MHz, $CDCl_3$) (75:25 mixture of rotamers[87], peak corresponding to minor rotamer starred) δ 6.59 (bs, 0.75H), 6.32 (bs, 0.25H)*, 4.23 (s, 2H), 2.22 (t, J=2.4 Hz, 1H), 1.43 (s, 18H); $^{13}$C NMR (151 MHz) δ 155.04, 81.77, 79.06, 72.46, 39.56, 28.50.

Synthesis of prop-2-yn-1-ylhydrazine hydrochloride (1)

HCl in 1,4-dioxane (4 N, 8.75 mL, 5 eq.) was added dropwise to SI-2 (1.9 g, 7.1 mmol, 1 eq.) while stirring on ice. The reaction was stirred at room temperature overnight and concentrated under vacuum the following day. The resulting yellow crystals were dissolved in a minimum volume of methanol. Diethyl ether was then added to precipitate the product. The white precipitate was filtered, washed with diethyl ether and dried under vacuum to yield probe 1 (prop-2-yn-1-ylhydrazine hydrochloride, 335 mg, 3.13 mmol, 44% yield). The stoichiometry of the hydrazinium chloride (mono or di) was determined based on the titrated equivalents of sodium hydroxide required to achieve neutral pH of the working stock solution. The probe was dissolved in H$_2$O and the solution was neutralized by addition of 1-1.5 equivalents of base. $^1$H NMR (400 MHz, CD$_3$OD) δ 3.81 (d, J=2.55 Hz, 2H), 2.99 (t, J=2.47 Hz, 1H); $^{13}$C NMR (151 MHz, CD$_3$OD) δ 77.21, 77.17, 40.20; MS (ESI+) m/z calc'd for C$_3$H$_7$N$_2$$^+$[M+H]$^+$: 71.0604, found 71.0607.

Synthesis of Probe 2

Probe 2 was synthesized according to the following reaction scheme:

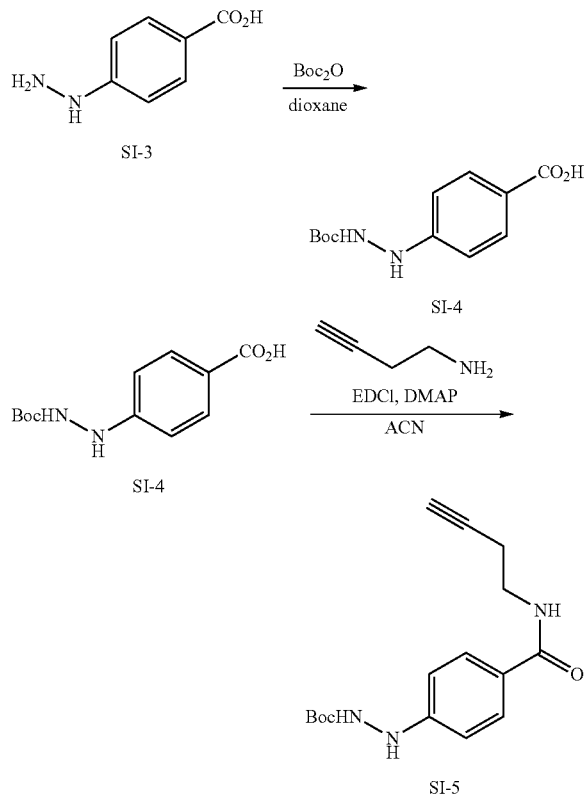

Synthesis of 4-(2-(tert-butoxycarbonyl)hydrazinyl)benzoic acid (SI-4)

Di-tert-butyl dicarbonate (8.80 g, 40 mmol, 2 eq.) was added to a solution of SI-3 (4-hydrazinylbenzoic acid; 3.08 g, 20 mmol, 1 eq.) in 1,4-dioxane (40 mL, 0.5 M) at room temperature and the mixture was stirred overnight. The following day, the reaction was diluted with ethyl acetate (100 mL) and transferred to a separatory funnel. The product was extracted with 1 M sodium hydroxide (3×50 mL), the aqueous layers were combined and acidified with 12 M hydrochloric acid, and the resulting suspension was extracted with ethyl acetate (3×50 mL). The combined organic layers were washed once with brine (100 mL), dried over magnesium sulfate, filtered and concentrated to yield SI-4 as an off-white powder [4-(2-(tert-butoxycarbonyl)hydrazinyl)benzoic acid; 4.68 g, 18.5 mmol, 92% yield]. The product was sufficiently pure by $^1$H NMR to be carried over to the next step without additional purification. Alternatively, SI-4 is commercially available as a starting material, and can thus be obtained from several commercial sources (e.g. Chem-Impex International, Inc.).

Synthesis of tert-butyl 2-(4-(but-3-yn-1-ylcarbamoyl)phenyl)hydrazine-1-carboxylate (SI-5)

1-ethyl-3-(3-dimethylaminopropyl)carbodiimide (EDCI; 3.6 g, 18.8 mmol, 1 eq.), but-3-yn-1-amine (3.0 mL, 36.5 mmol, 2 eq.), and 4-(dimethylamino)pyridine (DMAP; 110 mg, 0.9 mmol, 0.05 eq.) were added to a solution of SI-4 (4-(2-(tert-butoxycarbonyl)hydrazinyl) benzoic acid; 4.68 g, 18.5 mmol, 1 eq.) in acetonitrile (93 mL, 0.2 M). The reaction was stirred at room temperature overnight and concentrated under vacuum the following day. The resulting residue was re-dissolved in 200 mL ethyl acetate and subsequently washed with 1 M hydrochloric acid, 1 M sodium hydroxide and brine (2×50 mL each). The organic layer was dried over magnesium sulfate, filtered and concentrated. The resulting orange crystals were triturated with cold dichloromethane to afford SI-5 as white crystals (tert-butyl 2-(4-(but-3-yn-1-ylcarbamoyl)phenyl)hydrazine-1-carboxylate; 3.2 g, 10.5 mmol, 57% yield). $^1$H NMR (400 MHz, CD$_3$OD) δ 7.70 (d, J=8.70 Hz, 2H), 6.79 (d, J=8.95 Hz, 2H), 3.50 (t, J=7.16 Hz, 2H), 2.49 (td, J=2.60 Hz, J=7.14 Hz, 2H), 2.30 (t, J=2.77 Hz, 1H), 1.51 (s, 9H); $^{13}$C NMR (151 MHz, CD$_3$OD) δ; 170.21, 158.73, 153.83, 129.69, 125.51, 125.06, 112.34, 82.34, 70.71, 39.99, 28.63, 19.94.

Synthesis of N-(but-3-yn-1-yl)-4-hydrazinylbenzamide hydrochloride (2)

Acetyl chloride (357 μL, 5 mmol, 5 eq.) was added dropwise to methanol (5 mL) at 0° C. The resulting methanolic HCl (1 M) was mixed with SI-5 (tert-butyl 2-(4-(but-3-yn-1-ylcarbamoyl)phenyl)hydrazine-1-carboxylate; 303.9 mg, 1 mmol, 1 eq.). The reaction was stirred overnight at room temperature and concentrated under a stream of nitrogen the following day. The resulting red crystals were re-dissolved in a minimum amount of methanol (ca. 2 mL). Diethyl ether was then added (ca. 4 mL) until a precipitate began to form, at which point the solution was cooled to −20° C. overnight. The resulting white precipitate was filtered, washed with diethyl ether, and dried under vacuum to yield probe 2 as an off-white powder (N-(but-3-yn-1-yl)-4-hydrazinylbenzamide; 177.5 mg, 0.74 mmol, 74% yield). The stoichiometry of the hydrazinium chloride (mono or di)

was determined based on the titrated equivalents of sodium hydroxide required to achieve neutral pH. The probe was dissolved in $H_2O$ and the stock solution was neutralized by addition of 1-1.3 equivalents of base. $^1H$ NMR (400 MHz, $CD_3OD$) δ 7.84 (d, J=8.69 Hz, 2H), 7.00 (d, J=8.76 Hz, 2H), 3.51 (t, J=7.33 Hz, 2H), 2.50 (td, J=2.47 Hz, J=7.23 Hz, 2H), 2.31 (t, J=2.53 Hz, 1H); $^{13}C$ NMR (151 MHz, $CD_3OD$) δ; 169.43, 149.32, 129.96, 129.12, 114.50, 82.24, 70.78, 40.04, 19.84; MS (ESI+) m/z calc'd for $C_{13}H_{22}N_2O_4$ [M+H]+: 204.1131, found 204.1133.

Example 2: In Situ Profiling with Hydrazine Probes in Human Cells

Propargyl hydrazine (probe 1) and a phenyl hydrazine derivative (probe 2), synthesized as described in Example 1, were used as nucleophilic probes to capture protein-bound electrophiles in cells. Propyl hydrazine dihydrochloride (3) and phenyl hydrazine hydrochloride (4) used as non-clickable competitor probes were purchased from Matrix Scientific and Sigma, respectively. Working stock solutions of the clickable hydrazine probes and non-clickable competitor probes (~0.2-3 M) were prepared in $H_2O$ from the hydrazinium chloride salts, with the exception of probes 2 and 4 which contained 10% DMSO. The pH was titrated to 6.5-7 with concentrated sodium hydroxide using Colorphast pH indicator strips from pH 5-10 with 0.5 pH unit accuracy (EMD). Solutions were stored in aliquots at −80° C. for several months.

Cell Culture

Low-passage human embryonic kidney (HEK293T) adherent cell line (ATCC) was grown at 37° C. in a humidified 5% $CO_2$ atmosphere and expanded in high-glucose DMEM supplemented with 10% (v/v) fetal bovine serum (FBS), penicillin (100 U/mL), streptomycin (100 μg/mL) and L-glutamine (2 mM).

In Situ Labelling of Cells with Hydrazine Probes

For gel-based experiments, cells were plated and grown to near complete confluence at the time of treatment. Cells were washed with cold phosphate buffered saline (PBS, pH 7.4) and replenished with serum-free DMEM (~15% of normal passage volume, e.g. a 10 cm plate normally passaged with 10 mL media received 1.5 mL) supplemented with 10 mM Na-HEPES buffer (pH 7.5). Unless otherwise indicated, cells were incubated with probes (3 mM and 1 mM for probes 1 and 2, respectively) in the absence or presence of 10-fold excess non-clickable competitor probes (30 mM and 10 mM for 3 and 4, respectively) for 0.5 hour at 37° C. When applicable, probe and competitor were premixed before co-administering to the cells.

The cells were lysed, and the cell proteomes were conjugated to a rhodamine-azide ($Rh-N_3$) reporter tag.

Effects of In Situ Probe Treatment on pH and Cell Viability

Working stock solutions of probes and competitors were neutralized prior to treatment and media was supplemented with 10 mM Na-HEPES (pH 7.5) to enhance the buffer capacity to ensure the pH was maintained. The phenol red pH indicator of the media confirmed that there was no substantial change in pH during the treatment. Cell viability was quantified based on ATP levels in the absence and presence of probe 1 with or without competitor probe 3 using the CellTiter-Glo luminescence assay (Promega). Trypsinized HEK293T cells were diluted in serum-free DMEM supplemented with 10 mM Na-HEPES to a final concentration of 0.8 million cells/mL. To a cell culture microplate (Greiner Bio-One No. 655098; white, 96-well, 34 $mm^2$ growth area per well, Clear bottom), 80,000 cells (100 μL of cell suspension) were plated per well. Untreated wells were compared to those treated with probe 1 (3 mM) in the absence or presence of competitor probe 3 (30 mM). Following a 1 hour incubation at 37° C., an equal volume of CellTiter-Glo solution was added to each well. After 20 minutes at ambient temperature, luminescence was measured on a Biotech Synergy 4 plate reader. Well luminescence, in relative light units (RLU), under each condition (n=4 of each) was measured to determine cell viability according to the formula: $I_{untreated}$, $I_{probe\ 1}$, and $I_{probe\ 1/competitor\ 3}$=(132±2, 139±2, and 134±1)×$10^3$ RLU. "$I_{untreated}$" refers to the intensity of luminescence of untreated cells; and "$I_{probe\ 1}$" refers to the intensity of luminescence of probe-1 treated cells.

Proteome Preparation

Cell pellets were resuspended on ice in PBS (100-500 μL) and lysed by a Branson Sonifier probe sonicator (2×6-10 pulses, 50% duty cycle, output setting=3-5). The resuspension volume and sonication power was adjusted accordingly for the cell pellet yield. Soluble and membrane proteomes were separated by ultracentrifugation (100,000 g, 30-45 min). Protein concentrations of each fraction were determined using the DC protein assay (Bio-Rad), similar to the Lowry assay, on a microplate reader (Tecan, Infinite F500). In general, samples for gel-based experiments, as described below, required confluent cells harvested from a 6-well plate (3.5 cm growth diameter).

Gel-Based Analysis of Probe-Labelled Proteins

Soluble proteomes from treated cells were diluted to 1 mg/mL. To each sample (50 μL), a freshly prepared "click" or CuAAC reagent mixture (6 μL) containing 0.1 mM tris(benzyltriazolylmethyl)amine (TBTA) (3 μL/sample, 1.7 mM in 4:1 DMSO:t-BuOH), 1 mM $CuSO_4$ (1 μL/sample, 50 mM in $H_2O$), 25 μM azide-rhodamine (1 μL/sample, 1.25 mM in DMSO), and freshly prepared 1 mM tris(2-carboxyethyl)phosphine (TCEP) (1 μL/sample, 50 mM in PBS or $H_2O$) was added to conjugate the fluorophore to probe-labelled proteins. TBTA was purchased from TCI and azide-rhodamine was synthesized as previously described[64]. Upon addition of the click mixture, each reaction was immediately mixed by vortexing and then allowed to react at ambient temperature for 1 hour before quenching the reactions with SDS loading buffer (4× stock, 17 μL). Proteins (~25 μg total protein loaded per gel lane) were resolved by SDS-PAGE (10% acrylamide) and visualized by in-gel fluorescence scanning on a Hitachi FMBIO-II or BioRad ChemiDoc MP flatbed fluorescence scanner.

Results

The hydrazine served as a reactive nucleophile and the alkyne as a latent affinity handle for conjugation by Cu(I)-catalyzed azide-alkyne cycloaddition (CuAAC, or 'click' chemistry)[19] to azide reporter tags for protein detection, enrichment, and identification[20]. Concentration-dependent protein labeling was observed in cells treated with the clickable hydrazine probes 1 and 2 (FIGS. 2A-2D). Protein labeling was suppressed by increasing concentrations of co-administered non-clickable hydrazine probe 3 (FIG. 1A). Protein staining did not reveal any obvious changes in the expression or abundance of proteins in cells treated with probe 1 (FIGS. 2A-2D). Cell viability assays, performed as described above, confirmed that the hydrazine probes were not toxic to cells under these conditions.

Example 3: Identification of Proteins Modified by Hydrazine Probes

Proteins modified, or labelled, by probe 1 were identified using multidimensional liquid chromatography-tandem mass spectrometry (LC/LC-MS/MS)[23] combined with SILAC (Stable Isotopic Labeling of Amino acids in Cell culture) methodology[24], as schematically illustrated in FIG. 3A. Briefly, cells were grown in medium containing either natural abundance lysine and arginine ('light') or $^{13}$C- and $^{15}$N-enriched amino acid isotopologues ('heavy') and subject to different probe treatment conditions followed by lysis, combination, conjugation to a biotin-azide reporter tag, enrichment by streptavidin chromatography, and quantitative proteomic analysis. MS1 and MS2 data provided information on the relative quantity and identity of enriched proteins, respectively[25].

Cell Culture

HEK293 cells and low-passage human breast cancer (MDA-MB-231) adherent cell lines (ATCC) were grown as described in Example 2. For standard SILAC (Stable Isotope Labelling by Amino acids in Cell culture) experiments[62,63], each cell line was passaged a minimum of six times in lysine- and arginine-free DMEM (Thermo Fisher Scientific, 89985) containing dialyzed FBS (Gemini) supplemented with either isotopically enriched L-[$^{13}$C$_6$$^{15}$N$_2$]lysine hydrochloride and L-[$^{13}$C$_6$$^{15}$N$_4$]arginine hydrochloride or natural abundance isotopologues (100 μg/mL each, 550 μM and 475 M, respectively, Sigma).

In Situ Labelling of Cells with Hydrazine Probes for MS Experiments

For MS-based experiments, labelling was performed in a similar manner as described above in Example 2, maintaining the same concentrations of probes. Modifications to this protocol included using isotopically 'light' and 'heavy' SILAC cells that were also grown to near complete confluence prior to treatment. Isotopically light cells were treated with the non-clickable hydrazine probe (at the same concentration as the probe in 'enrichment' experiments) or the probe in the presence of 10-fold excess non-clickable hydrazine probe as a competitor (in 'competition' experiments). Isotopically heavy cells were treated with the probe for both types of experiments. These treatments were performed in non-SILAC media. Following treatments, cells were washed with cold PBS to remove the probe-containing media, harvested by scraping, collected by centrifugation (1,400 g, 3 min, 4° C.), washed again by resuspension in cold PBS and frozen as pellets at −80° C. until use.

Proteome Preparation for MS-Based Experiments

The proteome was prepared for MS-based experiments as described above in Example 2. For SILAC experiments, isotopically heavy and light whole cell lysates were mixed in equal proportions prior to fractionation of membrane and cytosolic (soluble) components. In general, samples for MS-based experiments, as described below, required confluent cells harvested from one to two 10-15 cm dishes.

MS-Based Quantitative Analysis of Probe-Labelled Proteins

The fractionated equimolar mixture of heavy and light soluble proteomes (1-1.5 mg) was diluted to 1 mL in PBS. Click reactions were scaled accordingly (except for biotin-azide) to maintain final concentrations of 0.1 mM TBTA, 1 mM CuSO$_4$, 100 μM biotin-azide (10 mM in DMSO) and 1 mM TCEP. The mixture was vortexed and placed on a rotator at ambient temperature for 1 hour. Sequential addition of and mixture with pre-chilled methanol (MeOH, 2 mL), chloroform (CHCl$_3$, 0.5 mL) and PBS (1 mL) on ice quenched the reaction. The precipitated proteome was centrifuged (5,000 g, 10 min, 4° C.) to fractionate the protein interphase from the organic and aqueous solvent layers. The protein pellet was washed with cold 1:1 MeOH:CHCl$_3$ (3×1 mL), mildly sonicated in cold 4:1 MeOH:CHCl$_3$ (2.5 mL) and pelleted once more by centrifugation (5,000 g, 10 min, 4° C.) to ensure click reagents were efficiently removed.

The remaining protein precipitate was redissolved by mild sonication in a freshly prepared solution of proteomics-grade urea (500 μL, 6 M in PBS). Disulfides were reduced with TCEP (9 mM) pre-neutralized with potassium carbonate (27 mM) for 30 minutes at 37° C. Reduced thiols were then alkylated by iodoacetamide (45 mM) for 30 minutes at ambient temperature protected from light. SDS (2% (w/v)) was added to ensure complete denaturation. The solution was diluted to ~0.2% SDS with PBS (~5 mL) and incubated with pre-equilibrated streptavidin agarose resin (50 μL column volume, 100 μL 1:1 slurry, Pierce) for ~1.5-2 hours at ambient temperature on a rotator. The streptavidin beads were collected by centrifugation (1,400 g, 1-2 min) and sequentially washed with 0.2% SDS in PBS (3×~10 mL), detergent-free PBS (3×~10 mL) and H$_2$O (3×~10 mL) to remove unbound protein, excess detergent, and small molecules. The resin was transferred to a Protein LoBind tube (Eppendorf or BioPioneer) and bound proteins were digested on-bead overnight at 37° C. in about 200 μL total volume containing sequencing grade porcine trypsin (2 μg, Promega) in the presence of urea (2 M in PBS) and CaCl$_2$ (1 mM). The proteolyzed supernatant was transferred to a fresh Protein LoBind tube, acidified with formic acid (5%) to inactivate trypsin, and stored at −80° C. until analyzed.

Liquid Chromatography-Tandem-Mass Spectrometry (LC-MS/MS) Analysis of Tryptic Digests Tryptic digests were analyzed as described previously[69]. In brief, tryptic digests were pressure loaded onto a 250 m (inner diameter) fused silica capillary column packed with C18 resin (~4 cm, Aqua 5 m, Phenomenex). Samples were analyzed using an LTQ-Orbitrap Velos mass spectrometer (Thermo Scientific) coupled to an Agilent 1200 series quaternary pump. Peptides were eluted by two-dimensional separation on a column with a 5 μm tip (100 μm fused silica, packed with C18 (10 cm) and strong cation exchange (SCX) resin (3 cm, Luna, 5 μm, Phenomenex) using a five-step 'MudPIT' protocol[70] that involves 0%, 25%, 50%, 80% and 100% salt 'bumps' of ammonium acetate (NH$_4$OAc; 500 mM) to elute peptides stepwise from the SCX to the C18 resin followed by an increasing gradient of acetonitrile in each step (5%-100% buffer B in buffer A; buffer A: 95% H$_2$O, 5% acetonitrile, 0.1% formic acid; buffer B: 20% H$_2$O, 80% acetonitrile, 0.1% formic acid). The flow rate through the column was 0.25 μl/min and the voltage applied to the nano-LC electrospray ionization source was 2.5 kV. Spectra were collected in a data-dependent acquisition mode such that each scan cycle involved a single high-resolution (30, 000) full MS spectrum of parent ions (MS1 scan from 400-1800 m/z) collected in the orbitrap coupled to 30 CID-induced fragmentation (MS2) scans in the ion trap of the 30 most abundant parent ions from the MS1 scan. Dynamic exclusion (repeat count of 1, exclusion duration of 20 s) and monoisotopic precursor selection were enabled. Parent ions with unassigned or +1 charge states by the instrument were excluded for fragmentation. All other parameters were left as default values.

Peptide Identification

The MS2 spectra for all fragmented parent ions were extracted using RawXtract (version 1.9.9.2; 2004 release; publically available from Scripps Research Institute) or RawConverter[71] with monoisotopic selection (2015 released; publically available from Scripps Research Institute). Each MS2 spectra was searched using the ProLuCID algorithm against a reverse-concatenated, nonredundant database of the human proteome (Uniprot release—11/05/2012) and filtered using DTASelect 2.0 within the Integrated Proteomics Pipeline (IP2) software. Cysteine residues were searched with a static modification for S-carbamidomethylation (+57.02146). Methionine residues were searched with up to one differential modification for oxidation (+15.9949 Da). Peptides were required to have at least one tryptic terminus but an unlimited number of missed cleavages were allowed in the database search. Each dataset was searched for both light and heavy isotopologues of the same peptide by specifying the mass shift of heavy residues as static modifications on lysine (+8.0142 Da) and arginine (+10.0082 Da) in a coupled 'heavy' search. The parent ion mass tolerance for a minimum envelope of three isotopic peaks was set to 50 ppm, the minimum peptide length was six residues, the false-positive rate was set at 2% or lower and at least two peptides of a protein must be detected in order to be advanced to the next step of analysis.

Peptide and Protein Quantification

Heavy and light parent ion chromatograms associated with successfully identified peptides were extracted and compared using CIMAGE software as previously described[69]. At least one ion of a co-eluting heavy-light pair must be accurately identified from a fragmentation event that occurred within the retention time window (±10 min) of parent ion elution. To ensure that the correct pair of peaks is quantified, chromatograms are extracted within a 10 ppm error tolerance of the predicted m/z, the signal-to-noise ratio must be >2.5 and the 'co-elution correlation score' and 'envelope correlation score' must have $R^2$ values ≥0.8. In addition, peptides detected as 'singletons,' where only the heavy ion of a peptide pair was identified, but for which passed all other filtering parameters, are given a default assigned ratio of '20,' which is defined as any measured ratio that is ≥20.

Determination of High-Reactivity Protein Targets

To further eliminate false positives and any stochastic variability in the data, protein ratios were then determined by the median peptide ratio derived from three or more unique quantified peptides. Protein ratios that complied with these criteria from a single experiment were then averaged with ratios acquired from ≥3 replicates to provide final values for each type of experiment in both cell lines with both probes. Proteins that exhibited final ratios of >5 in enrichment experiments and >4 in competition experiments were considered the most robust targets of the probes. Infrequently detected proteins that failed to be quantified in both enrichment and competition experiments from HEK293T cells were excluded as potential targets (e.g. amyloid-like protein 2 was considered a target of probe 1 but not probe 2, as this protein failed to be quantified in any probe 2 competition experiment albeit having a quantified ratio of 20 in a single corresponding enrichment experiment). Most importantly, there are no robustly measured ratios for proteins identified as probe 1 targets that had measured ratios of ~1 with probe 2. Probe targets in HEK293T and MDA-MB-231 cells represent data combined from ≥3 independent biological replicates with each cell type performed with several independent batches of synthesized probes over a period of almost two years.

Cloning and Mutagenesis

Full-length genes encoding three probe 1- and one probe 2-targeted proteins were amplified from a cDNA library derived from the same low-passage HEK293T cells used for proteomic profiling. The library was generated using Ribozol RNA extraction (Amresco) and iScript reverse transcription (Bio-rad) supermix reagents. The gene products were cloned into mammalian expression vectors containing N- or C-terminal FLAG affinity tags. The gene for S-adenosyl-L-methionine decarboxylase (AMD1 or AdoMetDC) was cloned into pFLAG-CMV-sport6 (N-terminal tag) at NotI and SalI restriction sites. AMD1, Secernin-3 (SCRN3) and fat mass- and obesity-associated Fe(II)- and 20G-dependent dioxygenase (FTO) were cloned into pRK5 (C-terminal tag) at SalI and NotI restriction sites. Kelch-like ECH-associated protein-1 (Keap1) (N-terminal tag), and empty plasmids of pRK5 were gifts. Full sequences of the genes were confirmed. The proteins expressed via transient transfection in HEK293T cells contain an additional 15 amino acids appended to their N-terminal methionine residue or C-terminus (MDYKD4KLKACGR (SEQ ID NO: 43) and A3G4DYKD4K (SEQ ID NO: 44), respectively). The DYKD4K (SEQ ID NO: 42) appendage in each contains the classic FLAG epitope that permits detection by western blotting or purification by affinity chromatography. Mutants of SCRN3 were generated using QuikChange site-directed mutagenesis with primers containing the desired mutations and their respective compliments. The gene for the deletion mutant of SCRN3 with the sequence Met1Cys6-SCRN3 instead of Met1 Glu2Pro3Phe4Ser5Cys6-SCRN3 (SEQ ID NO: 45) was amplified from the wild-type C-terminal FLAG-tagged construct and cloned into the same vector.

Transfection of HEK293T Cells

HEK293T cells were grown to ~40% confluence under standard growth conditions passaged in the appropriate media before adding the appropriate expression vector (control cells ('mock') received an equal amount of the appropriate empty vector) and polyethyleneimine (PEI) 'MAX' (MW 40,000, Polysciences Inc.) as a transfection reagent under standard transfection conditions (3:1 vector/PEI (w/w) ratio). Cells were incubated for ~48 h before labelling in situ. Proteomes were processed for gel- and MS-based experiments as described above and in Example 2.

Western Blotting

After scanning fluorescence, that same gel was transferred to nitrocellulose membrane in Towbin buffer, the membrane was blocked for ~1 hour at ambient temperature with 5% nonfat dry milk (w/v) in Tris-buffered saline with Tween 20 (TBST) and incubated with primary antibodies in the same solution overnight at 4° C. The antibodies included anti-FLAG (1:2500, F1804, Sigma), anti-AdoMetDC (1:500, sc-160951, Santa Cruz Biotechnology) and anti-His6 (1:1000, ab18184, Abcam). The blots were washed (3×5 min, TBST), incubated with secondary antibodies (1:10,000, IRDye 800CW, LICOR) in milk for 1 hour at ambient temperature, washed again (3×5 min, TBST), and visualized on a LICOR Odyssey Scanner.

Results

Two types of experiments were performed—1) direct enrichment of probe 1-labelled proteins from heavy cells in comparison to light control cells treated with the non-clickable hydrazine (3) at the same concentration as 1 (3 mM for 0.5 h); and 2) competition experiments where both heavy and light cells were treated probe 1, but light cells were also treated with 10× competitor 3 (FIG. 3A)—in two different human cell lines (HEK293T cells and the human breast cancer cell line MDA-MB-231). Proteins both substantially enriched ($MS1_{heavy:light}$ ratios >5) and competed by probe 3 ($MS1_{heavy:light}$ ratios >4) were considered candidate targets of probe 1. Both enrichment and competition were required for this analysis so as to focus on proteins that possess electrophilic modifications capable of near-complete reaction with probe 1, thereby avoiding following up on lower stoichiometry adducts that may originate from minor side reactions with weaker electrophilic groups (e.g., sulfenylated cysteines[26,27] or esterified carboxylate side-chains or C-termini[17]). The target list was further refined by requiring that each protein was detected with a minimum of three unique quantified peptides per experiment and by averaging protein ratios across three or more biological replicates per cell line.

Competition versus enrichment data was plotted as shown in FIG. 3B and Table 1 below, illustrating four categories of proteins: (1) a lower left quadrant of unenriched, background proteins; (2) a nearly unoccupied (as expected) upper left quadrant that would designate proteins competed by probe 3, but not enriched by probe 1; (3) a lower right quadrant populated by a substantial number of proteins that were enriched by probe 1, but not competed by probe 3; and (4) an upper right quadrant, which housed ten proteins that showed strong enrichment and competition and were therefore designated as high-reactivity targets of hydrazine probes (Table 2). Representative peptide ratios for three of these high-reactivity proteins from enrichment, competition, and control (where heavy and light cells were treated with equal concentrations of probe 1) experiments are shown in FIG. 3C.

TABLE 1

Average SILAC ratios for probe 1-targeted proteins measured in the indicated cell line and housed in right quadrants of FIG. 3B.

| Uniprot ID | description[§] | enrichment ratio$_{avg}$ | error* | competition ratio$_{avg}$ | error[†] | proteins[‡] | cell line |
|---|---|---|---|---|---|---|---|
| P17707 | AMD1 S-adenosylmethionine decarboxylase | 20 | 0 | 5 | 2 | 1 | HEK293T |
| Q99538 | LGMN Legumain | 20 | — | 18 | 3 | 2 | |
| Q0VDG4 | SCRN3 Secernin-3 | 20 | 0 | 6 | 3 | 4 | |
| Q96FV2 | SCRN2 Secernin-2 | 20 | 0 | 9 | — | 5 | |
| Q5T160 | RARS2 Probable arginine tRNA ligase | 16 | — | 4 | — | 6 | |
| Q14145 | KEAP1 Kelchlike ECHassociated protein 1 | 17 | 4 | 20 | — | 7 | |
| O00754 | MAN2B1 Lysosomal alphamannosidase | 20 | — | 8 | 7 | 3 | MDA- |
| Q06481 | APLP2 Amyloidlike protein 2 | 19 | 2 | 7 | 4 | 8 | MB-231 |
| P05067 | APP Amyloid beta A4 protein | 16 | 3 | 4 | 1 | 9 | |
| Q9UM22 | EPDR1 Mammalian ependyminrelated | 20 | — | 20 | — | 10 | |
| Q6YP21 | CCBL2 Kynurenine oxoglutarate transaminase | 10 | 6 | 4 | 3 | 1 | HEK293T |
| Q7L8L6 | FASTICD5 FAST kinase domain containing | 18 | 2 | 3 | 1 | 2 | |
| P04075 | ALDOA Fructosebisphosphate aldolase A | 16 | 5 | 3 | 1 | 3 | |
| P09972 | ALDOC Fructosebisphosphate aldolase C | 16 | 4 | 3 | 1 | 4 | |
| Q9H857 | NT5DC2 5nucleotidase domaincontaining | 11 | 0 | 3 | 1 | 5 | |
| Q9H3G5 | CPVL Probable serine carboxypeptidase CPVL | 13 | — | 3 | 2 | 6 | |
| P06280 | GLA Alphagalactosidase A | 11 | 8 | 3 | 1 | 7 | |
| Q5T440 | IBA57 Putative transferase CAF17, | 14 | 8 | 3 | 1 | 8 | |
| P30837 | ALDH1B1 Aldehyde dehydrogenase X, | 6 | 4 | 3 | 1 | 9 | |
| P16278 | GLB1 Betagalactosidase | 12 | 6 | 3 | 1 | 10 | |
| P05091 | ALDH2 Aldehyde dehydrogenase, | 8 | 4 | 2 | 1 | 11 | |
| P30043 | BLVRB Flavin reductase (NADPH) | 20 | — | 2 | — | 12 | |
| Q9BTE7 | DCUN1D5 DCN1like protein 5 | 6 | — | 2 | 1 | 13 | |
| Q8IV08 | PLD3 Phospholipase D3 | 12 | 1 | 2 | 1 | 14 | |
| P49189 | ALDH9A1 4trimethylaminobutyraldehyde | 12 | 8 | 2 | 1 | 15 | |
| Q9HB40 | SCPEP1 Retinoidinducible serine | 5 | — | 2 | 0 | 16 | |
| P07339 | CTSD Cathepsin D | 13 | 10 | 1 | 0 | 17 | |
| Q13867 | BLMH Bleomycin hydrolase | 9 | 4 | 1 | 0 | 18 | |
| Q9H2U2 | PPA2 Inorganic pyrophosphatase 2, | 7 | 6 | 1 | 0 | 19 | |
| O14654 | IRS4 Insulin receptor substrate 4 | 20 | — | 1 | 0 | 20 | |
| Q9UBR2 | CTSZ Cathepsin Z | 13 | 9 | 3 | 2 | 21 | MDA- |
| P05121 | SERPINE1 Plasminogen activator inhibitor 1 | 17 | — | 3 | 0 | 22 | MB-231 |
| P07858 | CTSB Cathepsin B | 9 | 4 | 3 | 1 | 23 | |
| Q08380 | LGALS3BP Galectin3binding protein | 7 | — | 3 | — | 24 | |
| Q32P28 | LEPRE1 Prolyl 3hydroxylase 1 | 8 | 2 | 3 | 1 | 25 | |
| O14773 | TPP1 Tripeptidylpeptidase 1 | 15 | 7 | 3 | 1 | 26 | |
| O60568 | PLOD3 Procollagenlysine, 2oxoglutarate | 14 | 8 | 2 | 1 | 27 | |
| Q9P0L0 | VAPA Vesicleassociated membrane | 20 | — | 1 | — | 28 | |
| P07996 | THBS1 Thrombospondin1 | 16 | 6 | 1 | 0 | 29 | |
| Q9UNZ2 | NSFL1C NSFL1 cofactor p47 | 8 | — | 1 | 0 | 30 | |
| P38571 | LIPA Lysosomal acid lipase/cholesteryl ester | 7 | — | 4 | 1 | 31 | |
| P07602 | PSAP Proactivator polypeptide | 12 | 4 | 3 | 2 | 32 | |
| Q02809 | PLOD1 Procollagenlysine, 2oxoglutarate | 6 | — | 3 | 1 | 33 | |
| P15586 | GNS Nacetylglucosamine6sulfatase | 10 | 9 | 3 | 1 | 34 | |
| P10253 | GAA Lysosomal alphaglucosidase | 9 | — | 2 | 1 | 35 | |
| P13674 | P4HA1 Prolyl 4hydroxylase subunit alpha1 | 15 | 5 | 2 | 1 | 36 | |
| Q5JRX3 | PITRM1 Presequence protease mitochondrial | 12 | — | 2 | 0 | 37 | |

[§]bolded protein names are high-reactivity targets of probe 1.
*data represent mean ratio values ± standard deviation from n = 5 and n = 3 independent experiments for HEK293T and MDA-MB-231 cell lines, respectively.
[†]data represent mean ratio values ± standard deviation from n = 4 independent experiments for each cell line.
[‡]proteins found in the upper and lower right quadrants are separated by the double line.

TABLE 2

High-reactivity protein targets of probe 1

| Probe targets | Probe reactivity | Function | Electrophile |
|---|---|---|---|
| 1. S-adenosylmethionine (AdoMet) decarboxylase (AMD1/AdoMetDC) | 1, 2 | polyamine biosynthesis (cancer) | pyruvamide* |
| 2. Legumain (LGMN) | 1, 2 | cysteine protease (cancer) | aspartimide[†] |
| 3. α-mannosidase (MAN2B1) | 1, 2 | glycohydrolase (Mannosidosis) | unknown |
| 4. Secernin-3 (SCRN3) | 1, 2 | | |
| 5. Secernin-2 (SCRN2) | 1, 2 | N-terminal nucleophile (Ntn) hydrolase[‡] | unknown |
| 6. probable arginine tRNA ligase (RARS2) | 1 | protein synthesis (Pontocerebellar hypoplasia 6)[‡] | unknown |
| 7. Kelch-like ECH-associated protein-1 (KEAP1) | 1, 2 | antioxidant response regulator (cancer) | unknown |
| 8. β-amyloid-like precursor protein-2 (APLP2) | 1 | | |
| 9. β-amyloid precursor protein (APP) | 1 | Aβ precursor: amyloid plaques (Alzheimer's disease) | unknown |
| 10. ependymin-related protein-1 (EPDR1) | 1, 2 | neuron regeneration and memory[‡] | unknown |
| 11. Fat mass and obesity-associated Fe(II)- and 2-oxoglutarate (2OG)-dependent dioxygenase (FTO) | 2 | RNA demethylation [obesity and growth retardation, developmental delay, and facial dysmorphism (GDFD)] | unknown |

*enzyme cofactor formed in cells and targeted by nucleophiles[22]
[†]required for ligase activity in vitro[41]
[‡]predicted function Analogous experiments were also performed with the aryl hydrazine probe 2 (1 mM, 0.5 hour), which furnished a larger list of high-reactivity proteins (33 in total; Table 3) that contained several of the targets of probe 1 (compared in Table 4), as well as additional proteins that may reflect an expanded chemical reactivity for probe 2.

TABLE 3

Average SILAC ratios for probe 2-targeted proteins measured in the indicated cell line determined to be high-reactivity proteins as determined by a quadrant plot (FIG. 3E).

| Uniprot ID | description[§] | enrichment ratio$_{avg}$ | error* | competition ratio$_{avg}$ | error[†] | proteins[‡] | cell line |
|---|---|---|---|---|---|---|---|
| Q0VDG4 | SCRN3 Secernin-3 | 15 | 8 | 16 | 5 | 1 | HEK293T |
| Q9UPP1 | PHF8 Histone lysine demethylase PHF8 | 20 | — | 15 | 7 | 2 | |
| Q96FV2 | SCRN2 Secernin-2 | 20 | — | 13 | 3 | 3 | |
| O00767 | SCD AcylCoA desaturase | 20 | 0 | 9 | 4 | 4 | |
| Q13686 | ALKBH1 Alkylated DNA repair protein alkB | 20 | — | 8 | 7 | 5 | |
| O60568 | PLOD3 Procollagenlysine, 2oxoglutarate | 20 | 0 | 6 | 5 | 6 | |
| P05091 | ALDH2 Aldehyde dehydrogenase mitochondrial | 11 | 4 | 6 | 2 | 7 | |
| P17707 | AMD1 S-adenosylmethionine decarboxylase | 20 | 0 | 6 | 1 | 8 | |
| Q16850 | CYP51A1 Lanosterol 14alpha demethylase | 14 | — | 6 | 5 | 9 | |
| P30519 | HMOX2 Heme oxygenase 2 | 20 | 0 | 5 | 1 | 10 | |
| Q9C0B1 | FTO Alphaketoglutaratedependent dioxygenase | 13 | 4 | 5 | 0 | 11 | |
| P04075 | ALDOA Fructosebisphosphate aldolase A | 12 | 2 | 5 | 1 | 12 | |
| P09972 | ALDOC Fructosebisphosphate aldolase C | 14 | 3 | 5 | 1 | 13 | |
| P30837 | ALDH1B1 Aldehyde dehydrogenase X | 11 | 7 | 5 | 2 | 14 | |
| O60427 | FADS1 Fatty acid desaturase 1 | 20 | 0 | 4 | 1 | 15 | |
| Q8N2H3 | PYROXD2 Pyridine nucleotidedisulfide | 20 | 0 | 20 | — | 16 | MDA-MB-231 |
| O75976 | CPD Carboxypeptidase D | 20 | 0 | 15 | 7 | 17 | |
| Q9UM22 | EPDR1 Mammalian ependyminrelated | 20 | 0 | 5 | 2 | 18 | |
| P02794 | FTH1 Ferritin heavy chain | 20 | 0 | 5 | 0 | 19 | |
| Q92626 | PXDN Peroxidasin homolog | 20 | 0 | 5 | 1 | 20 | |
| P50897 | PPT1 Palmitoylprotein thioesterase 1 | 20 | 0 | 5 | 2 | 21 | |
| P07858 | CTSB Cathepsin B | 14 | 2 | 5 | 1 | 22 | |
| Q9UBR2 | CTSZ Cathepsin Z | 19 | 1 | 5 | 2 | 23 | |
| P10619 | CTSA Lysosomal protective protein | 9 | — | 4 | — | 24 | |
| P53634 | CTSC Dipeptidyl peptidase 1 | 20 | 0 | 9 | — | 25 | |
| H7C469 | Uncharacterized protein | 14 | 0 | 5 | — | 26 | |
| Q5SRE7 | PHYHD1 PhytanoylCoA dioxygenase | 14 | 2 | 5 | 1 | 27 | |
| P07602 | PSAP Proactivator polypeptide | 5 | 0 | 5 | 0 | 28 | |
| O43583 | DENR Densityregulated protein | 20 | — | 5 | — | 29 | |
| P07339 | CTSD Cathepsin D | 16 | 3 | 4 | 1 | 30 | |
| O00754 | MAN2B1 Lysosomal alphamannosidase | 20 | 0 | 4 | 2 | 31 | |
| O14773 | TPP1 Tripeptidylpeptidase 1 | 18 | 2 | 4 | — | 32 | |
| Q9HB40 | SCPEP1 Retinoidinducible serine | 19 | 2 | 4 | 1 | 33 | |
| Q9NQH7 | XPNPEP3 Probable XaaPro aminopeptidase 3 | 20 | 0 | 4 | 1 | 1 | HEK293T |
| Q5T440 | IBA57 Putative transferase CAF17 | 9 | 7 | 4 | 1 | 2 | |

TABLE 3-continued

Average SILAC ratios for probe 2-targeted proteins measured in the indicated cell line determined to be high-reactivity proteins as determined by a quadrant plot (FIG. 3E).

| | | enrichment | | competition | | | |
|---|---|---|---|---|---|---|---|
| Uniprot ID | description[§] | ratio$_{avg}$ | error[*] | ratio$_{avg}$ | error[†] | proteins[‡] | cell line |
| O95864 | FADS2 Fatty acid desaturase 2 | 20 | 0 | 4 | 0 | 3 | |
| Q9H857 | NT5DC2 5nucleotidase domaincontaining | 16 | 3 | 4 | 1 | 4 | |
| Q7L8L6 | FASTKD5 FAST kinase domaincontaining | 10 | 3 | 3 | 1 | 5 | |
| O60341 | KDM1A Lysinespecific histone demethylase 1A | 20 | 0 | 2 | 0 | 6 | |
| Q15067 | ACOX1 Peroxisomal acylcoenzyme A oxidase 1 | 19 | 1 | 2 | 0 | 7 | |
| P41229 | KDM5C Lysinespecific demethylase 5C | 19 | 3 | 3 | 0 | 8 | |
| Q96DG6 | CMBL Carboxymethylenebutenolidase homolog | 18 | 4 | 3 | 1 | 9 | |
| Q8NB78 | KDM1B Lysinespecific histone demethylase 1B | 17 | 5 | 2 | 1 | 10 | |
| Q5R3I4 | TTC38 Tetratricopeptide repeat protein 38 | 14 | 7 | 2 | 1 | 11 | |
| P31350 | RRM2 Ribonucleosidediphosphate reductase | 13 | — | 1 | 0 | 12 | |
| Q8IUF8 | MINA MYCinduced nuclear antigen | 8 | — | 2 | — | 13 | |
| P99999 | CYCS Cytochrome c | 7 | 3 | 0 | 0 | 14 | |
| Q8IV08 | PLD3 Phospholipase D3 | 5 | — | 2 | 0 | 15 | |
| P10253 | GAA Lysosomal alphaglucosidase | 20 | 0 | 4 | 2 | 16 | MDA- |
| Q9NZ08 | ERAP1 Endoplasmic reticulum aminopeptidase | 8 | 3 | 4 | 0 | 17 | MB-231 |
| Q13510 | ASAH1 Acid ceramidase | 20 | 0 | 4 | 0 | 18 | |
| P42785 | PRCP Lysosomal ProX carboxypeptidase | 15 | 4 | 4 | 1 | 19 | |
| P25774 | CTSS Cathepsin S | 18 | 4 | 3 | — | 20 | |
| Q02318 | CYP27A1 Sterol 26hydroxylase, mitochondrial | 20 | 0 | 3 | 1 | 21 | |
| P02792 | FTL Ferritin light chain | 7 | — | 3 | 0 | 22 | |
| P38571 | LIPA Lysosomal acid lipase/cholesteryl ester | 17 | — | 3 | — | 23 | |
| P05121 | SERPINE1 Plasminogen activator inhibitor 1 | 20 | — | 3 | 0 | 24 | |
| P04040 | CAT Catalase | 20 | — | 1 | 0 | 25 | |
| P17050 | NAGA AlphaNacetylgalactosaminidase | 17 | 5 | 3 | 1 | 26 | |
| O15382 | aminotransferase, mitoch | 15 | 7 | 2 | 1 | 27 | |
| Q14145 | KEAP1 Kelchlike ECHassociated protein 1 | 12 | 1 | 3 | 1 | 28 | |
| P07686 | HEXB Betahexosaminidase subunit beta | 11 | 1 | 3 | 1 | 29 | |
| P50281 | MMP14 Matrix metalloproteinase14 | 10 | — | 3 | 0 | 30 | |
| Q8NHP8 | PLBD2 Putative phospholipase Blike 2 | 9 | — | 3 | 1 | 31 | |
| Q32P28 | LEPRE1 Prolyl 3hydroxylase 1 | 8 | 2 | 2 | 1 | 32 | |
| Q08380 | LGALS3BP Galectin3binding protein | 7 | — | 3 | 1 | 33 | |
| Q99519 | NEU1 Sialidase1 | 5 | — | 3 | — | 34 | |
| P61106 | RAB14 Rasrelated protein Rab14 | 5 | — | 3 | — | 35 | |
| Q99538 | LGMN Legumain | 20 | 0 | 4 | 1 | 36 | |
| Q13228 | SELENBP1 Seleniumbinding protein 1 | 20 | 0 | 3 | 3 | 37 | |
| Q02809 | PLOD1 Procollagenlysine, 2oxoglutarate | 8 | 0 | 3 | 1 | 38 | |
| O15460 | P4HA2 Prolyl 4hydroxylase subunit alpha2 | 20 | — | 3 | 0 | 39 | |
| P13674 | P4HA1 Prolyl 4hydroxylase subunit alpha1 | 8 | 1 | 3 | 1 | 40 | |
| P54687 | BCAT1 Branchedchainaminoacid | 20 | 0 | 2 | 1 | 41 | |
| O15254 | ACOX3 Peroxisomal acylcoenzyme A oxidase 3 | 20 | 0 | 1 | 0 | 42 | |
| Q8N8N7 | PTGR2 Prostaglandin reductase 2 | 15 | — | 1 | 1 | 43 | |
| Q7LG56 | RRM2B Ribonucleosidediphosphate reductase | 7 | — | 2 | — | 44 | |
| P15586 | GNS Nacetylglucosamine6sulfatase | 7 | 2 | 3 | 1 | 45 | |
| P16278 | GLB1 Betagalactosidase | 6 | 2 | 2 | 0 | 46 | |
| P09110 | ACAA1 3ketoacylCoA thiolase, peroxisomal | 6 | 1 | 2 | 0 | 47 | |
| O00469 | PLOD2 Procollagenlysine, 2oxoglutarate | 6 | 4 | 2 | 1 | 48 | |

[§]bolded protein names are high-reactivity targets of probe 1.
[*]data represent mean ratio values ± standard deviation from n = 4 and n = 3 independent experiments for HEK293T and MDA-MB-231 cell lines, respectively.
[†]data represent mean ratio values ± standard deviation from n = 4 and n = 3 independent experiments for HEK293T and MDA-MB-231 cell lines, respectively.
[‡]proteins found in the upper and lower right quadrants are separated by the double line.

TABLE 4

Ratio comparison of probe 1- versus probe 2-targeted proteins from Tables 2 and 3.

| Uniprot ID | description[§] | ratio$_{avg}$: probe 1 | | ratio$_{avg}$: probe 2 | |
|---|---|---|---|---|---|
| | | enrichment | competition | enrichment | competition |
| Q99538 | LGMN Legumain | 20 | 18 | 20 | 4 |
| Q96FV2 | SCRN2 Secernin2 | 20 | 9 | 20 | 13 |
| Q0VDG4 | SCRN3 Secernin3 | 20 | 6 | 15 | 16 |
| P17707 | AMD1 Sadenosylmethionine decarboxylase | 20 | 5 | 20 | 6 |
| Q9UM22 | EPDR1 Mammalian ependyminrelated | 20 | 20 | 20 | 5 |
| O00754 | MAN2B1 Lysosomal alphamannosidase | 20 | 8 | 20 | 4 |
| Q14145 | KEAP1 Kelchlike ECHassociated protein 1 | 17 | 20 | 12 | 3 |
| Q5T160 | RARS2 Probable argininetRNA ligase, | 16 | 4 | — | 3 |

TABLE 4-continued

Ratio comparison of probe 1- versus probe 2-targeted proteins from Tables 2 and 3.

| Uniprot ID | description§ | ratio_avg: probe 1 enrichment | ratio_avg: probe 1 competition | ratio_avg: probe 2 enrichment | ratio_avg: probe 2 competition |
|---|---|---|---|---|---|
| Q06481 | APLP2 Amyloidlike protein 2 | 19 | 7 | 20 | — |
| P05067 | APP Amyloid beta A4 protein | 16 | 4 | — | — |
| P05091 | ALDH2 Aldehyde dehydrogenase, mitochondrial | 8 | 2 | 11 | 6 |
| Q9HB40 | SCPEP1 Retinoidinducible serine | 5 | 2 | 19 | 4 |
| Q9UPP1 | PHF8 Histone lysine demethylase PHF8 | — | — | 20 | 15 |
| O00767 | SCD AcylCoA desaturase | — | — | 20 | 9 |
| Q13686 | ALKBH1 Alkylated DNA repair protein alkB | — | — | 20 | 8 |
| O60568 | PLOD3 Procollagenlysine, 2oxoglutarate | 14 | 2 | 20 | 6 |
| Q16850 | CYP51A1 Lanosterol 14alpha demethylase | — | — | 14 | 6 |
| P30519 | HMOX2 Heme oxygenase 2 | — | — | 20 | 5 |
| Q9C0B1 | FTO Alphaketoglutaratedependent dioxygenase | — | 1 | 13 | 5 |
| P04075 | ALDOA Fructosebisphosphate aldolase A | 16 | 3 | 12 | 5 |
| P09972 | ALDOC Fructosebisphosphate aldolase C | 16 | 3 | 14 | 5 |
| P30837 | ALDH1B1 Aldehyde dehydrogenase X, | 6 | 3 | 11 | 5 |
| O60427 | FADS1 Fatty acid desaturase 1 | — | — | 20 | 4 |
| Q8N2H3 | PYROXD2 Pyridine nucleotidedisulfide | — | — | 20 | 20 |
| O75976 | CPD Carboxypeptidase D | — | — | 20 | 15 |
| P53634 | CTSC Dipeptidyl peptidase 1 | — | 3 | 20 | 9 |
| H7C469 | Uncharacterized protein | — | 2 | 14 | 5 |
| P02794 | FTH1 Ferritin heavy chain | 1 | 1 | 20 | 5 |
| Q92626 | PXDN Peroxidasin homolog | — | — | 20 | 5 |
| P50897 | PPT1 Palmitoylprotein thioesterase 1 | — | 5 | 20 | 5 |
| P07858 | CTSB Cathepsin B | 9 | 3 | 14 | 5 |
| Q5SRE7 | PHYHD1 PhytanoylCoA dioxygenase domain | — | — | 14 | 5 |
| P07602 | PSAP Proactivator polypeptide | 12 | 3 | 5 | 5 |
| O43583 | DENR Densityregulated protein | — | 1 | 20 | 5 |
| Q9UBR2 | CTSZ Cathepsin Z | 13 | 3 | 19 | 5 |
| P07339 | CTSD Cathepsin D | 13 | 1 | 16 | 4 |
| P10619 | CTSA Lysosomal protective protein | 4 | 4 | 9 | 4 |
| O14773 | TPP1 Tripeptidylpeptidase 1 | 15 | 3 | 18 | 4 |

§bolded protein names are high-reactivity targets of probe 1 and bolded ratio numbers highlight high-reactivity with the indicated probe.

Unable to predict the chemical properties of all potential probe adducts, there exists the possibility that targets may be lost due to potentially unstable hydrazone adducts that could be generated via capture of certain carbonyl electrophiles. To test this, an enrichment profiling experiment was performed with probe 1 in the presence of 50 mM NaCNBH$_3$ added during cell lysis. No change or increase in probe 1-enriched proteins was observed under these conditions, suggesting that targets reacting with probe 1 via hydrazone formation were stable to streptavidin enrichment and proteomic analysis.

A representative subset of high-reactivity targets by recombinant expression was validated. In particular, four proteins were selected, of which three (AMD1, SCRN3 and KEAP1) reacted with both probes 1 and 2 and one (FTO) was preferentially targeted by probe 2. The recombinant expression of each protein in transfected HEK293T cells was confirmed by western blotting (FIG. 3D (upper blots)). In each case, treatment of transfected cells with probe 1 or 2, followed by conjugation to azide-rhodamine, produced a strong fluorescent band at the appropriate molecular weight that was absent in mock-transfected control cells (FIG. 3D (lower gels)). Probe labeling of each protein was blocked by treatment with excess non-clickable probes 3 or 4 (FIG. 3D (lower gels)). For FTO, selective reactivity with the aryl probe 2 over the alkyl probe 1 (FIG. 3D) was observed, matching the proteomic data obtained for endogenously expressed FTO in cells (Table 3). These data indicate that hydrazine reactivity is an intrinsic property of the protein targets of probes 1 and 2 that is shared by both the endogenous and recombinant forms of these proteins.

Example 3: Profiling of Pyruvoyl Modification State of AMD1 in Cells

Some of the probe targets identified as described above in Example 3 are known to possess electrophilic PTMs (Table 1). Prominent among these was S-adenosyl-L-methionine (SAM) decarboxylase (AMD1 or AdoMetDC), which employs an N-terminally bound pyruvoyl group generated from serine to catalyze the rate-limiting step in polyamine biosynthesis[28] AMD1 can be inhibited by hydrazines and related nucleophiles that target the enzyme's pyruvoyl cofactor[22,29], which is installed by a putrescine-induced auto-cleavage of the inactive proenzyme (38 kDa) to generate a processed, catalytically competent enzyme (30 kDa) (FIG. 4A). This electrophilic cofactor in AMD1 was monitored in cells.

Purification and Reconstitution of Active AMD1 from *E. coli*

Full-length AMD1 having an additional 12 amino acids (MRGSH6GS) (SEQ ID NO: 46) appended to the N-terminal methionine residue was expressed from the bacterial vector pQE30. The appendage contains a His6 element (SEQ ID NO: 69) to permit purification of the protein by metal ion affinity chromatography on Ni-NTA agarose (Qiagen). *E. coli* cell cultures were grown at 37° C. in rich LB broth (35 g/L tryptone, 20 g/L yeast extract, 5 g/L NaCl, and 0.05 g/L kanamycin (pH 7.0)) to an optical density at 600 nm of 0.6-0.8. The flasks were cooled rapidly by incubation on ice for 30 minutes prior to addition of IPTG (1 mM). Following induction, cultures were grown at 15-18° C. for an additional 16-20 hours and cells were harvested by centrifugation (8,000 g, 30 min, 4° C.). The cell paste was flash-frozen in liquid N$_2$ and stored at −80° C. A typical yield was 8-10 g of wet cell paste per liter of culture. The frozen paste was resuspended (5 mL/g) in 50 mM Na-HEPES buffer (pH 7.5) containing 300 mM NaCl, 5 mM imidazole, 0.1 mg/mL Dnase I, 1 mM $CaCl_2$, 1 mM $MgCl_2$, 2.5 mM putrescine (purchased from Acros) and 0.1 mM phenylmethanesulfonyl fluoride.

Putrescine, the simplest polyamine in the biosynthetic pathway, stimulates autocleavage of the inactive proenzyme of AMD1 into its α and β subunits[73]. Because both subunits remain tightly associated and are essential for activity, the full-length protein can be proteolytically processed prior to purification. In this case, the pyruvoyl-containing α subunit co-purifies with the smaller N-terminal (His)$_6$-tagged β subunit. The cells were lysed at 4° C. by a single passage through a microfluidizer at 16,000 psi and the cell debris was pelleted by centrifugation (10,000 g, 20 min, 4° C.). The supernatant was slowly stirred with Ni-NTA resin (0.5 mL column volume (CV)/g cells) for 30 minutes at 4° C. The slurry was loaded into a column and washed with 50 mM Na-HEPES buffer (pH 7.5) containing 300 mM NaCl and 5 mM imidazole until the A280 and A260 were both ~0 (~10 CVs). Protein was eluted from the resin with 50 mM Na-HEPES buffer (pH 7.5) containing 100 mM NaCl and 250 mM imidazole. Protein fractions were pooled and dialyzed against 20 mM Na-HEPES buffer (pH 7.5) containing 2.5 mM DTT and 2.5 mM putrescine to ensure activation was complete. Following dialysis, the protein was concentrated to ~25 mg/mL prior to being flash-frozen and stored at −80° C. The yield was ~5 mg protein (>90% purity) per g of cell paste. Protein concentrations were determined on a Nanodrop spectrophotometer by assuming a molar absorptivity ($\varepsilon_{280}$) of 41,370 $M^{-1}$ $cm^{-1}$ as calculated by the method of Gill and von Hippel[74]. The conversion of the proenzyme to the active pyruvoyl enzyme was accessed by denaturing SDS-PAGE and Coomassie staining.

Probe 1-Labelling of the Pyruvoyl Cofactor in AMD1

A 100 μL solution of 50 μM purified reconstituted AMD1 in PBS was incubated overnight at ambient temperature in the presence or absence of 3 mM probe 1 (pH 7). A 25 μL aliquot of the reaction was precipitated with acetonitrile (100 μL) to remove excess probe and the protein pellet was resuspended into 50 μL PBS with mild sonication. Half of that material (20 g) was diluted with 6 M urea in PBS. Disulfides were reduced with TCEP (5 mM) pre-neutralized with potassium carbonate (15 mM) for 15 min at 37° C. Reduced thiols were alkylated by iodoacetamide (10 mM) for 30 min at ambient temperature protected from light. The solution was diluted to 2 M urea with PBS (~350 μL total volume) and digested for three hours at 37° C. with sequencing grade porcine trypsin (2 μg) (Promega) in the presence of $CaCl_2$ (1 mM). Digested peptides from ~3 μg protein (50 μL aliquot of the digest) were diluted with fresh ammonium bicarbonate (25 mM) and 0.1% formic acid maintaining neutral pH. The sample was pressure loaded directly onto a 100 μm fused silica capillary column with a 5 μm tip containing 10 cm C18 resin. Peptides were eluted from the column using a 180 minute gradient from 0% to 50% Buffer B (Buffer A: 5% acetonitrile, 95% $H_2O$, 0.1% formic acid; Buffer B: 80% acetonitrile, 20% $H_2O$, 0.1% formic acid) and analyzed on an LTQ-Orbitrap Finnigan mass spectrometer (Thermo Scientific). For these experiments peptides in the +1 charge state were not excluded for fragmentation.

Characterization of the AMD1 N-Terminus and Reaction with Probe 1

AMD1 peptides were identified as described above in Example 3 except that the heavy search was excluded. The pyruvoyl N-terminal peptide before and after labelling could be identified using variable modifications of 70.0055 and 122.0480 Da, respectively, on serine. In addition, these spectra assignments were confirmed manually by extracting parent ion chromatograms ($m/z_{theor}$=768.3597 and 820.4022, respectively, ±10 ppm) from the .raw file, validating that the corresponding isotopic envelopes reflect a peptide in the +1 charge state and assigning the fragment ions in the corresponding MS2 spectra. Parent ion chromatograms from unmodified peptides identified in the standard search were extracted from the .raw file as well to compare the relative peak intensities of internal AMD1 peptides between the two samples (absence or presence of probe 1). The pyruvoyl terminal peptide was undetectable in the presence of probe, suggesting that the reaction with probe 1 was complete. The remaining peptides showed no significant change in their parent ion intensities demonstrating selectivity against unmodified residues even at extended incubation times with 100-fold excess probe over protein.

Dynamic Regulation of Cofactor Status in AMD1

To enhance expression and labelling of endogenous AMD1, HEK293T cells were treated with difluoromethylornithine (DFMO; purchased from Santa Cruz Biotechnology) (5 mM) for 48 h in RPMI 1640 media (Fisher Scientific, A14517-01) containing 10 μM L-methionine. Cells were washed and treated with probe 1 in the absence of methionine. To demonstrate that methionine regulates the cofactor status of AMD1, the C-terminally-tagged proenzyme was transfected in HEK293T cells in RPMI media containing 10 μM versus 200 μM L-methionine. Probe 1-labelling, proteome preparation, fluorophore conjugation, gel-based analysis and western blotting were performed as described above in Examples 2 and 3. Band intensities were quantified using ImageJ software[75]. To determine the ratio of active to inactive forms of the cofactor under each condition, AMD1 was first purified from these proteomes via its C-terminal FLAG affinity tag. Briefly, about 0.5 mg soluble proteomes isolated from probe 1-labelled AMD1-transfected cells grown in low versus high methionine were each diluted to 1 mL with 50 mM Na-HEPES buffer (pH 7.5) supplemented with 500 mM NaCl and 1% Triton X-100. Each proteome was incubated overnight at 4° C. by rotation with a pre-equilibrated slurry (25 μL resin (CV), anti-FLAG M2 affinity gel, Sigma). The resin was washed by resuspension and centrifugation with the same buffer supplemented with 500 mM NaCl (5×1 mL) followed by 100 mM NaCl (2×1 mL). The bound AMD1 protein was eluted in 100 μL of low salt buffer containing 150 ng/L $(FLAG)_3$ peptide [DYKDHD-(G)-DYKDHD-(I)-DYKD4K] (SEQ ID NO: 47). To prevent contamination from the excess $(FLAG)_3$ peptide in the elution, the protein was purified by gel. The gel was stained with a Coomassie dye that is MS-compatible (InstantBlue, Expedeon or ProtoBlue, National Diagnostics) and then rinsed thoroughly. The ~30 kDa band corresponding to AMD1 was manually excised, washed with 100 mM ammonium bicarbonate (2×0.5 mL), and dehydrated with acetonitrile until the gel pieces were completely opaque. Cysteines were reduced by rehydration in TCEP (10 mM in 100 mM ammonium bicarbonate) for 30 minutes at 37° C. The gel band was again dehydrated with acetonitrile. Cysteines were alkylated by rehydration with iodoacetamide (55 mM in 100 mM ammonium bicarbonate) for 30 min at ambient temperature protected from light. Gel bands were dehydrated once more. The gel-bound protein was digested by rehydration with 0.4 μg trypsin (reconstituted in PBS) and further diluted to ~200 μL with 25 mM triethylammonium bicarbonate (TEAB). The samples were then incubated at 37° C. overnight.

Late-stage reductive dimethylation[76] with formaldehyde isotopologues was used to differentiate methionine growth conditions. Briefly, $^{13}C$- and $^{2}H$-enriched 'heavy' formaldehyde ($^{13}C^{2}H_2O$, 0.15% (w/v)) was added to proteolyzed AMD1 isolated from high methionine conditions whereas natural abundance formaldehyde (light) was added to that from low methionine conditions at the same concentration. N-termini and lysine residues of digested peptides were sufficiently dimethylated in the presence of sodium cyanoborohydride ($NaBH_3CN$; 22 mM) after 1 hour incubation at ambient temperature. The reactions were quenched by addition of ammonium hydroxide (0.23%) and formic acid (0.5%). The heavy- and light-derivatized samples were then combined and analyzed by LC-MS/MS using the same method for proteomic profiling experiments described in Example 3 with the exception that peptides in the +1 charge state were fragmented. Parent masses for three dimethylated isotopic peptide pairs were manually extracted (±10 ppm) from Xcalibur .raw files: (i) the probe 1-labelled pyruvoyl N-terminus, (ii) the inactive alanine N-terminus and (iii) an internal peptide that was used to compare total protein expression. Lysine residues and peptide N-termini are mass-shifted by 28.0313 and 34.06312 Da for light and heavy isotopologues, respectively. Peptide identification was confirmed manually by assignment of b- and y-ions. The peaks in the parent ion chromatograms for each of these three peptide pairs were integrated in Xcalibur. The ratio of the peak areas for each light:heavy peptide pair is reported in FIGS. 4G and 4H and Table 5. No normalization of the ratios was required to adjust for different expression levels; the ratio for the internal AMD1 peptide was 1.02, consistent with the unchanged expression profile by gel (FIG. 4F) that was maintained throughout sample preparation.

N-terminal pyruvoyl tryptic peptide in 1-treated AMD1 samples was observed (FIG. 5B), indicating that the reaction between probe 1 and the pyruvoyl group of AMD1 proceeded to near-completion. We did not observe evidence of modification of any other tryptic peptides from AMD1 (FIGS. 5C and 5D), supporting that probe 1 reacted specifically with the N-terminal pyruvoyl group.

Difluoromethylornithine (DFMO), an inhibitor of putrescine biosynthesis, has been shown to increase the expression of AMD1[30]. It was confirmed that probe 1 could detect DMFO-induced changes in the endogenous concentration of active AMD1 in cells (FIG. 4E). Lowering the concentration of L-methionine, a biosynthetic precursor for SAM, from that found in standard culture media (200 μM) to physiological serum (10 μM)[31], was also found to increase probe 1 labeling of recombinant AMD1 in cells by-seven-fold with negligible changes in AMD1 expression (FIG. 4F).

A mechanism to explain the regulation of AMD1 activity by SAM concentration has been described for the purified enzyme in vitro[32], where each catalytic event is partitioned such that a small fraction of the pyruvoyl cofactor is inactivated irreversibly to alanine (Ala) instead of being regenerated (FIG. 4A). Consistent with this model being operational in cells, the differences observed in probe 1-labeling of AMD1 in low versus high methionine could reflect changes in the N-terminal structure of AMD1. To test this, AMD1-transfected HEK293T cells were cultured in high versus low methionine, cells were treated with probe 1, and then AMD1 protein was enriched from each cell preparation with anti-FLAG antibodies. The AMD1 protein samples were further purified by SDS-PAGE, digested in gel with trypsin, and the resulting peptides modified with isotopically heavy or light formaldehyde. Combining heavy and light

TABLE 5[1]

Raw data used to calculate AMD1 peptide ratios shown in FIGS. 4G-4H.

| AMD1 peptide | L/H ratio | peak area (x 10$^7$) light | peak area (x 10$^7$) heavy | [M + H]$^+_{measured}$ light | [M + H]$^+_{measured}$ heavy | [M + H]$^+_{theoretical}$ light | [M + H]$^+_{theoretical}$ heavy | mass error (ppm) light | mass error (ppm) heavy |
|---|---|---|---|---|---|---|---|---|---|
| probe 1-modified pyruvoyl (S*MFVSK) | 6:1 | 17 | 3 | 848.4343 | 854.4656 | 848.4335 | 854.4653 | 0.9 | 0.4 |
| ASMFVSK | 1:23 | 80 | 1,850 | 825.4543 | 837.5168 | 825.4539 | 837.5175 | 0.5 | -0.8 |
| FVTTLFVNQSSK | 1:1 | 4,500 | 4,400 | 1,426.7954 | 1,438.8564 | 1,426.7914 | 1,438.8614 | 2.8 | -3.5 |

[1]probe 1-modified pyruvoyl S*MFVSK (SEQ ID NO: 1), ASMFVSK AMD1 peptide (SEQ ID NO: 2), FVTTLFVNQSSK AMD1 peptide (SEQ ID NO: 3)

Results

Blotting with an anti-FLAG antibody detected both the full-length pro- and processed active forms of AMD1 when expressed as a C-terminal FLAG-tagged protein in transfected HEK293T cells, whereas only the larger pro-form was detected for an AMD1 protein bearing the FLAG tag on its N-terminus (FIG. 4B), consistent with the expected processing event that cleaves an N-terminal portion of AMD1. Importantly, for either N- or C-terminally tagged AMD1, strong labeling with probe 1 was observed exclusively for the processed form of these proteins (FIG. 4B). Active human AMD1 expressed and purified from E. coli was treated with probe 1, followed by tryptic digestion of the protein and LC-MS/MS analysis, which identified the N-terminal pyruvoyl modification as the site of probe-1 reactivity (FIGS. 4C and 4D; FIG. 5A). Loss of the unmodified samples (corresponding to cells grown in high and low methionine), followed by LC-MS/MS analysis, revealed much greater signals for the probe 1-labelled pyruvoyl N-terminal tryptic peptide of AMD1 in low methionine-treated cells (A) (FIGS. 4G and 4H). Conversely, the alanine form of the N-terminal tryptic peptide of AMD1 was dramatically increased in the high methionine-exposed cells (B) (FIGS. 4G and 4H). An internal tryptic peptide from AMD1 was also measured, which revealed no changes in protein expression caused by low versus high methionine exposure (C) (FIGS. 4G and 4H).

These data, taken together, indicate that changes in methionine content significantly alter the fraction of active, N-terminal pyruvoyl-modified AMD1 in cells, such that persistent metabolic flux under high methionine conditions leads to progressive loss of the cofactor and catalytic activity. That probe 1 monitors the post-translational regulation of AMD1 in cells indicates hydrazines can serve not only as inhibitors[22], but also activity-based probes for this enzyme. These data also confirm that hydrazine probes react with electrophilic cofactors of established functionality in enzymes.

Figure 21B:
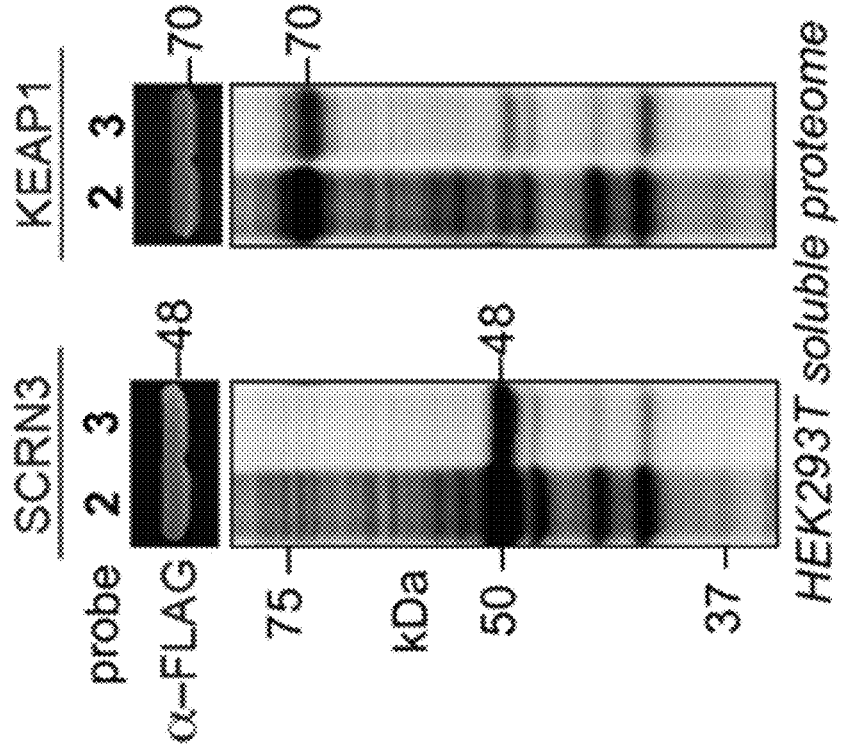
FIGS. 21A-21B show protein labelling in cells with oxyamine probes, as described in Example 3.
Figure 21A:
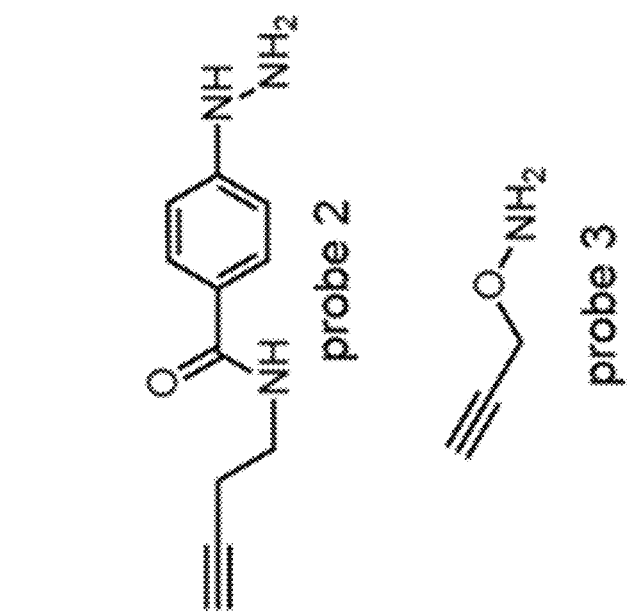

Similar labelling experiments were performed with an oxyamine probe 3 (FIG. 21A). Oxyamine probe 3 is commercially available, but to the best of the knowledge of the inventors, has not been used to label proteins in living cells. The results demonstrate that oxyamine probes can also be used to label proteins having electrophilic PTMs in living cells according to the methods of the invention (FIG. 21B).

Example 4: Identification and Characterization of Novel Electrophilic PTM (an N-Terminal Glyoxylyl Modification) of SCRN3

The peptide, rather than the whole protein, harboring the probe-reactive electrophile was identified to whether additional targets of probes 1 and 2, as listed in Tables 1-3, might possess as-of-yet structurally uncharacterized electrophilic modifications. This site-specific profiling method, termed isoTOP-ABPP[33], leverages isotopically differentiated, protease-cleavable biotin-azide tags to enrich and release probe-labelled peptides as mass-differentiated pairs (FIG. 6A). While this approach has been used successfully to identify the sites of reactivity for several probes[34], in these past instances, the sites all represented natural amino acids. Here, an additional challenge was that the sites of probe 1/2 reactivity were expected to be non-natural (e.g., PTM-modified amino acids) and, in most cases, not predictable from the sequences of protein targets. Unmodified peptide standards of SCRN3 [Cys6-Arg20 (CDTFVALPPATVDNR) (SEQ ID NO: 25) and Ala126-Lys136 (ALNVIVDLLEK) (SEQ ID NO: 34)] were purchased from Biopeptide Co.

IsoTOP-ABPP Sample Preparation to Isolate Probe-Captured Peptides

To demonstrate that the peptide containing the probe-labelled pyruvoyl group in AMD1 could be isolated from other unmodified peptides of the protein, the previously described isoTOP-ABPP protocol was adapted[69,74]. Soluble proteomes (2 mgs total protein) from wild-type or AMD1-transfected HEK293T cells treated in situ with probe 1 or 2 were prepared as described above and diluted to 1 mL with PBS. Half of the proteome (0.5 mL) was conjugated to the light TEV tag and the other half to the heavy TEV tag (structures shown in Example 5). Click reactions were scaled accordingly to maintain final concentrations of 0.1 mM TBTA, 1 mM $CuSO_4$, 100 μM of light or heavy biotin-TEV-azide (5 mM in DMSO) and 1 mM TCEP. The mixture was vortexed and placed on a rotator at ambient temperature. After 1 hour the samples were centrifuged (16,000 g, 5 min, 4° C.), resulting pellets were mildly sonicated in ice-cold methanol (0.5 mL), the light- and heavy-labelled proteomes were combined, centrifuged once more, solubilized with 1.2% SDS (1 mL in PBS), and stored at −80° C. overnight.

The next day samples were diluted to ~0.2% SDS with PBS (~5 mL) and incubated with pre-equilibrated streptavidin agarose resin (100 μL 1:1 slurry) for ~2-3 hours at ambient temperature. The resin was washed as described above for profiling experiments, transferred to clean microcentrifuge tubes, and resuspended in urea (500 μL, 6 M in PBS). Cysteines were reduced and alkylated with TCEP and iodoacetamide, respectively as described above. The resin was washed once with PBS to remove the reagents and bound proteins were digested with trypsin (2 μg) for 8-12 hours at 37° C. in the presence of 2 M urea (200 μL, in PBS) and $CaCl_2$ (1 mM).

Unmodified peptides, urea, and trypsin were removed by sequential washes with PBS (5×0.5 mL) and $H_2O$ (5×0.5 mL). The resin was transferred to clean microcentrifuge tubes and equilibrated with TEV buffer (50 mM Tris, pH 8). Remaining immobilized peptides were released with TEV protease (~1-2 μM in ~200 μL TEV buffer at 30° C. for 3-5 h). Heavy- and light-labelled peptides were collected and recovered from the resin with $H_2O$ (2×50 μL). Samples were stored at −80° C. and analyzed within several days.

The resultant probe-labelled peptides are recognized as co-eluting isotopic pairs in a 1:1 ratio that are resolved by 6.0138 Da due to incorporation of natural abundance (light) or L-[$^{13}C_5$,$^{15}N$]valine (heavy) into the portion of the tag that is retained. Data was collected as described above except for the salt 'bumps' applied in the chromatographic gradients (0%, 30%, 60%, 90% and 100% $NH_4OAc$). All five steps were required when avidin resin was used, as a much higher background of unpaired peptides was observed. By contrast, with streptavidin resin, this method could be condensed to a three-step salt gradient (0%, 30%, and 100%) or a one-dimensional separation as described for purified AMD1.

Characterization of the Pyruvoyl Cofactor in AMD1 by isoTOP-ABPP

The isoTOP-ABPP method has generally been used for detection of a large number of peptides that are uniformly modified with cysteine-selective[69] or photoaffinity-based[68] probes. Single- or variable-residue targeting by a conserved mechanism translates to a universal mass shift that is applied to a selective site(s) in each peptide that, in most cases, is positioned internally as a result of trypsin specificity. Identification of the consequent tagged peptides is compatible with the ProLuCID[78] algorithm and search features of the IP2 software. However, the hydrazone product of the probe-labelled pyruvoyl N-terminus of AMD1 escaped detection by this search method.

Although the unmodified y-ions initiated from the C-terminus of the small 6-mer half-tryptic peptide were easily detectable, the b-ion fragmentation occurred primarily within the peptide-based tags that effectively extended the N-terminus (FIGS. 7A-7E). Because the standard search algorithm is not equipped to predict or specify fragmentation occurring in the mass shift parameter itself, and, because these peaks were the most abundant in the spectra, a peptide spectrum match could not be found in the database. Instead, the spectra was assigned manually. To be certain of the peak assignments and charge state of the tag-specific b-ions, the instrument method was modified such that both the parent and fragment ions were measured in the orbitrap to gain high-resolution data for both (resolution for MS1 and MS2 were set at 30,000 and 7,500, respectively). To account for the increased scan time, only the five most abundant parent ions were selected for fragmentation per cycle (versus 30 if the spectra are collected in the ion trap). This produced an approximate cycle time of 3-5 s on an LTQ-Orbitrap Velos consistent with previous analysis[79]. The number of MS2 spectra collected per cycle was extended to ten if the data was generated on an Orbitrap Elite. Figures were generated from Xcalibur as described above and solely to clarify presentation of the chromatograms, the Boxcar smoothing function with 15 points provided as a standard feature of the Xcalibur analysis software was applied.

Once all peaks were confirmed as the active site peptide or fragmented tag, we could also manually identify the same spectral features in endogenously expressed AMD1 (FIGS.

7A-7E). The corresponding species with probe 2 required characterization by the same method due to a similar tag fragmentation pattern (FIGS. 7F-7I).

Characterization of Probe-Labelled Peptides of SCRN3 by isoTOP-ABPP

SCRN3 modified peptides were isolated as described for AMD1. The high-resolution spectra associated with the most abundant peptide pair was first manually assigned to a glyoxylyl-modified N-terminus by de novo sequencing using PEAKS 7.5 (Bioinformatics Solutions Inc.). The dominant and unique feature of the paired spectra is the pronounced $y_8$-ion that arises from fragmentation within the Leu7Pro8Pro9 motif in the SCRN3 N-terminus (FIG. 6D; FIG. 8C; FIGS. 9A-9D). In CID, because prolines are generally cleaved selectively at their N-terminal side to form abundant y-ions (known as the proline effect)[80], and, because this cleavage is generally enhanced when the preceding residue is a Leu (or Ile or Val) but suppressed when it is a Pro (or Gly), the resultant fragmentation heavily favors cleavage between Leu7 and Pro8. This highly abundant fragment ($m/z_{theor}$=869.4476±1 ppm) represents a diagnostic marker for the unmodified portion of the SCRN3 N-terminus. By contrast, the other fragmentation product, the $b_7$-ion, represents the portion that contains the modification and that is differentially labelled by the isotopic tags. Indeed, the $b_7$-ion is shifted appropriately (6 Da) when the spectra for the heavy and light peptides are compared. In addition, similar to the tag fragmentation observed for AMD1, the $b_7$-ion is detected as a series with an associated loss of $NH_3$ and $NH_3CO$, most likely from the tags. Lastly, because the $y_{13}$-ion could be detected with confidence in both heavy and light high-resolution spectra ($m/z_{theor}$=1400.7532+5 ppm), the modification site could be narrowed to be upstream of Thr8. This result was confirmed by gel analysis of SCRN3 mutants (FIG. 6E). The completely abolished labelling due to mutagenesis at a single site indicates that the labelling stoichiometry is one per protein. It was thus hypothesized that the N-terminal residue was most likely Cys6. However, a peptide that begins with Asp7 and acquires a mass addition (instead of a loss) of 65 Da was considered at this stage. Regardless of the scenario, an N-terminal Cys6-derived glyoxylyl group was a chemically reasonable electrophile expected to react with the probes that gave the measured mass within a 10 ppm error limit.

Computational Search Strategies to Identify SCRN3 N-Termini

In general, most peptide identification software requires knowledge of the predicted parent mass of a peptide a priori in order to sequence that peptide using a database[78,81-84]. In other words, the mass shift of a modification must be intentional or predicted. Because the site and structure of the electrophiles in SCRN3 were completely unknown, the IP2 software used to analyze profiling data was not initially a viable search strategy to uncover this PTM.

A tailored computational search strategy was developed to ensure that in each experiment all forms of the SCRN3 N-terminus could be accounted for and that the glyoxylyl group was the dominant species labelled. For tag-specific samples with peptides labelled by probe 2, the data was first searched on the MS1 level for paired spectra (Table 6) of co-eluting peaks. For this program, every recorded monoisotopic precursor mass was searched 6.0138 Da (±5 ppm) upstream and downstream in each total ion (MS1) spectrum for a possible isotopic partner taking into account +2 and +3 charge states differences (3.0069 and 2.0046 Da, respectively). Here, the relative intensity of the monoisotopic peak was required to be ≥5% of the base peak of each spectrum, at least three peaks were required to exist in each isotope profile (envelope) and the Euclidean distance between the two isotope profiles was required to be <0.2. Next, pairs with the same m/z values (±5 ppm) and retention times (±10 min) were grouped to eliminate duplicates. Pairs of parent ions were analyzed from SCRN3-transfected versus mock-transfected cells.

TABLE 6

Average m/z values and absolute intensities for light-tagged parent ions of probe 2 pairs detected from SCRN3- versus mock-transfected cells that were at least 20% of the maximum pair intensity.

| structure | $[M + H]^+$ theoretical (tag$_{light}$) | $[M + H]^+$ measured (tag$_{light}$) | detection frequency* | charge state | m/z average | stdev | Intensity$_{max}$ (×10$^4$) SCRN3 1 | 2 | 3 | mock 1 | 2 | SCRN3- dependent detection | Intensity as SCRN3 N-terminus |
|---|---|---|---|---|---|---|---|---|---|---|---|---|---|
| glyoxylyl | 2,141.0887 | 2,141.0866 | 3/3 | 2 | 1,071.0472 | 0.0008 | 50 | 853 | 1194 | — | — | ✓ | ✓ |
|  |  |  | 3/3 | 3 | 714.3676 | 0.0010 | 56 | 733 | 1,021 | — | — | ✓ | ✓ |
| pyruvoyl | 2,155.1043 | 2,155.1038 | 3/3 | 2 | 1,078.0556 | 0.0012 | 27 | 557 | 473 | — | — | ✓ | ✓ |
|  |  |  | 3/3 | 3 | 719.0400 | 0.0010 | 32 | 751 | 534 | — | — | ✓ | ✓ |
| unknown | — | 2,314.1713 | 2/3 | 3 | 772.0622 | 0.0001 | 39 | — | 277 | — | — | ✓ | ✓ |

*from SCRN3 transfection replicates (1-3)

This search was valuable because it allowed all probe-labelled peptides regardless of their mass or identity to be distinguished from other ions in the sample by their unique pair feature with a defined mass differential. Pairs of parent ions were analyzed from three biological replicates that contained probe 2-labelled peptides isolated from SCRN3-transfected cells (Table 6). In each replicate, the most abundant pairs, based on direct mass ion intensity measurements, were tryptic peptides of the SCRN3 N-terminus that matched the masses for probe 2-hydrazone products of glyoxylyl and pyruvoyl N-terminal modifications. These pairs were the only two m/z species observed across all three replicates and were not identified in samples (two biological replicates) from mock-transfected cells, highlighting that their detection was robust and specific to SCRN3 transfection.

To confirm the results of parent ion pairing and to ensure that all SCRN3 N-terminal peptides were identified regardless of their paired state, a second program was developed to search the MS2 spectra for the diagnostic y-ions of the SCRN3 N-terminus. Here, at least four y-ions must be detected in a spectra (±50 and 400 ppm for high- and low-resolution spectra, respectively) and the diagnostic $y_8$-ion must be at least 80% more abundant than the other y-ions identified. To guarantee that downstream structure determination was based on the correct precursor mass, RawConverter[8] was used to extract accurate monoisotopic m/z values for each MS2 spectra.

For a single replicate that was analyzed for pairs above, the top two most abundant were indeed tagged, paired species of the probe 2-labelled glyoxylyl and pyruvoyl N-termini. This SCRN3-specific y-ion search facilitated the identification of reductively aminated peptides, stoichiometry measurements using reductive aniline exchange, and characterization of the protein isolated from *E. coli*.

Specificity of Spectra Assignments for the SCRN3 N-Terminus

The spectra assignments were validated by applying the corresponding light and heavy mass shifts for glyoxylyl and pyruvoyl modifications labelled by probe 2 (+522.29929 and 528.31309 Da versus 536.3149 and 542.3287 Da versus, respectively when cysteine residues are also specified with a static modification for carbamidomethylation) in an IP2 search against the full Uniprot database (see above). The search parameters were set as described above except for the differential modifications mentioned and that only one peptide per protein was required for identification. For the cysteine-to-glyoxylyl search, 744 total spectral counts of labelled SCRN3 peptides were measured: 321 and 423 of the light and heavy forms of the N-terminus, respectively. The false positive hit rate for this search was computed as 0.8%. For the cysteine-to-pyruvoyl search, 538 total spectral counts of labelled peptides from SCRN3 were measured: 273 and 254 of the light and heavy forms of the N-terminus, respectively. The false positive hit rate for this search was computed as 0.7%. The results confirm that each spectrum is indeed best matched to the SCRN3 N-terminus when analyzed against all other predicted spectra of labelled tryptic peptides in the proteome.

Co-Elution with Synthetic Standards

The tagged peptide pairs of SCRN3 labelled with probe 2 were isolated as described above in Example 2 with the exception that the cells were grown in standard SILAC media. The sample was analyzed in the absence and presence of 0.5 μmol of natural abundance synthetic standards also modified with probe 2 and conjugated with the tags. The standards were synthesized as described below in Example 5 and added to the digested sample just prior to column loading for analysis.

Incorporation of Heavy Cysteine into the SCRN3 N-Terminus

The tagged peptide pairs of SCRN3 labelled with probe 2 were isolated and analyzed as described above with the exception that the cells were grown in L-cysteine- and L-methionine-free DMEM (Thermo Fisher Scientific, 21013-024) supplemented with natural abundance L-methionine (0.2 mM, Sigma) and L-[$^{15}$N$^{13}$C$_3$]cysteine (0.4 mM, Cambridge Isotopes).

Reductive Amination in the Absence of Probes

Soluble SCRN3-transfected lysates (~0.25 mg each in ~200 μL PBS) were treated with natural abundance or $^{15}$N-enriched $(NH_4)_2SO_4$ (2 M) in the presence of $NaBH_3CN$ (100 mM) overnight at ambient temperature.

SCRN3 was purified from each sample via its FLAG affinity tag as described for AMD1 with the exception that the gel-bound protein was digested by rehydration with 0.4 μg trypsin (reconstituted in PBS) and further diluted to ~200 μL with 25 mM ammonium bicarbonate instead of triethylammonium bicarbonate. The samples were incubated at 37° C. overnight, acidified with 5% formic acid and analyzed separately by the same method described for proteomic profiling in Example 2.

Reductive Hydrazone Exchange with Aniline

Probe 2-treated SCRN3-transfected cells grown in heavy SILAC media were lysed in PBS (pH 7.4) and fractionated. The soluble proteome was supplemented with 100 mM aniline and 20 mM $NaBH_3CN$ in the presence of 2% Triton X-100 and 0.2% SDS. The pH of the lysate was reduced to ~6-6.5 with phosphate buffer to facilitate the exchange reaction, which is optimal at pH 4.5[85]. The partially precipitated proteome was incubated overnight at ambient temperature. The next day the sample was diluted to 1 mL with 50 mM Na-HEPES buffer (pH 7.5) supplemented with 500 mM NaCl and 1% Triton X-100. Unsolubilized protein that remained in the sample was pelleted by centrifugation and denatured with a small volume 10% SDS for 1 hour at 37° C. before recombining with the diluted reaction ensuring that the final concentration of SDS did not exceed ~0.2%. The completely resolubilized sample was incubated overnight at 4° C. by rotation with anti-FLAG resin as described above. The next day the resin was washed by resuspension and centrifugation with the same buffer supplemented only with 500 mM NaCl (5×1 mL) followed by 100 mM NaCl (2×1 mL). The bound protein was eluted by incubating the beads for ~1 h at 37° C. in PBS containing 8 M urea (2×50 μL). Cysteines were reduced with TCEP (10 mM preneutralized with 30 mM potassium carbonate for 30 min at 37° C.) and alkylated with iodoacetamide (20 mM under the same conditions but protected from light). The samples were diluted to 2 M urea with PBS and digested at 37° C. overnight with 2 μg trypsin supplemented with 1 mM $CaCl_2$. Trypsin was inactivated with 5% formic acid.

The natural abundance probe 2-labelled glyoxylyl6-Arg20 peptide standard was diluted in PBS supplemented with 100 mM aniline and 20 mM $NaBH_3CN$. The pH was reduced to 6.5 with phosphate buffer and the sample was incubated overnight at ambient temperature. Just prior to analysis by the same method used for proteomic profiling described in Example 2, the digested SCRN3 sample was doped with the aniline standard as well as Ala126-Lys136, an internal peptide that represents the total protein (5-50 pmol of each). Absolute amounts of standards were adjusted to achieve nearly comparable peak intensities for quantitation.

Fraction of Cysteine N-Terminus of SCRN3

SCRN3-transfected HEK293T cells were grown in heavy SILAC media and the protein was purified and proteolyzed as above. The sample was doped with known amounts of Ala126-Lys136 (5-50 pmol) and unmodified Cys6-Arg20 (2-10 pmol) standards that had been reduced and alkylated under the same conditions as the SCRN3 digest.

Expression and Purification of SCRN3 from *E. coli*

First, an internal NdeI restriction site naturally found in the SCRN3 gene sequence was silently mutated to preserve the amino acid sequence and allow cloning into the pET-30b(+) vector at NdeI and NotI restriction sites. The plasmid was engineered to ensure that no nonnative residues were appended to the N-terminus of the protein whereas an additional 11 amino acids ($A_3LEH_6$) (SEQ ID NO: 48) were appended to the C-terminus for detection and purification. Growth of the expression strains and purification of the protein was performed as described previously[86]. A typical yield was 5 g of wet cell paste per liter of culture. The frozen paste (~1 g) was resuspended (5 mL/g) in 50 mM Na-HEPES buffer (pH 7.5) containing 300 mM NaCl, 5 mM imidazole, 0.1 mg/mL Dnase I, 1 mM $CaCl_2$ and 1 mM $MgCl_2$. The cells were lysed at 4° C. by sonication and cell debris was pelleted by centrifugation (16,000 g, 10 min, 4° C.). The supernatant was incubated with Ni-NTA resin and purified as described above. Protein fractions were pooled and buffer exchanged into 50 mM Na-HEPES buffer (pH 7.5) containing 100 mM NaCl using PD10 columns (GE Amersham). The protein was concentrated to ~5 mg/mL prior to being flash-frozen with 10% glycerol and stored at ~80° C. The yield was ~10 mg protein (>80% purity by SDS-PAGE) per g of cell paste.

Probe Labelling of *E. coli* Cells Expressing SCRN3 Versus AMD1

Induced overnight cultures expressing each protein were resuspended in serum-free DMEM supplemented with 10 mM Na-HEPES buffer (pH 7.5) such that the final $OD_{600}$ was ~10. The probes were added to the cells (3 and 1 mM, respectively, for 1 and 2) and incubated at 37° C. for 0.5 hour. Note that these are the same conditions used for treatment of mammalian cells. The cells were pelleted (16,000 g, 3 min, 4° C.), washed with PBS (2×1 mL), and resuspended in HEPES buffer or PBS maintaining the same initial volume. Cells were lysed by sonication, debris was pelleted, soluble protein was diluted to 0.5 mg/mL with PBS and probe-labelled proteins were conjugated to rhodamine-azide and visualized as described above in Example 2.

Characterization of the N-Terminus of SCRN3 Produced in *E. coli*

A 25 µL solution of ~20 µM purified SCRN3 (~30 µg) was diluted with 6 M urea in PBS. Disulfides were reduced with TCEP (10 mM) pre-neutralized with potassium carbonate (30 mM) for 30 minutes at 37° C. Reduced thiols were alkylated by iodoacetamide (20 mM) for 30 minutes at ambient temperature protected from light. The solution was diluted to 2 M urea with PBS (~350 µL total volume) and digested overnight at 37° C. with sequencing grade porcine trypsin (2 µg) (Promega) in the presence of $CaCl_2$ (1 mM). Digested peptides were acidified with 5% formic acid and ~5 µg digested protein (70 µL aliquot of the digest) was analyzed as described for reductive amination and aniline capture samples utilizing the y-ion search to identify all SCRN3 N-termini present in protein generated from bacteria (Table 7).

TABLE 7[1]

SCRN3 N-termini identified from protein produced in *E. coli*.

| SCRN3 N-terminus | $[M + H]^+_{measured}$ | $[M + H]^+_{theoretical}$ | mass error (ppm) | $Intensity_{max}$ (x $10^4$) replicate 1 | replicate 2 |
|---|---|---|---|---|---|
| C*DTFVALPPATVDNR | 1,675.8038 | 1,675.8108 | −4.2 | 57 | 84 |
| MEPFSC*DTFVALPPATVDNR | 2,267.0390 | 2,267.0471 | −3.6 | 45 | 17 |
| SC*DTFVALPPATVDNR | 1,762.8345 | 1,762.8429 | −4.8 | 18 | 19 |
| DTFVALPPATVDNR | 1,515.7712 | 1,515.7802 | −5.9 | 5.8 | 6.3 |

*indicates mass shift (57.02146) applied to cysteine for standard carbamidomethylation with iodoacetamide

[1]SCRN3 N-terminus sequences (SEQ ID NOs: 25 and 49-51)

Results

Figure 10:
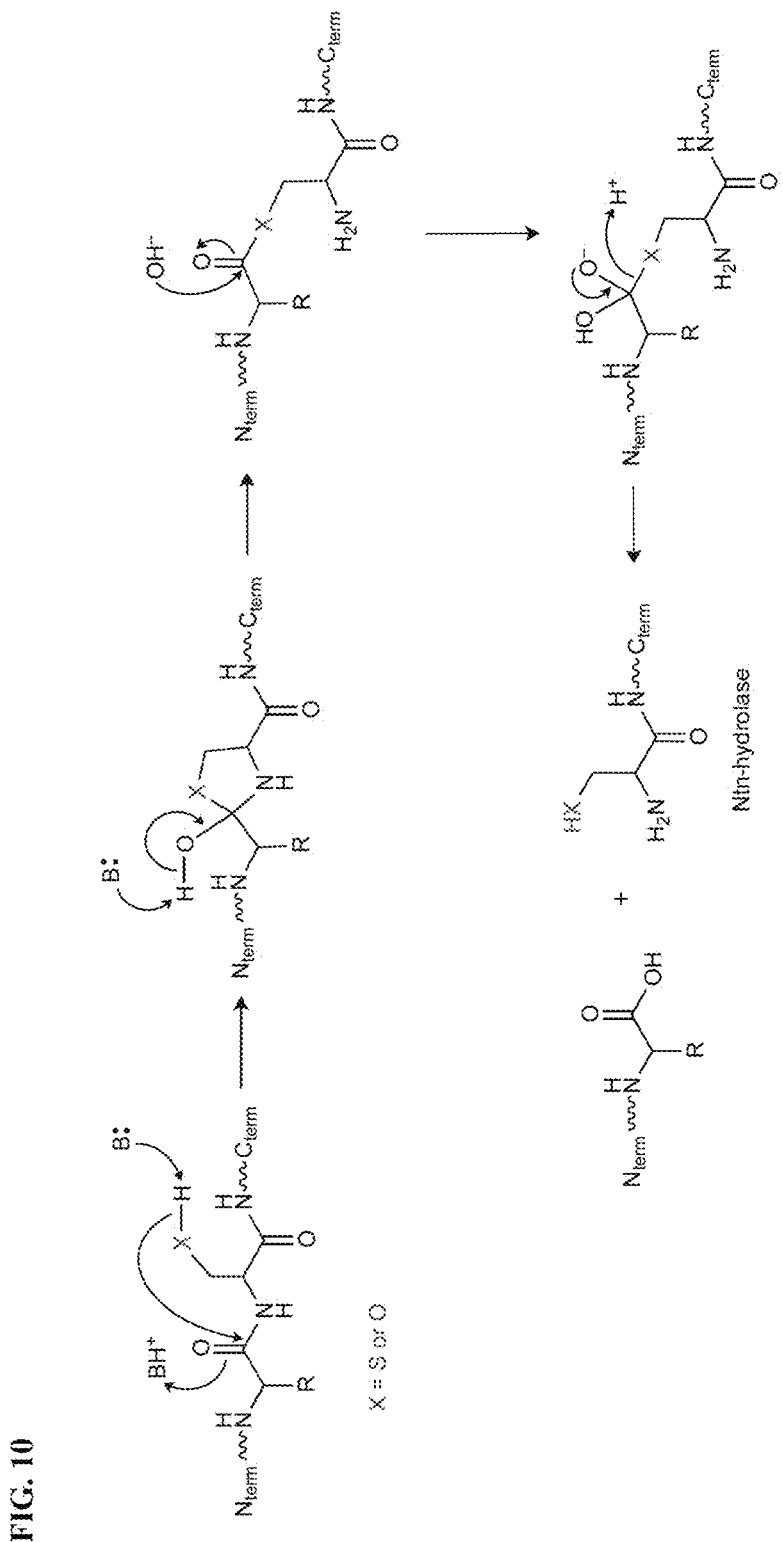
FIG. 10 shows a schematic of autoprocessing of N-terminal nucleophile (Ntn) hydrolases; threonine, serine, and cysteine can initiate N→O or N→S acyl shifts to form tetrahedral cyclic intermediates that reopen as (thio)esters; hydrolysis generates the N-terminal catalytic nucleophile of the active enzyme.

First, it was confirmed that isoTOP-ABPP correctly assigned the site of probe 1 (and 2) reactivity in AMD1 as the N-terminal pyruvoyl modification using both recombinant and endogenous sources of the enzyme (FIGS. 7A-7I). Next selected for analysis Secernin-3 (SCRN3), a poorly characterized protein from the target list that reacted with both probes 1 and 2 (Table 2) and is predicted on the basis of sequence to be an N-terminal cysteine nucleophile (Ntn) hydrolase (FIG. 6B)[35]. Based on these predictions, $Cys_6$ of SCRN3 would serve as the N-terminal nucleophile responsible for autoproteolytic processing via a mechanism that is shared by other Ntn hydrolases[36,37] (FIG. 10). However, to our knowledge, SCRN3 has not been experimentally verified to undergo this type of N-terminal processing. SCRN3-transfected HEK293T cells were treated with probe 2 (1 mM, 0.5 h), lysed, conjugated to a 1:1 ratio of isotopically heavy and light biotin-azide tags, and enriched on streptavidin beads. Enriched proteins were then digested on-bead by sequential proteolysis, first with trypsin to remove unlabelled peptides, followed by TEV protease to release probe-labelled peptides, which were analyzed by LC-MS/MS, where authentic probe-labelled peptides were expected to migrate as isotopically differentiated mass pairs with a heavy:light ratio of 1. The most abundant probe-labelled peptide pair that conformed to these specifications (FIG. 6C; and Table 6) was both manually and computationally identified as a half-tryptic peptide spanning from $Cys_6$ to $Arg_{20}$ of SCRN3 based on the pattern of y-ions in the high-resolution tandem mass spectra (FIG. 6D, left). Importantly, the $y_{13}$-ion assigned the probe modification site to one of the first two residues (FIG. 6D, right), which was supported by mutation of either residue —$Cys_6$ or $Asp_7$—which abolished probe 2 labeling (FIG. 4E). Similar data were obtained for SCRN3-transfected cells treated with probe 1 (FIGS. 9A-9D).

Figure 11:
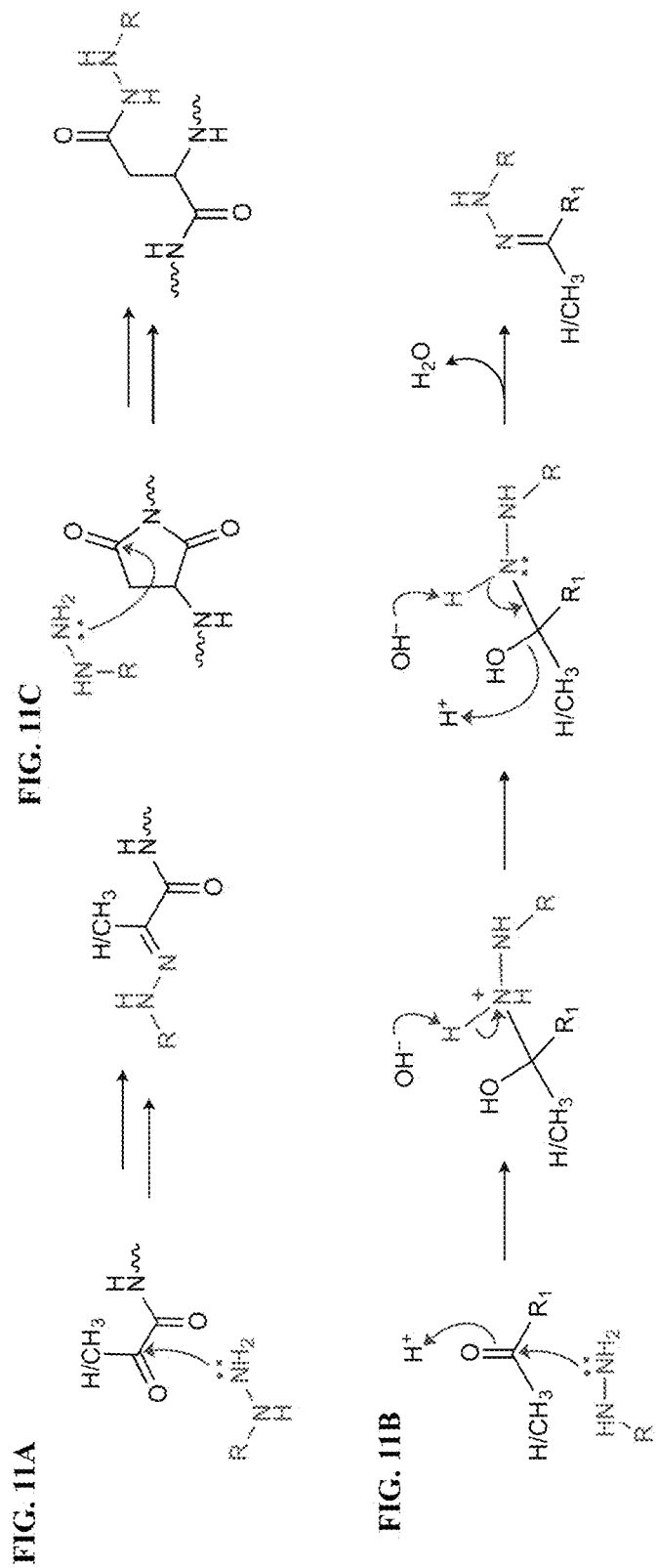
FIGS. 11A-11C show probe-capture chemistry of protein electrophiles.

The data accumulated thus far indicated that (i) SCRN3 contains a hydrazine-reactive group at or near $Cys_6$, which represented the presumed N-terminus of the protein, as predicted by the activation mechanism for Ntn proteins (FIG. 10); and (ii) electrophile formation and subsequent reaction with probe 1 or 2 yielded a net loss of 65 Da from the summated mass of an unmodified N-terminal $Cys_6$-$Arg_{20}$ peptide combined with the masses of the hydrazine probes (FIG. 6F, upper). The most logical structure conceived to fit these criteria was the hydrazone product of a reaction between hydrazine probes and an N-terminal glyoxylyl group originating from $Cys_6$ (FIG. 6F, lower and FIGS. 11A and 11B).

To test these structural predictions, a peptide standard was synthesized for the hydrazone product of a probe 2-$Glyoxylyl_6$-$Arg_{20}$ reaction and then combined the standard with proteomic lysates prepared from probe 2-treated SCRN3-transfected HEK293T cells that had been grown in heavy arginine/lysine, such that the peptide standard and probe 2-labelled endogenous SCRN3 peptide would be isotopically distinguishable (FIG. 8A). Note that these experiments were performed with probe 2 rather than probe 1 because probe 2 appeared to produce higher product yields with SCRN3 (FIG. 3D). The peptide standard and the 2-labelled endogenous SCRN3 peptide co-eluted by LC (FIG. 8B) and displayed tandem mass spectra that differed by the predicted 10 Da in the $y_8$-ion containing the heavy C-terminal Arg residue, but were identical across the b7-ion series lacking this residue (FIG. 8C). These data supported the structural assignment that SCRN3 possesses an N-terminal glyoxylyl group originating from the conserved $Cys_6$ residue.

Figure 12:
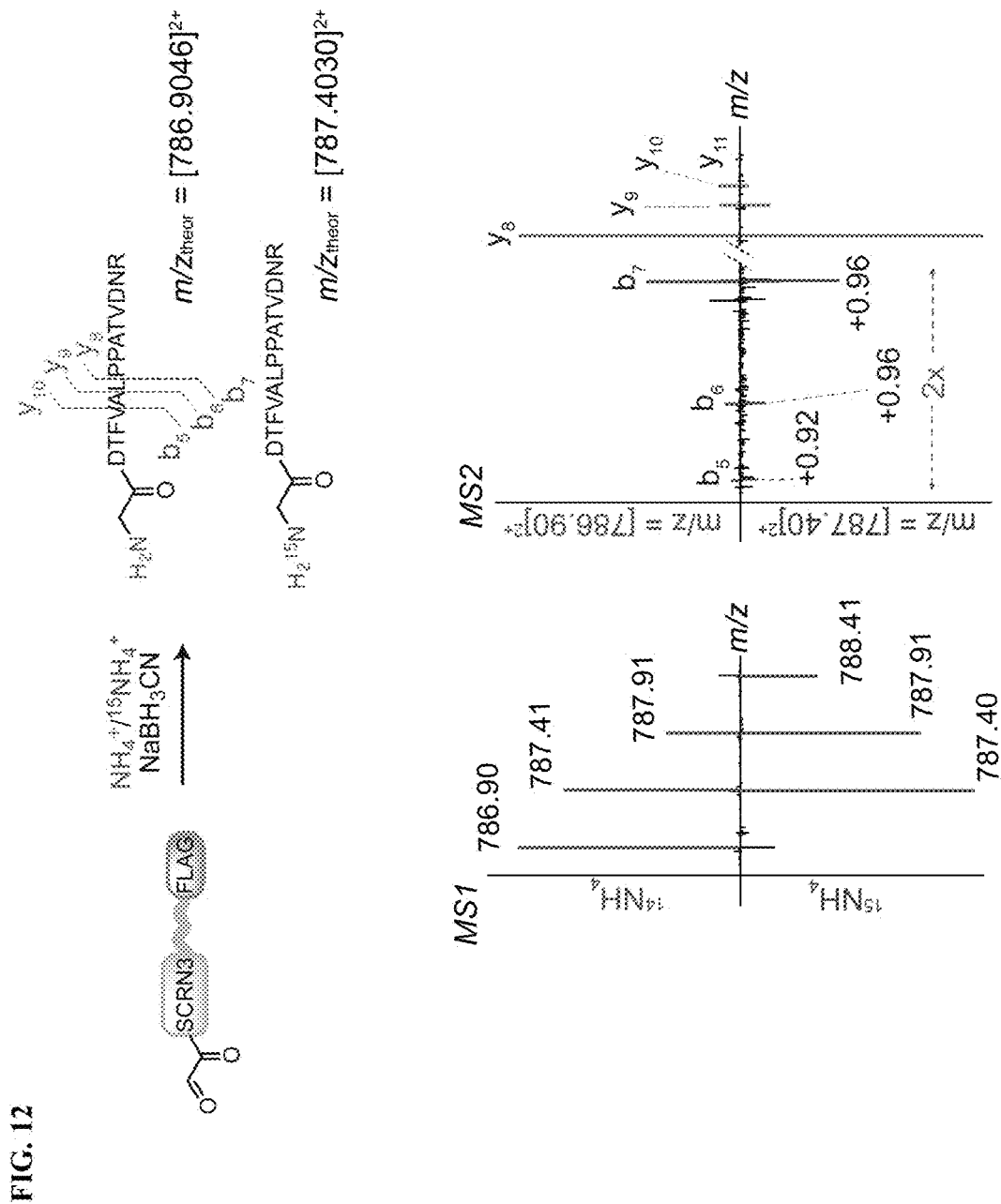
FIG. 12 shows evidence for the glyoxylyl modification of SCRN3 by reductive amination; a glycine N-terminus is produced by reductive amination (SEQ ID NO: 30) with $(NH_4)_2SO_4$ in lysates of SCRN3-transfected cells (upper scheme); doubly-charged MS1 (left) and MS2 (right) spectra for the reaction with natural abundance (red) versus $^{15}$N-enriched (blue) $(NH_4)_2SO_4$; the parent mass and b-ions that contain the N-terminal residue shift accordingly 1 Da; this alternative chemical derivatization supports the authenticity of the glyoxylyl group.

Additional confirmation was obtained for the N-terminal glyoxylyl modification of SCRN3 by subjecting SCRN3-transfected cell lysates to reductive amination with $(NH_4)_2SO_4$, which furnished the predicted N-terminal glycine peptide ($Gly_6$-$Arg_{20}$) for the trypsin-digested, affinity-purified SCRN3 protein (FIG. 12). The parent mass for this peptide (FIG. 12, left) and its corresponding b-, but not y-ions (FIG. 12, right) also shifted in mass by 1 Da when $(NH_4)_2SO_4$ was substituted with $^{15}$N-enriched $(NH_4)_2SO_4$.

Further analysis of the MS data from SCRN3-transfected cells (Table 5) identified another prominent probe 2-enriched product that matched the predicted mass for an N-terminal pyruvoyl modification of SCRN3 (Table 7). This product was detected with ~50% of the ion intensity of the N-terminal glyoxylyl modified SCRN3 (FIG. 13A). Both the N-terminal glyoxylyl and pyruvoyl forms of recombinant SCRN3 were also observed with alkyl probe 1 (Table 8), and their relative intensities preserved under different sample preparation conditions (FIG. 13B), suggesting that both electrophilic modification states occur for SCRN3 in situ.

Figure 13D:
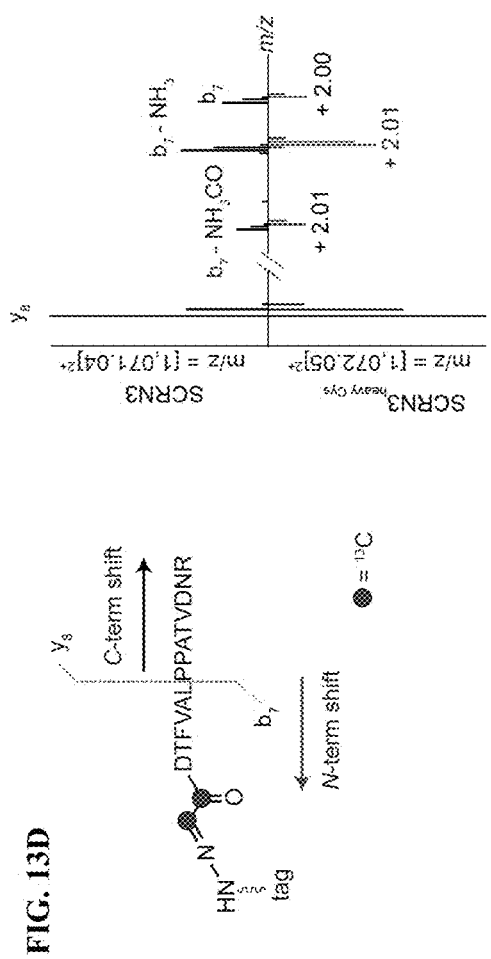

In support of the pyruvoyl structure assignment and a model for glyoxylyl formation that involves an apparent $2e^-$ oxidation of the N-terminal Cys residue of SCRN3 via Cα-Cβ bond cleavage and oxidative deamination, we found that SCRN3-transfected cells grown in media supplemented with L-[$^{15}$N$^{13}$C$_3$]cysteine shifted the parent mass and $b_7$-ion series, but not $y_8$-ion for the probe 2-labelled pyruvoyl peptide by the expected 3 Da (FIG. 13C) and the corresponding glyoxylyl peptide by the expected 2 Da (FIG. 13D). In contrast, internal peptides that contained a Cys residue shifted the expected 4 Da in parent mass, accounting for all 4 heavy atoms of the Cys residue (Table 9).

TABLE 8

Mass error for heavy- and light-tagged N-termini of SCRN3.

| SCRN3 N-terminal modification | probe | SCRN3 sequence | experimental conditions | [M + H]$^+_{measured}$ tag$_{light}$ | [M + H]$^+_{measured}$ tag$_{heavy}$ | [M + H]$^+_{theoretical}$ tag$_{light}$ | [M + H]$^+_{theoretical}$ tag$_{heavy}$ | mass error (ppm) tag$_{light}$ | mass error (ppm) tag$_{heavy}$ |
|---|---|---|---|---|---|---|---|---|---|
| glyoxylyl | 1 | WT | natural abundance | 2,008.0360 | 2,014.0478 | 2,008.0360 | 2,014.0498 | 0.0 | −1.0 |
| | 2 | Met1Cys6 mutant | natural abundance | 2,141.0863 | 2,147.1003 | 2,141.0887 | 2,147.1025 | −1.1 | −1.0 |
| | | WT | | 2,141.0885 | 2,147.1008 | | | −0.1 | −0.8 |
| | | — | synthetic standard | 2,141.0916 | 2,147.1044 | | | 1.4 | 0.9 |
| | | WT | SILAC: Arg$_{heavy}$ (+10.00826) | 2,151.0990 | 2,157.1112 | 2,151.0970 | 2,157.1108 | 0.9 | 0.2 |
| | | | Cys$_{heavy}$ [+2(1.0034)] | 2.143.0950 | 2,149.1068 | 2,143.0955 | 2,149.1093 | −0.2 | −1.2 |
| pyruvoyl | 1 | WT | natural abundance | 2,022.0506 | 2,028.0638 | 2,022.0515 | 2,028.0653 | −0.4 | −0.7 |
| | 2 | Met1Cys6 mutant | natural abundance | 2,155.1013 | 2,161.1151 | 2,155.1043 | 2,161.1181 | −1.4 | −1.4 |
| | | WT | | 2,155.1034 | 2,161.1179 | | | −0.4 | −0.1 |
| | | WT | SILAC: Arg$_{heavy}$ (+10.00826) | 2,165.1162 | 2,171.1286 | 2,165.1126 | 2,171.1264 | 1.7 | 1.0 |
| | | | Cys$_{heavy}$ [+3(1.0034)] | 2,158.1108 | 2,164.1258 | 2,158.1145 | 2,164.1283 | −1.7 | −1.2 |

TABLE 9[1]

Incorporation of L-[$^{15}$N$^{13}$C$_3$]cysteine into unmodified SCRN3 peptides (related to FIGS. 13C and 13D) produces a mass shift of 61 Da (4 Da increase from the 57 Da mass shift applied for standard carbamidomethylation of cysteines).

| sequence | spectral counts | [M + H]$^+_{theoretical}$ | [M + H]$^+_{measured}$ | mass error (ppm) |
|---|---|---|---|---|
| K.C(61.0349)TYIEIDQVPETYAVVLSR.P | 10 | 2,260.1350 | 2,260.12947 | −2.4 |
| R.EEVC(61.0349)DEEALLGMDLVR.L | 11 | 1,881.8754 | 1,881.8678 | −4.0 |
| K.IVNLFPQC(61.0349)TK.D | 8 | 1,223.6638 | 1,223.6554 | −6.9 |

TABLE 9[1]-continued

Incorporation of L-[$^{15}$N$^{13}$C$_3$]cysteine into unmodified SCRN3 peptides (related to FIGS. 13C and 13D) produces a mass shift of 61 Da (4 Da increase from the 57 Da mass shift applied for standard carbamidomethylation of cysteines).

| sequence | spectral counts | [M + H]$^+_{theoretical}$ | [M + H]$^+_{measured}$ | mass error (ppm) |
| --- | --- | --- | --- | --- |
| K.YGQGGNC(61.0349)TEGR.M | 1 | 1,202.5040 | 1.202.4949 | −7.6 |
| K.ALNVIVDLLEK.Y | 21 | 1,226.7355 | 1,226.7352 | −0.3 |
| K.EFDFAAAYSYLDTAK.M | 18 | 1,711.7850 | 1,711.7857 | 0.4 |
| K.KSHFKPDR.R | 10 | 1,014.5479 | 1,014.5477 | −0.2 |
| R.NISNQLSITTK.I | 8 | 1,218.6688 | 1,218.6676 | −1.0 |
| K.DEIQIYQSNLSVK.V | 8 | 1,536.7904 | 1,536.7867 | −2.4 |
| K.GNITFETMMEILR.D | 7 | 1,554.7654 | 1,554.7662 | 0.5 |
| R.NEAWILETAGK.Y | 5 | 1,231.6317 | 1,231.6291 | −2.1 |
| K.HQQALEVVNNNEEK.A | 5 | 1,651.8035 | 1,651.8015 | −1.2 |
| H.ISQLLDTSSPTFELEDLVK.K | 4 | 2,135.1118 | 2,135.1109 | −0.4 |
| R.RHPLYQK.H | 4 | 941.5316 | 941.5319 | 0.3 |
| K.IMLDNMR.K | 2 | 892.4379 | 892.4368 | −1.3 |
| R.MVFSYHNSF.L | 1 | 1,131.4928 | 1,131.4906 | −1.9 |
| K.SHFKPDRR.H | 1 | 1,042.5541 | 1,042.5532 | −0.8 |

[1]sequences: SEQ ID NOs: 52-68

Figure 14A:
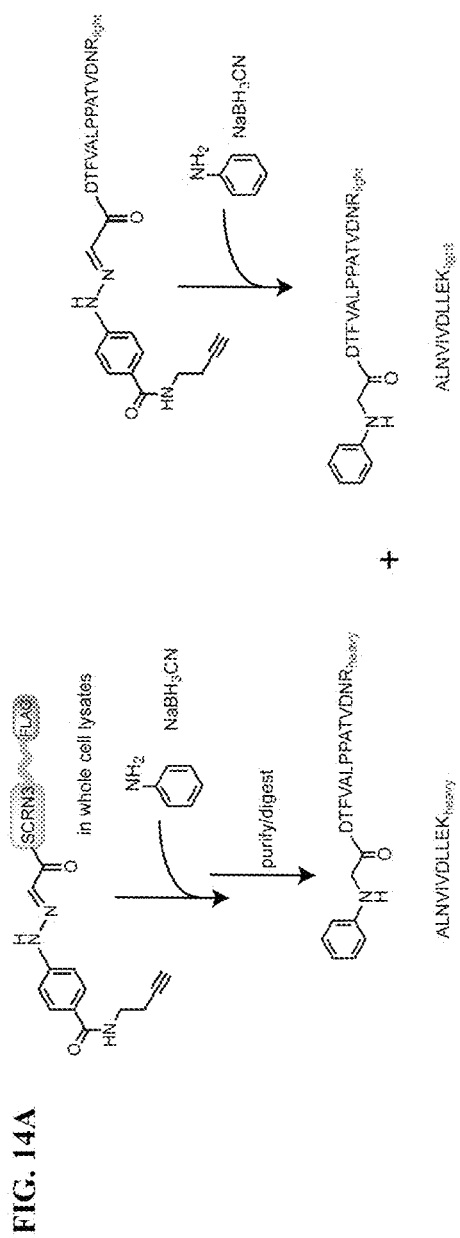
FIGS. 14A-14D show the stoichiometry of the glyoxylyl-modified isoform of SCRN3 in cells.
Figure 14B:
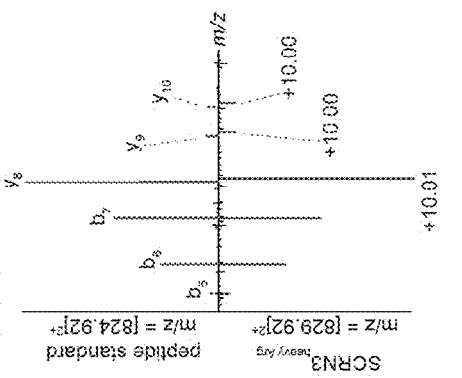
Figure 14C:
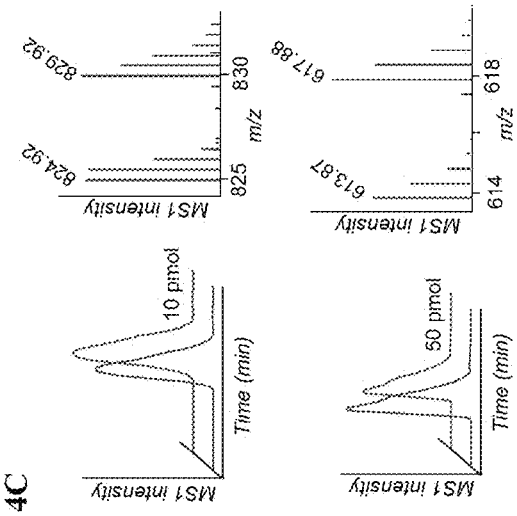
Figure 14D:
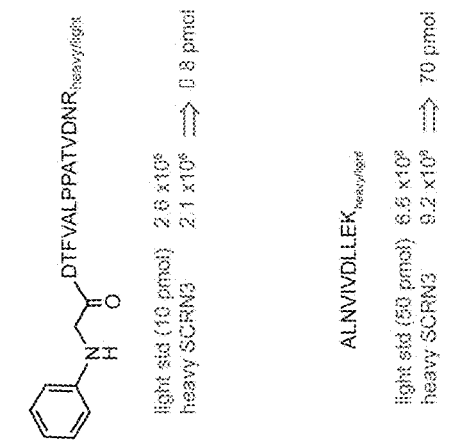
Figure 15B:
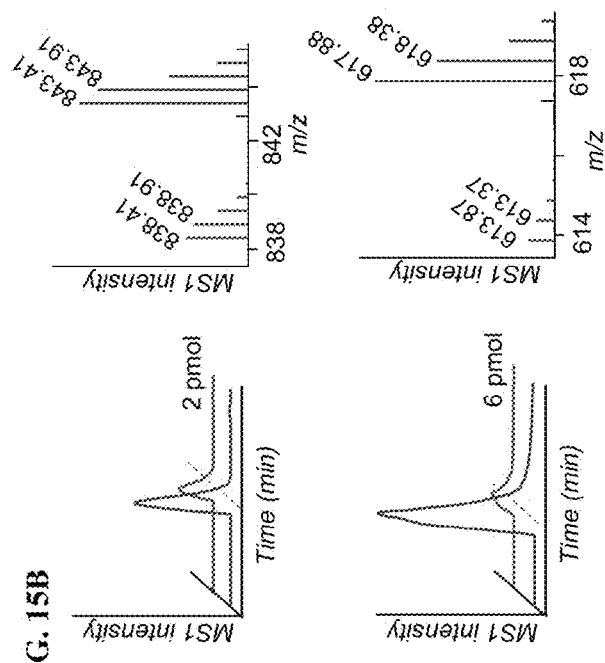
FIGS. 15A and 15B show the stoichiometry of the unmodified isoform of SCRN3 in cells.
Figure 15A:

As an initial attempt to estimate the fraction of SCRN3 protein bearing the N-terminal glyoxylyl modification, we reacted lysates from probe 2-treated SCRN3-transfected (and heavy amino acid-labelled) HEK293T cells with aniline to generate an iminium adduct that could be reduced with NaCNBH$_3$ to a more stable amine product (FIGS. 14A and 14B), following the reactivity trends that have been exploited in bioconjugation approaches[38,39]. An aniline-modified and reduced glyoxylyl N-terminal SCRN3 peptide standard, along with a control standard for an internal SCRN3 tryptic peptide were synthesized, and the ratios of heavy parent ion peak intensities for the aniline-modified N-terminal and internal peptides with near-equivalent amounts of the corresponding peptide standards were compared (FIGS. 14C and 14D). The ratios of the aniline-appended N-terminal and internal peptides compared to their respective standards provided an estimate of 10±3% for the N-terminal glyoxylyl-modified SCRN3. This estimate was viewed as a lower limit for the fraction of glyoxylyl-modified SCRN3 in cells, since the probe 2 and aniline reactions with this form of SCRN3 may proceed with less than 100% efficiency in cell lysates, and it is also possible that, by overexpressing SCRN3 in transfected cells, the putative endogenous processing system that installs the glyoxylyl modification may have been saturated. At least partly supporting these hypotheses, it was estimated that only 15±3% (n=4) of the recombinant SCRN3 possessed an intact Cys$_6$ side chain in transfected cell preparations (FIGS. 15A and 15B).

Figure 17:
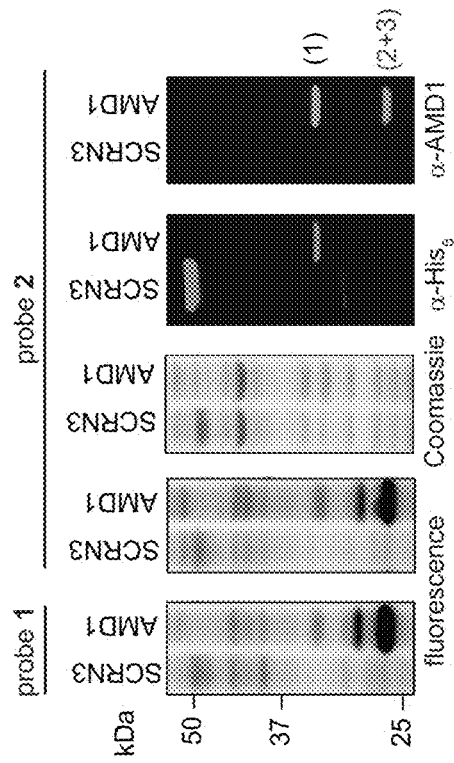
FIG. 17 shows the probe labelling of AMD1, but not SCRN3 in *E. coli* cells; *E. coli* cells expressing N-terminally His6-tagged AMD1 or C-terminally His6-tagged SCRN3 were treated with the indicated probe under the same conditions as FIG. 3D; the His6-tag is lost for the active form of AMD1; labels (1)-(3) for AMD1 are the same as those shown in FIG. 3D.
Figure 16:
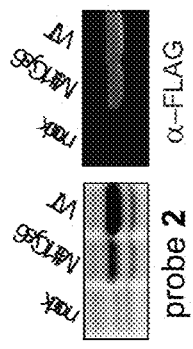
FIG. 16 shows probe labelling of an N-terminal deletion mutant of SCRN3; probe 2-labelling and expression profiles of HEK293T cells transfected with wild-type (WT) SCRN3 [M(EPFS)C-SCRN3], a deletion mutant with residues 2-5 removed (Met1Cys6), or the corresponding empty expression vector (mock)
Figure 18:
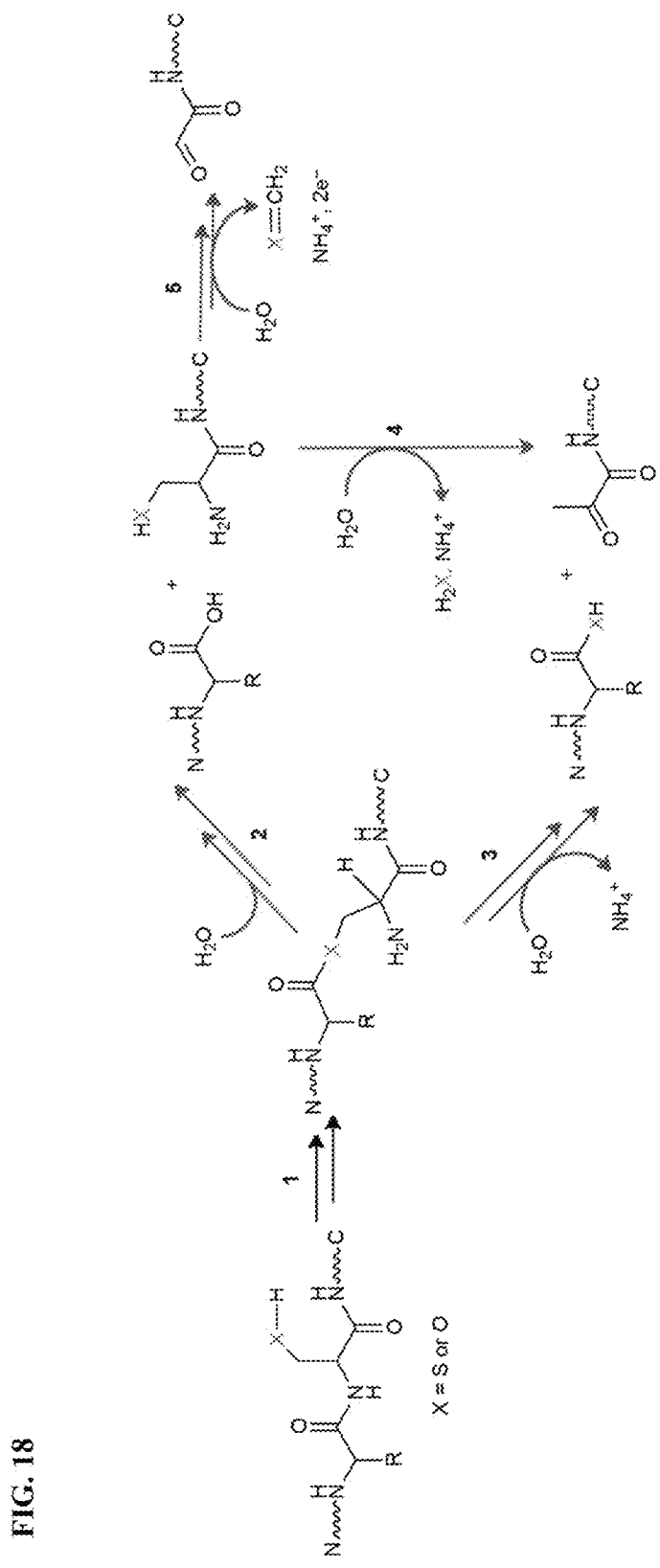
FIG. 18 shows possible routes for N-terminal processing of SCRN3 in comparison to the established mechanisms of N-terminal maturation for other protein classes; the mechanisms for Ntn hydrolases and pyruvoyl-dependent decarboxylases diverge at the transient ester intermediate formed during autoproteolysis (step 1); hydrolysis yields a catalytic nucleophile for Ntn hydrolases (step 2), whereas active site-directed β-elimination generates an electrophilic pyruvoyl cofactor for decarboxylases (step 3); detection of a new N-terminus containing an intact side chain, shown as a product of step 2, suggests that formation of pyruvoyl and glyoxylyl groups may occur via 4 and 5, respectively, in the N-terminal processing of SCRN3.
Figure 19:
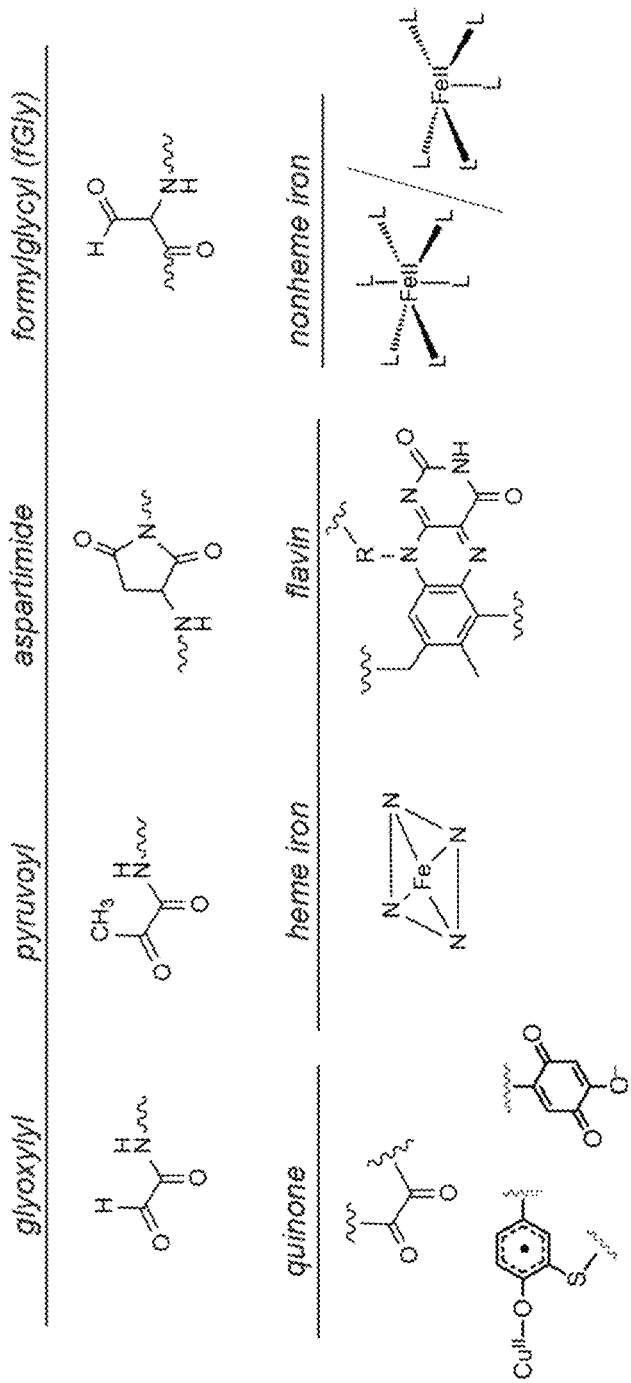
FIG. 19 shows examples of protein electrophiles that react with hydrazine and oxyamine probes; examples of electrophilic PTMs that react with hydrazines and oxyamines shown include glyoxyl, pyruvoyl, aspartimide, formylglycyl, and quinone; examples of oxidative PTMs that react with hydrazines and oxyamines shown include Flavin cofactors, heme iron cofactors, and may also include non-heme iron cofactors; hydrazine and oxyamine react with electrophilic PTMs by targeting the indicated electrophilic group installed onto a protein as a covalent modification; hydrazines and oxyamines react with oxidative PTMs by alkylating the indicated oxidative prosthetic group.

Finally, in initial attempts to assess features required for SCRN3's N-terminal glyoxylyl/pyruvoyl modifications, a variant of SCRN3 was evaluated in which amino acids 2-5 were deleted. It was found that this mutant protein was still converted to the glyoxylyl/pyruvoyl form, albeit with an apparently lower efficiency than the wild-type SCRN3 protein (FIG. 16 and Table 7). This result indicates that an N-terminal leader sequence is not required for SCRN3 processing or installation of its N-terminal electrophilic modifications. It was also found that SCRN3 reacts with hydrazine probes when expressed in mammalian cells, but not E. coli (FIG. 17). This contrasts with the profile of AMD1, which reacts well with probe 1 or 2 when expressed in E. coli (FIG. 17). These data are consistent with the established autonomous mechanism of installation for AMD1's pyruvoyl modification and suggest further that the N-terminal glyoxylyl/pyruvoyl groups in SCRN3 may require enzymatic machinery of the mammalian host cell for generation. In support of this hypothesis, LC/LC-MS/MS characterization of SCRN3 expressed and purified from bacteria failed to detect the N-terminal glyoxylyl/pyruvoyl states of the protein, instead revealing only the unprocessed N-terminus containing the initiator methionine residue and the Cys$_6$ N-terminus presumably generated by autocleavage (Table 6).

Figure 23A:
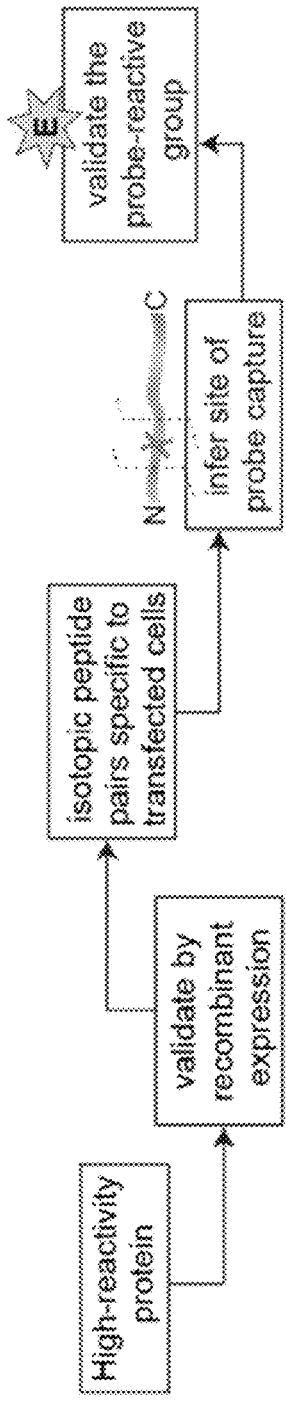
FIGS. 23A-23C show validation of the probe-3 reactive group in probe 3-treated KEAP1-transfected cells.
Figure 23C:
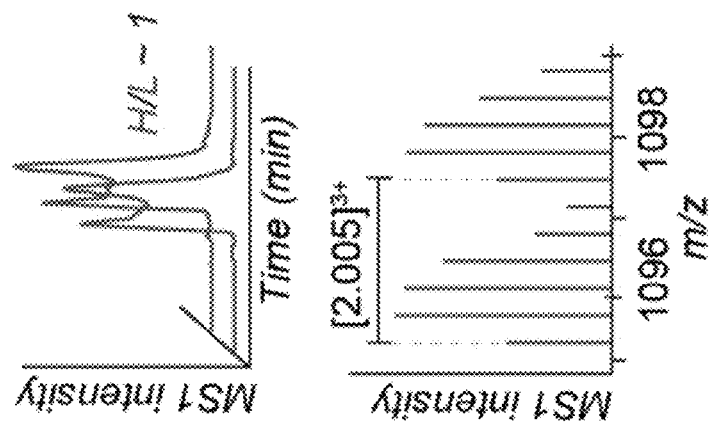
Figure 23B:
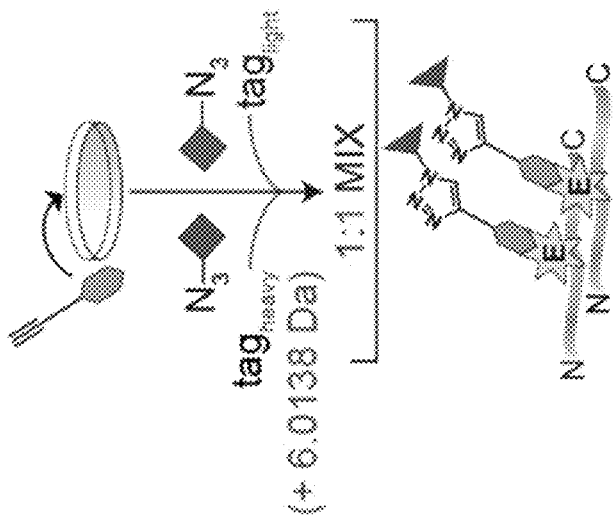

Iso-TOP-ABPP was also used to demonstrate that oxyamine probe 3 (FIG. 21A) can be used to capture and identify electrophilic PTMs on proteins, as shown using SCRN3 (FIGS. 22A-22C). The experiments described above were also repeated using probe 3 in KEAP-1 transfected cells as schematically shown in FIG. 23B. The results are shown in FIG. 23C, and demonstrate that oxyamine probes can be used to capture and identify sites of electrophilic PTMs on proteins.

Example 5: Synthesis of Probe-Labelled Peptides

The probe-labelled peptides used in Example 4 above were synthesized as described below.

Synthesis of probe 2-labelled glyoxylyl6-Arg20 peptides (SI-11$_{heavy/light}$)

Glyoxylyl$_6$-Arg20 Peptide (SI-7) (FIG. 26A)

The peptide acid (SI-6) was synthesized using manual synthetic cycles for 9-fluorenylmethoxycarbonyl (Fmoc) solid phase peptide synthesis[88]. Synthesis was performed on a 0.1 mmol scale using Wang resin preloaded with Fmoc-Arg(Pmc)-OH (0.54 mmol/g, Novabiochem). Couplings were performed for 20 min using Fmoc-protected amino acids (0.55 mmol) activated with 1H-benzotriazolium-1-[bis(dimethylamino)methylene]-5-chloro-hexafluorophosphate-(1-),3-oxide [HCTU; 0.5 mmol, 0.4 M in N,N-dimethylformamide (DMF)]and N,N-diisopropylethylamine (DIEA; 0.75 mmol, 131 μL). Fmoc deprotection was facilitated by treating with an excess of 20% 4-methyl-piperidine in DMF for a total of seven min. The peptide was cleaved from resin using trifluoroacetic acid (TFA):triisopropylsilane (TIS):H$_2$O (95:2.5:2.5) while agitating for 2.5 hours at ambient temperature. The TFA was 80% evaporated under N$_2$. The peptide was then precipitated by adding ice-cold diethyl ether, filtered and further washed. The crude peptide (SI-6) was dissolved in ammonium acetate (0.1 M, pH 4.5) and lyophilized. The mass was confirmed before proceeding to the next step. The N-terminal L-serine residue of the peptide (TFA salt: 55 mg, 32 μmol) was oxidized with sodium periodate (NaIO$_4$: 30 mg, 140 μmol, 4 eq.) in a small volume of H$_2$O for ~10 min. The glyoxylyl peptide product (SI-7) was purified by RP-HPLC (gradient: 15-30% 90:10 v/v MeCN/H$_2$O in H$_2$O, 0.05 v-% TFA in 30 min; flow rate: 15 mL/min) using a Phenomenex Jupiter 10 μm Proteo 90 Å (250×21.2 mm) column. The purity (>95%) and identity of the peptide was verified by RP-HPLC and ESI-MS, respectively. ESI-MS calc'd for $C_{69}H_{107}N_{18}O_{24}^{+}$ ([M+H]$^+$): 1,571.8, found 1,572.6; hydrated form: 1,589.8, found 1,590.8.

Hydrazone Product of Probe 2-Labelled Glyoxylyl6-Arg20 Peptide (SI-8) (FIG. 26B)

A solution of SI-7 (0.7 mM, 2.5 mg, 1.5 μmol) in ammonium acetate buffer (0.1 M, pH 4.5) was reacted under ambient conditions with probe 2 (6 mM, 3 mg, 13 μmol) in the presence of aniline (18.24 μL, 100 mM). A precipitate was observed after five minutes. The mixture was solubilized by adding ~30% acetonitrile. Aniline-catalyzed hydrazone formation was monitored by HPLC and was >90% complete in 1.5 hours. The hydrazone product (SI-8) was purified by RP-HPLC (gradient: 25-40% 90:10 v/v MeCN/H$_2$O in H$_2$O, 0.05 v-% TFA in 30 min; flow rate: 5 mL/min) using a Phenomenex Jupiter 5 μm C18 300 Å (150×10.0 mm) column. ESI-MS calc'd for $C_{80}H_{118}N_{21}O_{24}^{+}$ ([M+H]$^+$): 1,756.9, found 1,757.4.

Isotopic Protease-Cleaved Azide Tags (SI-10$_{heavy}$/SI-10$_{light}$) (FIG. 26C)

Stocks of SI-9$_{heavy}$ or SI-9$_{light}$, the biotin-azide tags[69] (0.25 μmol of each) that were used for enrichment and subsequent identification of labelled sites in AMD1 and SCRN3 were diluted to 250 μM with 1 mL of 50 mM Tris, pH 8 supplemented with 1 mM DTT in the presence of 0.4 M TEV protease. The residues in red represent the sequence recognition motif for the TEV protease, the dashed line indicates its cleavage site, and the differentially labelled valine atoms are shown in blue. The reaction was incubated overnight at 30° C. The next day the reaction was concentrated to ~200 μL and the protease was precipitated with an equal volume of acetonitrile. The supernatants containing the products were purified by RP-HPLC (gradient: 0-70% 90:10 v/v MeCN/H$_2$O in H$_2$O, 0.05 v-% TFA in 35 min; flow rate: 1 mL/min) using a Phenomenex Jupiter 5 μm C18 300 Å (150×4.6 mm) column. ESI-MS calc'd for $C_{15}H_{29}N_8O_4^{+}$ and $^{13}C_5C_{10}H_{29}^{15}NN_7O_4^{+}$ ([M+H]$^+$): 385.2 and 392.2, found 385.0 and 391.2, respectively for SI-10$_{light}$ and SI-10$_{heavy}$. The yield of the reaction was low, as major peaks for the uncleaved reactants remained.

Figure 26D:
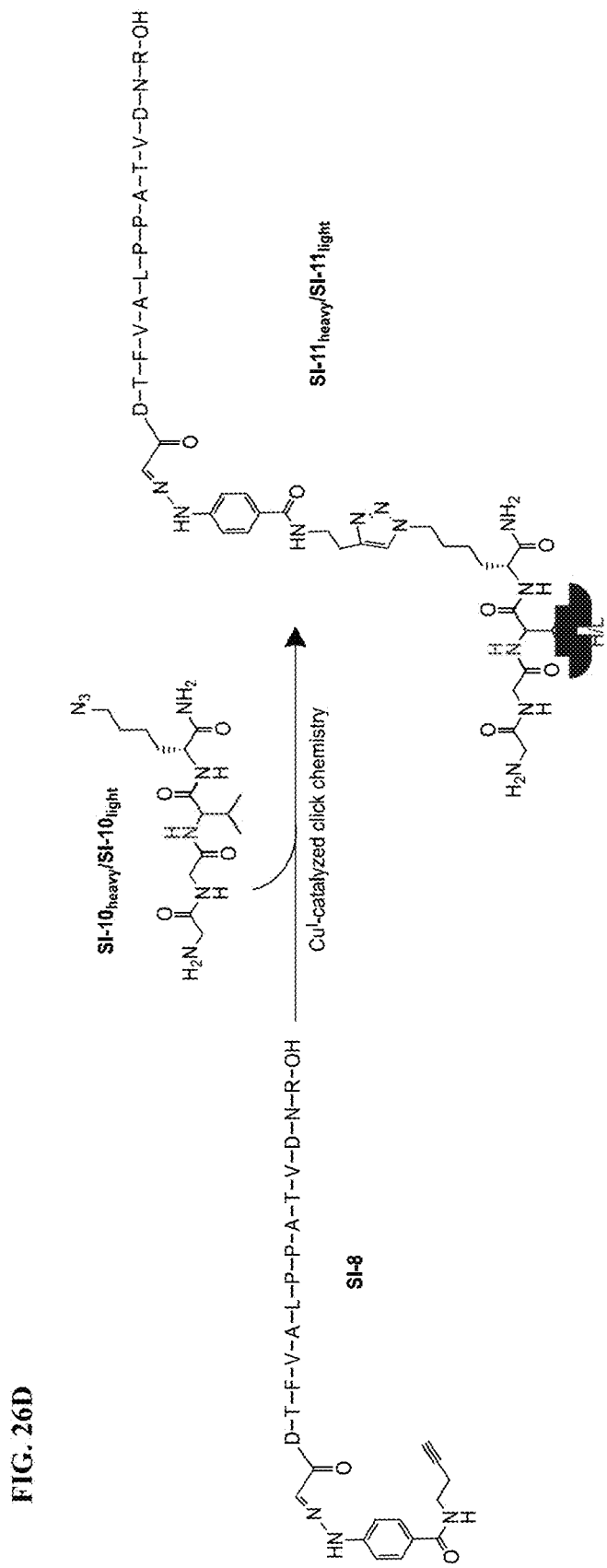

Hydrazone Product of Probe 2-labelled glyoxylyl6-Arg20 Peptide (SI-11$_{heavy}$/SI-11$_{light}$) (FIG. 26D)

The hydrazone alkyne peptide (SI-8) was conjugated to SI-10$_{heavy}$ and SI-10$_{light}$ via Cu(I)-catalyzed azide-alkyne cycloaddition (CuAAC). As described above for proteomes, TBTA (0.1 mM), CuSO$_4$ (1 mM), and TCEP (1 mM) were added to a 0.5 mL mixture of SI-8 (0.3 mM, 0.15 μmol) and either form of SI-10 (60 M, 0.03 μmol of each) in phosphate buffer (60 mM, pH 7). The reactions were incubated at ambient temperature for 2 hours and purified by RP-HPLC (gradient: 5-55% 90:10 v/v MeCN/H$_2$O in H$_2$O, 0.05 v-% TFA in 25 min; flow rate: 1 mL/min) using a Phenomenex Jupiter 5 m C18 300 Å (150×4.6 mm) column. ESI-MS calc'd for $C_{95}H_{146}N_{29}O_{28}^{+}$ and $^{13}C_5C_{90}H_{146}^{15}NN_{28}O_{28}^{+}$ ([M+H]$^-$): 2141.7 and 2147.1, found 2141.8 and 2147.6, respectively for light- and heavy-isotopologues. The estimated yields of the final standards (SI-11$_{heavy}$ and SI-11$_{light}$) were ~1 nmol as calculated based on the measured molar absorptivity ($\varepsilon_{340}$) of 26,036 M$^{-1}$ cm$^{-1}$ for SI-8. This metric compares favorably with that for other hydrazone species[89]. The product was neutralized with phosphate buffer (25 mM, pH 7), lyophilized, and frozen in aliquots at ~80° C. Prior to analysis, the standard was diluted in water, the concentration was verified spectrophotometrically, and 0.5 pmol of each standard were mixed with SCRN3 samples.

Example 6: Probe Labelling of Proteins In Vivo

Figures 24A, 24B:
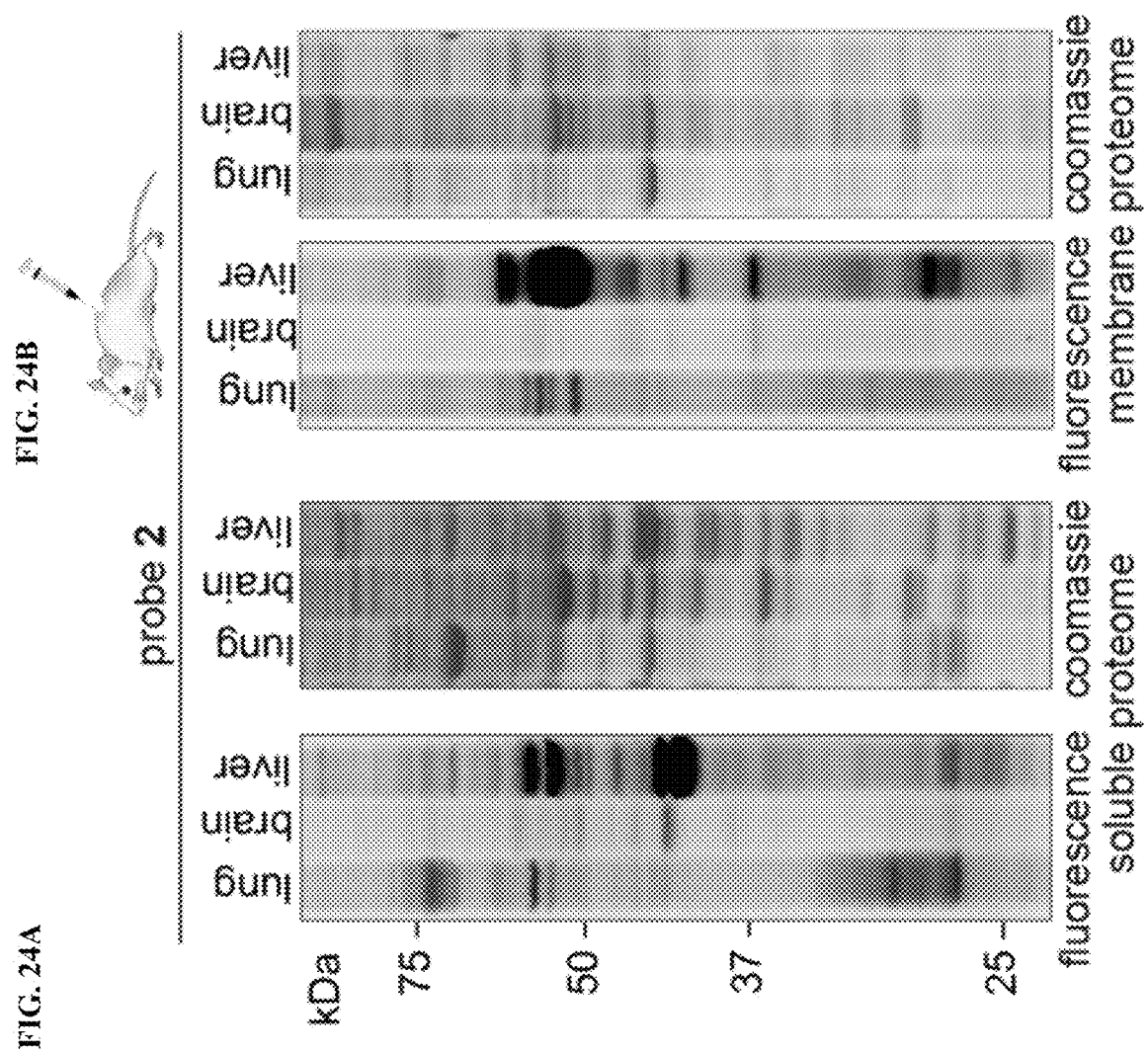
FIGS. 24A and 24B show the results of the in vivo labelling experiments with probe 2 described in Example 6.

Studies were conducted to determine whether probes can be used to label proteins in vivo. Mice were injected intraperitoneally (i.p,) with hydrazine probe 2. After treatment with probes for four hours, lung, brain and liver tissue was harvested, processed and labeled with rhodamine azide as described in Example 2. Probe labelled proteins were visualized by in-gel fluorescence scanning. The results are shown FIGS. 24A and 24B. The results demonstrate that hydrazine probes can be used to label and profile proteins in vivo according to the methods of the invention.

These results also demonstrate that probe labeling profiles of proteomes from harvested tissues are quite distinct from each other and from their corresponding protein-expression profiles. This indicates that the methods of the invention can also be used to determine the tissue specificity of certain electrophilic PTMs and/or oxidative PTMs.

Example 7: Competition Experiments with Hydrazine and Hydrazide Drugs

Competition experiments of competitor drugs phenelzine and isoniazid with probe 1 were performed in cells as described in Example 3, except that the non-clickable probe 3 was replaced with competitor drug. The results of the experiment are shown in FIG. 25. Near complete loss of probe labelling of AMD1, SCRN3, SCRN2, and LGMN proteins was observed in competition experiments performed with the hydrazine drug phenelzine, indicating that the probes target the same site of the protein as the drug. In contrast, almost no competition was observed in competition experiments with the hydrazide drug isoniazid, likely due to the fact that the hydrazide moiety of the isoniazid drug is less nucleophilic than the hydrazine moiety of the probe 1.

These results suggest that hydrazine probes can be used in the methods of the invention to identify sites in proteins that can serve as biomarkers for disease or site-specific targets for development of therapeutic drugs. These results also demonstrate that the hydrazine phenelzine competes with the clickable probes, suggesting that the methods of the invention can be used to identify other reactive, or "off-target" sites, for hydrazine drugs.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES

1. Walsh, C. T., Garneau-Tsodikova, S. & Gatto, G. J., Jr. Protein posttranslational modifications: the chemistry of proteome diversifications. Angew. Chem. Int. Ed. 44, 7342-7372 (2005).
2. Okeley, N. M. & van der Donk, W. A. Novel cofactors via post-translational modifications of enzyme active sites. Chem. Biol. 7, 159-171 (2000).
3. Olsen, J. V. & Mann, M. Status of large-scale analysis of post-translational modifications by mass spectrometry. Mol. Cell. Proteomics 12, 3444-3452 (2013).
4. Baez, N. O., Reisz, J. A. & Furdui, C. M. Mass spectrometry in studies of protein thiol chemistry and signaling: opportunities and caveats. Free Radical Biol. Med. 80, 191-211 (2015).
5. Furdui, C. M. & Poole, L. B. Chemical approaches to detect and analyze protein sulfenic acids. Mass Spectrom. Rev. 33, 126-146 (2014).
6. Chuh, K. N. & Pratt, M. R. Chemical methods for the proteome-wide identification of posttranslationally modified proteins. Curr. Opin. Chem. Biol. 24, 27-37 (2015).
7. Tate, E. W., Kalesh, K. A., Lanyon-Hogg, T., Storck, E. M. & Thinon, E. Global profiling of protein lipidation using chemical proteomic technologies. Curr. Opin. Chem. Biol. 24, 48-57 (2015).
8. Li, X. & Li, X. D. Chemical proteomics approaches to examine novel histone posttranslational modifications. Curr. Opin. Chem. Biol. 24, 80-90 (2015).
9. Cravatt, B. F., Wright, A. T. & Kozarich, J. W. Activity-based protein profiling: from enzyme chemistry to proteomic chemistry. Annu. Rev. Biochem. 77, 383-414 (2008).
10. Shannon, D. A. & Weerapana, E. Covalent protein modification: the current landscape of residue-specific electrophiles. Curr. Opin. Chem. Biol. 24, 18-26 (2015).
11. Klinman, J. P. & Bonnot, F. Intrigues and intricacies of the biosynthetic pathways for the enzymatic quinocofactors: PQQ, TTQ, CTQ, TPQ, and LTQ. Chem. Rev. 114, 4343-4365 (2014).
12. Phillips, R. S. Chemistry and diversity of pyridoxal-5'-phosphate dependent enzymes. Biochim. Biophys. Acta. 1854, 1167-1174 (2015).
13. Zhang, H., Li, X. J., Martin, D. B. & Aebersold, R. Identification and quantification of N-linked glycoproteins using hydrazide chemistry, stable isotope labeling and mass spectrometry. Nat. Biotechnol. 21, 660-666 (2003).
14. Morgan, R. K. & Cohen, M. S. A clickable aminooxy probe for monitoring cellular ADP-ribosylation. ACS Chem. Biol. 10, 1778-1784 (2015).
15. Gupta, V. & Carroll, K. S. Sulfenic acid chemistry, detection and cellular lifetime. Biochim. Biophys. Acta. 1840, 847-875 (2014).
16. Madian, A. G. & Regnier, F. E. Proteomic identification of carbonylated proteins and their oxidation sites. J. Proteome Res. 9, 3766-3780 (2010).
17. Alfaro, J. F. et al. Chemo-enzymatic detection of protein isoaspartate using protein isoaspartate methyltransferase and hydrazine trapping. Anal. Chem. 80, 3882-3889 (2008).
18. Klaene, J. J., Ni, W., Alfaro, J. F. & Zhou, Z. S. Detection and quantitation of succinimide in intact protein via hydrazine trapping and chemical derivatization. J. Pharm. Sci. 103, 3033-3042 (2014).
19. Rostovtsev, V. V., Green, L. G., Fokin, V. V. & Sharpless, K. B. A stepwise huisgen cycloaddition process: copper (I)-catalyzed regioselective "ligation" of azides and terminal alkynes. Angew. Chem. Int. Ed. 41, 2596-2599 (2002).
20. Speers, A. E., Adam, G. C. & Cravatt, B. F. Activity-based protein profiling in vivo using a copper(I)-catalyzed azide-alkyne [3+2] cycloaddition. J. Am. Chem. Soc. 125, 4686-4687 (2003).
21. Binda, C. et al. Structural and mechanistic studies of arylalkylhydrazine inhibition of human monoamine oxidases A and B. Biochemistry 47, 5616-5625 (2008).
22. Shantz, L. M., Stanley, B. A., Secrist, J. A., 3rd & Pegg, A. E. Purification of human S-adenosylmethionine decarboxylase expressed in Escherichia coli and use of this protein to investigate the mechanism of inhibition by the irreversible inhibitors, 5'-deoxy-5'-[(3-hydrazinopropyl) methylamino]adenosine and 5'-([(Z)-4-amino-2-butenyl] methylamino)-5'-deoxyadenosine. Biochemistry 31, 6848-6855 (1992).
23. Washburn, M. P., Wolters, D. & Yates, J. R., 3rd. Large-scale analysis of the yeast proteome by multidimensional protein identification technology. Nat. Biotechnol. 19, 242-247 (2001).
24. Mann, M. Functional and quantitative proteomics using SILAC. Nat. Rev. Mol. Cell Biol. 7, 952-958 (2006).
25. Adibekian, A. et al. Click-generated triazole ureas as ultrapotent in vivo-active serine hydrolase inhibitors. Nat. Chem. Biol. 7, 469-478 (2011).
26. Dalle-Donne, I. et al. Protein carbonylation: 2,4-dinitrophenylhydrazine reacts with both aldehydes/ketones and sulfenic acids. Free Radical Biol. Med. 46, 1411-1419 (2009).
27. Gupta, V., Paritala, H. & Carroll, K. S. Reactivity, selectivity and stability in sulfenic acid detection: A comparative study of nucleophilic and electropilic probes. Bioconjugate Chem. (2016).
28. Tolbert, W. D. et al. The structural basis for substrate specificity and inhibition of human S-adenosylmethionine decarboxylase. Biochemistry 40, 9484-9494 (2001).
29. McCloskey, D. E. et al. New insights into the design of inhibitors of human S-adenosylmethionine decarboxy- 29. lase: studies of adenine C8 substitution in structural analogues of S-adenosylmethionine. J. Med. Chem. 52, 1388-1407 (2009).
30. Shantz, L. M., Holm, I., Janne, O. A. & Pegg, A. E. Regulation of S-adenosylmethionine decarboxylase activity by alterations in the intracellular polyamine content. Biochem. J. 288, 511-518 (1992).
31. Zinellu, A. et al. Plasma methionine determination by capillary electrophoresis-UV assay: application on patients affected by retinal venous occlusive disease. Anal. Biochem. 363, 91-96 (2007).
32. Xiong, H., Stanley, B. A. & Pegg, A. E. Role of cysteine-82 in the catalytic mechanism of human S-adenosylmethionine decarboxylase. Biochemistry 38, 2462-2470 (1999).
33. Weerapana, E. et al. Quantitative reactivity profiling predicts functional cysteines in proteomes. Nature 468, 790-795 (2010).
34. Weerapana, E., Speers, A. E. & Cravatt, B. F. Tandem orthogonal proteolysis-activity-based protein profiling (TOP-ABPP)—a general method for mapping sites of probe modification in proteomes. Nat. Protoc. 2, 1414-1425 (2007).
35. Pei, J. & Grishin, N. V. Peptidase family U34 belongs to the superfamily of N-terminal nucleophile hydrolases. Protein Sci. 12, 1131-1135 (2003).
36. Brannigan, J. A. et al. A protein catalytic framework with an N-terminal nucleophile is capable of self-activation. Nature 378, 416-419 (1995).
37. Xiong, H. & Pegg, A. E. Mechanistic studies of the processing of human S-adenosylmethionine decarboxylase proenzyme. Isolation of an ester intermediate. J. Biol. Chem. 274, 35059-35066 (1999).
38. Dirksen, A., Dirksen, S., Hackeng, T. M. & Dawson, P. E. Nucleophilic catalysis of hydrazone formation and transimination: implications for dynamic covalent chemistry. J. Am. Chem. Soc. 128, 15602-15603 (2006).
39. Dirksen, A. & Dawson, P. E. Rapid oxime and hydrazone ligations with aromatic aldehydes for biomolecular labeling. Bioconjug. Chem. 19, 2543-2548 (2008).
40. Yerlikaya, A. & Stanley, B. A. S-adenosylmethionine decarboxylase degradation by the 26S proteasome is accelerated by substrate-mediated transamination. J. Biol. Chem. 279, 12469-12478 (2004).
41. Dall, E., Fegg, J. C., Briza, P. & Brandstetter, H. Structure and mechanism of an aspartimide-dependent peptide ligase in human legumain. Angew. Chem. Int. Ed. 54, 2917-2921 (2015).
42. Casero, R. A., Jr. & Marton, L. J. Targeting polyamine metabolism and function in cancer and other hyperproliferative diseases. Nat. Rev. Drug Discov. 6, 373-390 (2007).
43. Jaramillo, M. C. & Zhang, D. D. The emerging role of the Nrf2-Keap1 signaling pathway in cancer. Genes Dev. 27, 2179-2191 (2013).
44. Blennow, K., Mattsson, N., Scholl, M., Hansson, O. & Zetterberg, H. Amyloid biomarkers in Alzheimer's disease. Trends Pharmacol. Sci. 36, 297-309 (2015).
45. Yang, J. et al. FTO genotype is associated with phenotypic variability of body mass index. Nature 490, 267-272 (2012).
46. Buckingham, J. The chemistry of arylhydrazones. Q. Rev. Chem. Soc. 23, 37-56 (1969).
47. Huizinga, E. G. et al. Active site structure of methylamine dehydrogenase: hydrazines identify C6 as the reactive site of the tryptophan-derived quinone cofactor. Biochemistry 31, 9789-9795 (1992).
48. Appel, M. J. & Bertozzi, C. R. Formylglycine, a post-translationally generated residue with unique catalytic capabilities and biotechnology applications. ACS Chem. Biol. 10, 72-84 (2015).
49. Xu, Q., Buckley, D., Guan, C. & Guo, H. C. Structural insights into the mechanism of intramolecular proteolysis. Cell 98, 651-661 (1999).
50. Kabisch, U. C. et al. Identification of D-proline reductase from Clostridium sticklandii as a selenoenzyme and indications for a catalytically active pyruvoyl group derived from a cysteine residue by cleavage of a proprotein. J. Biol. Chem. 274, 8445-8454 (1999).
51. Andreesen, J. R. Glycine reductase mechanism. Curr. Opin. Chem. Biol. 8, 454-461 (2004).
52. Mihara, H. & Esaki, N. Bacterial cysteine desulfurases: their function and mechanisms. Appl. Microbiol. Biotechnol. 60, 12-23 (2002).
53. Scheck, R. A., Dedeo, M. T., Iavarone, A. T. & Francis, M. B. Optimization of a biomimetic transamination reaction. J. Am. Chem. Soc. 130, 11762-11770 (2008).
54. Shantz, L. M., Stanley, B. A., Secrist, J. A., III & Pegg, A. E. Purification of human S-adenosylmethionine decarboxylase expressed in Escherichia coli and use of this protein to investigate the mechanism of inhibition by the irreversible inhibitors, 5'-deoxy-5'-[(3-hydrazinopropyl) methylamino]adenosine and 5'-([(Z)-4-amino-2-butenyl] methylamino)-5'-deoxyadenosine. Biochemistry 31, 6848-6855 (1992).
55. Carlson, B. L. et al. Function and structure of a prokaryotic formylglycine-generating enzyme. J. Biol. Chem. 283, 20117-20125 (2008).
56. Klaene, J. J., Ni, W., Alfaro, J. F. & Zhou, Z. S. Detection and quantitation of succinimide in intact protein via hydrazine trapping and chemical derivatization. J. Pharm. Sci. 103, 3033-3042 (2014).
57. Klinman, J. P. & Bonnot, F. Intrigues and intricacies of the biosynthetic pathways for the enzymatic quinocofactors: PQQ, TTQ, CTQ, TPQ, and LTQ. Chem. Rev. 114, 4343-4365 (2014).
58. Augusto, O., Kunze, K. L. & Ortiz de Montellano, P. R. N-phenylprotoporphyrin IX formation in the hemoglobin-phenylhydrazine reaction. Evidence for a protein-stabilized iron-phenyl intermediate. J. Biol. Chem. 257, 6231-6241 (1982).
59. Binda, C. et al. Structural and mechanistic studies of arylalkylhydrazine inhibition of human monoamine oxidases A and B. Biochemistry 47, 5616-5625 (2008).
60. Pegg, A. E. Mammalian polyamine metabolism and function. IUBMB Life 61, 880-894 (2009).
61. Metanis, N., Keinan, E. & Dawson, P. E. Traceless ligation of cysteine peptides using selective deselenization. Angew. Chem. Int. Ed. 49, 7049-7053 (2010).
62. Ong, S. E. et al. Stable isotope labeling by amino acids in cell culture, SILAC, as a simple and accurate approach to expression proteomics. Mol. Cell. Proteomics 1, 376-386 (2002).
63. Mann, M. Functional and quantitative proteomics using SILAC. Nat. Rev. Mol. Cell Biol. 7, 952-958 (2006).
64. Speers, A. E. & Cravatt, B. F. Profiling enzyme activities in vivo using click chemistry methods. Chem. Biol. 11, 535-546 (2004).
65. Adibekian, A. et al. Click-generated triazole ureas as ultrapotent in vivo-active serine hydrolase inhibitors. Nat. Chem. Biol. 7, 469-478 (2011).
66. Martin, B. R., Wang, C., Adibekian, A., Tully, S. E. & Cravatt, B. F. Global profiling of dynamic protein palmitoylation. Nat. Methods. 9, 84-89 (2012).

67. Hulce, J. J., Cognetta, A. B., Niphakis, M. J., Tully, S. E. & Cravatt, B. F. Proteome-wide mapping of cholesterol-interacting proteins in mammalian cells. Nat. Methods 10, 259-264 (2013).
68. Niphakis, M. J. et al. A global map of lipid-binding proteins and their ligandability in cells. Cell 161, 1668-1680 (2015).
69. Weerapana, E. et al. Quantitative reactivity profiling predicts functional cysteines in proteomes. Nature 468, 790-795 (2010).
70. Washburn, M. P., Wolters, D. & Yates, J. R., III. Large-scale analysis of the yeast proteome by multidimensional protein identification technology. Nat. Biotechnol. 19, 242-247 (2001).
71. He, L., Diedrich, J., Chu, Y. Y. & Yates, J. R., III. Extracting accurate precursor information for tandem mass spectra by RawConverter. Anal. Chem. 87, 11361-11367 (2015).
72. Ekstrom, J. L., Mathews, I I, Stanley, B. A., Pegg, A. E. & Ealick, S. E. The crystal structure of human S-adenosylmethionine decarboxylase at 2.25 A resolution reveals a novel fold. Structure 7, 583-595 (1999).
73. Kameji, T. & Pegg, A. E. Effect of putrescine on the synthesis of S-adenosylmethionine decarboxylase. Biochem. J. 243, 285-288 (1987).
74. Gill, S. C. & von Hippel, P. H. Calculation of protein extinction coefficients from amino acid sequence data. Anal. Biochem. 182, 319-326 (1989).
75. Schneider, C. A., Rasband, W. S. & Eliceiri, K. W. NIH Image to ImageJ: 25 years of image analysis. Nat. Methods 9, 671-675 (2012).
76. Boersema, P. J., Raijmakers, R., Lemeer, S., Mohammed, S. & Heck, A. J. Multiplex peptide stable isotope dimethyl labeling for quantitative proteomics. Nat. Protoc. 4, 484-494 (2009).
77. Weerapana, E., Speers, A. E. & Cravatt, B. F. Tandem orthogonal proteolysis-activity-based protein profiling (TOP-ABPP)-a general method for mapping sites of probe modification in proteomes. Nat. Protoc. 2, 1414-1425 (2007).
78. Xu, T., Venable, J. D., Park, S. K., Cociorva, D., Lu, B., Liao, L., Wohlschlegel, J., Hewel, J., Yates, J. R., III. ProLuCID, a fast and sensitive tandem mass spectra-based protein identification program. Mol. Cell. Proteomics 5, S174 (2006).
79. Kim, M. S., Kandasamy, K., Chaerkady, R. & Pandey, A. Assessment of resolution parameters for CID-based shotgun proteomic experiments on the LTQ-Orbitrap mass spectrometer. J. Am. Soc. Mass Spectrom. 21, 1606-1611 (2010).
80. Breci, L. A., Tabb, D. L., Yates, J. R., III & Wysocki, V. H. Cleavage N-terminal to proline: analysis of a database of peptide tandem mass spectra. Anal. Chem. 75, 1963-1971 (2003).
81. Eng, J. K., McCormack, A. L. & Yates, J. R., III. An approach to correlate tandem mass spectral data of peptides with amino acid sequences in a protein database. J. Am. Soc. Mass Spectrom. 5, 976-989 (1994).
82. Perkins, D. N., Pappin, D. J., Creasy, D. M. & Cottrell, J. S. Probability-based protein identification by searching sequence databases using mass spectrometry data. Electrophoresis 20, 3551-3567 (1999).
83. Cox, J. et al. Andromeda: a peptide search engine integrated into the MaxQuant environment. J. Proteome Res. 10, 1794-1805 (2011).
84. Zhang, J. et al. PEAKS DB: de novo sequencing assisted database search for sensitive and accurate peptide identification. Mol. Cell. Proteomics 11, 1-8 (2012).
85. Dirksen, A., Dirksen, S., Hackeng, T. M. & Dawson, P. E. Nucleophilic catalysis of hydrazone formation and transimination: implications for dynamic covalent chemistry. J. Am. Chem. Soc. 128, 15602-15603 (2006).
86. Matthews, M. L. et al. Substrate-triggered formation and remarkable stability of the C—H bond-cleaving chloroferryl intermediate in the aliphatic halogenase, SyrB2. Biochemistry 48, 4331-4343 (2009).
87. Rasmussen, L. K. Facile synthesis of mono-, di-, and trisubstituted alpha-unbranched hydrazines. J. Org. Chem. 71, 3627-3629 (2006).
88. Lamberto, I. et al. Development and structural analysis of a nanomolar cyclic peptide antagonist for the EphA4 receptor. ACS Chem. Biol. 9, 2787-2795 (2014).
89. Hermanson, G. Bioconjugate Techniques, 3rd Ed., (Academic Press, 2013).
90. Matthews et al. "Chemoproteomic profiling and discovery of protein electrophiles in human cells," *Nature Chemistry*, (2017) 9(3), 234-243.

The invention claimed is:

1. A method for detecting an endogenous electrophilic post-translational modification (PTM) or an endogenous oxidative PTM of at least one protein in a proteomic mixture in a living organism or living cell, the method comprising:

(i) contacting the proteomic mixture in the living organism or living cell with a probe comprising a hydrazine moiety and an alkyne moiety to form a covalent linkage between the hydrazine moiety of the probe and the endogenous electrophilic PTM or the endogenous oxidative PTM of the at least one protein, thereby forming a mixture comprising at least one alkyne-derivatized protein, wherein the probe having the structure of formula (1) or (2)

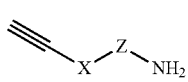

(1)

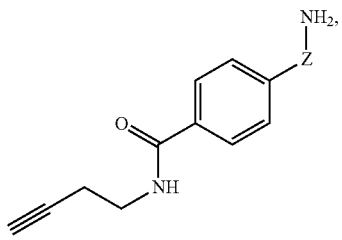

(2)

wherein Z=NH and X is a linker selected from the group consisting of alkyl, aryl, and arylamines, wherein the endogenous electrophilic PTM or the endogenous oxidative PTM is a functional modification that affects a biological activity of the at least one protein and is installed onto the at least one protein by dedicated enzyme machinery or by high affinity binding of metabolite-derived small molecules;

(ii) labelling the at least one alkyne-derivatized protein with an azide-modified tag, optionally in the presence of a copper catalyst, to obtain at least one labelled protein; and (iii) analyzing the at least one labelled protein to thereby detect the endogenous electrophilic PTM or the endogenous oxidative PTM of the at least one protein.

2. The method of claim 1, further comprising enriching the at least one labelled protein from the proteomic mixture.

3. The method of claim 1, wherein the tag is an imaging agent, an enrichment tag, an isotope tag, degradation tag, or chemical or enzymatic cleavage tag.

4. The method of claim 1, wherein the endogenous electrophilic PTM is a pyruvoyl modification, glyoxylyl modification, formylglycyl modification, aspartimide modification, aspartyl phosphate modification, or quinone modification.

5. The method of claim 1, wherein the oxidative PTM is a Flavin cofactor, heme iron cofactor, or non-heme iron cofactor.

6. The method of claim 1, further comprising identifying the at least one labelled protein.

7. The method of claim 6, wherein identifying the at least one labelled protein comprises analysis by mass spectrometry.

8. A method for profiling an endogenous electrophilic post-translational modification (PTM) or an endogenous oxidative PTM of at least one protein in a proteomic mixture in a living organism or living cell, the method comprising:

(i) contacting the proteomic mixture in the living organism or living cell with a probe comprising a hydrazine moiety and an alkyne moiety to form a covalent linkage between the hydrazine moiety of the probe and the endogenous electrophilic (PTM) or the endogenous oxidative PTM of the at least one protein to obtain at least one alkyne-derivatized protein, wherein the probe having the structure of formula (1) or (2)

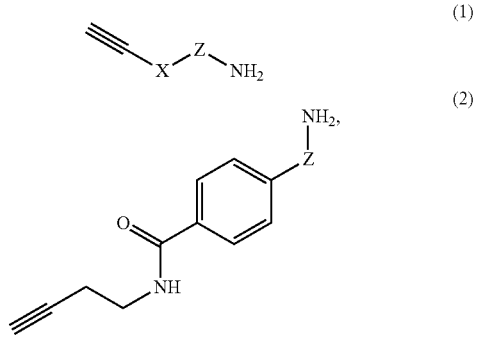

wherein Z=NH and X is a linker selected from the group consisting of alkyl, aryl, and arylamines, wherein the endogenous electrophilic PTM or the endogenous oxidative PTM is a functional modification that affects a biological activity of the at least one protein and is installed on the at least one protein by dedicated enzyme machinery or by high affinity binding of metabolite-derived small molecules;

(ii) labelling the at least one alkyne-derivatized protein with an azide-modified tag, optionally in the presence of a copper catalyst, to obtain at least one labelled protein;

(iii) enriching the at least one labelled protein; and (iv) quantifying the at least one labelled protein.

9. The method of claim 8, wherein the tag is an imaging agent, an enrichment tag, an isotope tag, degradation tag, or chemical or enzymatic cleavage tag.

10. The method of claim 8, wherein the endogenous electrophilic PTM of the at least one protein is a pyruvoyl modification, glyoxylyl modification, formylglycyl modification, aspartimide modification, aspartyl phosphate modification, or quinone modification; and the oxidative PTM of the at least one protein is a Flavin cofactor, heme iron cofactor, or non-heme iron cofactor.

11. The method of claim 8, wherein quantification of the at least one protein comprises analysis by mass spectrometry.

12. The method of claim 8, wherein the at least one protein is selected from the group consisting of AMD1 S-adenosylmethionine decarboxylase, LGMN Legumain, SCRN3 Secernin-3, SCRN2 Secernin-2, RARS2 Probable arginine tRNA ligase, KEAP1 Kelchlike ECHassociated protein 1, MAN2B1 Lysosomal alphamannosidase, APLP2 Amyloidlike protein 2, APP Amyloid beta A4 protein, EPDR1 Mammalian ependyminrelated, CCBL2 Kynurenine oxoglutarate transaminase, FASTICD5 FAST kinase domain containing, ALDOA Fructosebisphosphate aldolase, ALDOC Fructosebisphosphate aldolase, NT5DC2 5nucleotidase domain containing, CPVL Probable serine carboxypeptidase, GLA Alphagalactosidase A, IBA57 Putative transferase CAF17, ALDH1B1 Aldehyde dehydrogenase X, GLB1 Betagalactosidase, ALDH2 Aldehyde dehydrogenase, BLVRB Flavin reductase (NADPH), DCUN1D5 DCNllike protein 5, PLD3 Phospholipase D3, ALDH9A1 4trimethylaminobutyraldehyde, SCPEP1 Retinoidinducible serine, CTSD Cathepsin D, BLMH Bleomycin hydrolase, PPA2 Inorganic pyrophosphatase, IRS4 Insulin receptor substrate 4, CTSZ Cathepsin Z, SERPINE1 Plasminogen activator inhibitor 1, CTSB Cathepsin B, LGALS3BP Galectin3binding protein, LEPRE1 Prolyl 3hydroxylase 1, TPP1 Tripeptidylpeptidase 1, PLOD3 Procollagenlysine, 2oxoglutarate, VAPA Vesicleassociated membrane, THBS1 Thrombospondin1, NSFL1C NSFL1 cofactor p47, LIPA Lysosomal acid lipase/cholesteryl ester, PSAP Proactivator polypeptide, PLOD1 Procollagenlysine, 2oxoglutarate, GNS Nacetylglucosamine6sulfatase, GAA Lysosomal alphaglucosidase, P4HA1 Prolyl 4hydroxylase subunit alpha1, and PITRM1 Presequence protease mitochondrial.

13. The method of claim 8, wherein the at least one protein is selected from the group consisting of SCRN3 Secernin-3, PHF8 Histone lysine demethylase PHF8, SCRN2 Secernin-2, SCD AcylCoA desaturase, ALKBH1 Alkylated DNA repair protein alkB, PLOD3 Procollagenlysine, 2oxoglutarate, ALDH2 Aldehyde dehydrogenase mitochondrial, AMD1 S-adenosylmethionine decarboxylase, CYP51A1 Lanosterol 14alpha demethylase, HMOX2 Heme oxygenase 2, FTO Alphaketoglutaratedependent dioxygenase, ALDOA Fructosebisphosphate aldolase A, ALDOC Fructosebisphosphate aldolase C, ALDH1B1 Aldehyde dehydrogenase X, FADS1 Fatty acid desaturase 1, PYROXD2 Pyridine nucleotidedisulfide, CPD Carboxypeptidase D, EPDR1 Mammalian ependyminrelated, FTH1 Ferritin heavy chain, PXDN Peroxidasin homolog, PPT1 Palmitoylprotein thioesterase 1, CTSB Cathepsin B, CTSZ Cathepsin Z, CTSA Lysosomal protective protein, CTSC Dipeptidyl peptidase 1, PHYHD1 PhytanoylCoA dioxygenase, PSAP Proactivator polypeptide, DENR Densityregulated protein, CTSD Cathepsin D, MAN2B1 Lysosomal alphamannosidase, TPP1 Tripeptidylpeptidase, SCPEP1 Retinoidinducible serine, XPNPEP3 Probable XaaPro aminopeptidase 3, IBA57 Putative transferase CAF17, FADS2

Fatty acid desaturase 2, NT5DC2 5nucleotidase domain containing, FASTKD5 FAST kinase domain containing, KDM1A Lysine specific histone demethylase 1A, ACOX1 Peroxisomal acylcoenzyme A oxidase 1, KDM5C Lysine-specific demethylase 5C, CMBL Carboxymethylenebutenolidase homolog, KDM1B Lysinespecific histone demethylase 1B, TTC38 Tetratricopeptide repeat protein 38, RRM2 Ribonucleosidediphosphate reductase, MINA MYCinduced nuclear antigen, CYCS Cytochrome c, PLD3 Phospholipase D3, GAA Lysosomal alphaglucosidase, ERAP1 Endoplasmic reticulum aminopeptidase, ASAH1 Acid ceramidase, PRCP Lysosomal ProX carboxypeptidase, CTSS Cathepsin S, CYP27A1 Sterol 26hydroxylase, mitochondrial, FTL Ferritin light chain, LIPA Lysosomal acid lipase/cholesteryl ester, SERPINE1 Plasminogen activator inhibitor 1, CAT Catalase, NAGA AlphaNacetylgalactosaminidase, aminotransferase, mitoch, KEAP1 Kelchlike ECHassociated protein 1, HEXB Betahexosaminidase subunit beta, MMP14 Matrix metalloproteinase14, PLBD2 Putative phospholipase Blike 2, LEPRE1 Prolyl 3hydroxylase 1, LGALS3BP Galectin3binding protein, NEU1 Sialidase1, RAB14 Rasrelated protein Rab14, LGMN Legumain, SELENBP1 Seleniumbinding protein 1, PLOD1 Procollagenlysine, 2oxoglutarate, P4HA2 Prolyl 4hydroxylase subunit alpha2, P4HA1 Prolyl 4hydroxylase subunit alpha1, BCAT1 Branchedchain-aminoacid, ACOX3 Peroxisomal acylcoenzyme A oxidase 3, PTGR2 Prostaglandin reductase 2, RRM2B Ribonucleosidediphosphate reductase, GNS Nacetylglucosamine6sulfatase, GLB1 Betagalactosidase, ACAA1 3ketoacylCoA thiolase, peroxisomal, and PLOD2 Procollagenlysine, 2oxoglutarate.

\* \* \* \* \*